US010216828B2

(12) United States Patent
Singh et al.

(10) Patent No.: US 10,216,828 B2
(45) Date of Patent: Feb. 26, 2019

(54) SCALABLE TOPOLOGICAL SUMMARY CONSTRUCTION USING LANDMARK POINT SELECTION

(71) Applicant: Ayasdi, Inc., Menlo Park, CA (US)

(72) Inventors: Gurjeet Singh, Palo Alto, CA (US); Lawrence Spracklen, Boulder Creek, CA (US); Ryan Hsu, San Francisco, CA (US)

(73) Assignee: Ayasdi, Inc., Menlo Park, CA (US)

( * ) Notice: Subject to any disclaimer, the term of this patent is extended or adjusted under 35 U.S.C. 154(b) by 103 days.

(21) Appl. No.: 15/147,821

(22) Filed: May 5, 2016

(65) Prior Publication Data

US 2016/0246871 A1    Aug. 25, 2016

Related U.S. Application Data

(63) Continuation-in-part of application No. 14/884,511, filed on Oct. 15, 2015, now Pat. No. 10,002,180.
(Continued)

(51) Int. Cl.
*G06F 17/30* (2006.01)
*G06Q 10/08* (2012.01)
(Continued)

(52) U.S. Cl.
CPC ........ *G06F 17/30598* (2013.01); *G06F 19/12* (2013.01); *G06F 19/24* (2013.01); *G06Q 10/08355* (2013.01)

(58) Field of Classification Search
CPC .... G06F 17/30598; G06F 19/12; G06F 19/24; G06Q 10/08355
(Continued)

(56) References Cited

U.S. PATENT DOCUMENTS

| 4,878,170 A * | 10/1989 | Zeevi | G01C 21/30 701/438 |
| 6,920,391 B2 * | 7/2005 | Daubert | G06T 17/05 340/995.19 |

(Continued)

OTHER PUBLICATIONS

International Application No. PCT/US2015/019066, International Search Report and Written Opinion dated Jun. 11, 2015.
(Continued)

*Primary Examiner* — Phong H Nguyen
(74) *Attorney, Agent, or Firm* — Sheppard, Mullin, Richter & Hampton LLP

(57) ABSTRACT

An example method comprises receiving data points, determining at least one size of a plurality of subsets based on a constraint of at least one computation device or an analysis server, transferring each of the subsets to different computation devices, each computation device selecting a group of data points to generate a first sub-subset of landmarks, add non-landmark data points that have the farthest distance to the closest landmark to create an expanded sub-subset of landmarks, create an analysis landmark set based on a combination of expanded sub-subsets of expanded landmarks from different computation devices, perform a similarity function on the analysis landmark set, generate a cover of the mathematical reference space to create overlapping subsets, cluster the mapped landmark points based on the overlapping subsets, create a plurality of nodes, each node being based on the clustering, each landmark point being a member of at least one node.

15 Claims, 38 Drawing Sheets

Related U.S. Application Data which is a continuation-in-part of application No. 14/639,954, filed on Mar. 5, 2015, now Pat. No. 10,042,959.

(60) Provisional application No. 62/157,405, filed on May 5, 2015, provisional application No. 61/948,490, filed on Mar. 5, 2014.

(51) Int. Cl.
*G06F 19/12* (2011.01)
*G06F 19/24* (2011.01)

(58) Field of Classification Search
USPC .................................................. 707/737, 798
See application file for complete search history.

(56) References Cited

U.S. PATENT DOCUMENTS

| | | | | |
|---|---|---|---|---|
| 7,756,342 | B2* | 7/2010 | Bachmann | G06K 9/6252 283/91 |
| 7,831,381 | B2* | 11/2010 | Thota | G01C 21/3679 340/995.24 |
| 2003/0120421 | A1* | 6/2003 | Daubert | G06T 17/05 701/400 |
| 2005/0198328 | A1* | 9/2005 | Lee | H04L 45/02 709/229 |
| 2006/0251324 | A1* | 11/2006 | Bachmann | G06K 9/0063 382/173 |
| 2009/0043504 | A1* | 2/2009 | Bandyopadhyay | G01C 17/38 701/469 |
| 2010/0254582 | A1* | 10/2010 | Liu | G06K 9/4638 382/131 |
| 2010/0313157 | A1 | 12/2010 | Carlsson et al. | |
| 2011/0261049 | A1* | 10/2011 | Cardno | G06Q 10/10 345/419 |
| 2011/0307433 | A1 | 12/2011 | Dlugosch | |
| 2012/0130632 | A1* | 5/2012 | Bandyopadhyay | G01C 17/38 701/446 |
| 2013/0101221 | A1 | 4/2013 | Fujiki et al. | |
| 2013/0144916 | A1 | 6/2013 | Lum et al. | |
| 2013/0185624 | A1 | 7/2013 | Appleyard et al. | |
| 2013/0187922 | A1 | 7/2013 | Sexton | |
| 2013/0259353 | A1* | 10/2013 | Hewett | G06F 19/321 382/132 |
| 2013/0297543 | A1 | 11/2013 | Treiser | |
| 2014/0229768 | A1 | 8/2014 | Bernstein et al. | |
| 2014/0278479 | A1 | 9/2014 | Wang et al. | |
| 2014/0330867 | A1 | 11/2014 | Sarkar et al. | |
| 2014/0337390 | A1 | 11/2014 | Kumar | |
| 2015/0106578 | A1 | 4/2015 | Warfield et al. | |
| 2015/0254370 | A1 | 9/2015 | Sexton et al. | |
| 2016/0034561 | A1 | 2/2016 | Sexton et al. | |

OTHER PUBLICATIONS

International Application No. PCT/US2016/031065, International Search Report and Written Opinion dated Aug. 31, 2016.

Nicolau, Monica et al., "Topology Based Data Analysis Identifies a Subgroup of Breast Cancers with a Unique Mutational Profile and Excellent Survival," Proceedings of the National Academy of Sciences of the United States of America, vol. 108, No. 17, pp. 7265-7270, Apr. 26, 2011.

European Patent Application No. 15757741.2, Search Report dated Jun. 28, 2017.

International Application No. PCT/US2016/066233, International Search Report and Written Opinion dated Apr. 7, 2017.

\* cited by examiner

| Patient ID | Gene 1 Expression | Gene 2 Expression | ... | Gene y Expression | Clinical Outcome |
|---|---|---|---|---|---|
| P1 | G1a | G2a | | Gya | Outcome P1 |
| P2 | G1b | G2b | | Gyb | Outcome P2 |
| P3 | G1c | G2c | | Gyc | Outcome P3 |
| ⋮ | ⋮ | ⋮ | | ⋮ | ⋮ |
| Pn | G1n | G2n | | Gyn | Outcome Pn |

FIG. 13

| Landmark | Distance (d) from P1 | Distance (d) from P2 |
|---|---|---|
| R1 | 3 | 5 |
| R2 | 5 | 7 |
| R3 | 7 | 9 |
| R4 | 6 | 8 |

| Data Point | d to nearest Landmark |
|---|---|
| P1 | 3 |
| P2 | 5 |
| P3 | 4 |

| Data Point | d to nearest Landmark |
|---|---|
| P1 | 3 |
| P2 | 5 |
| P3 | 4 |
| P4 | 4 |

SCALABLE TOPOLOGICAL SUMMARY CONSTRUCTION USING LANDMARK POINT SELECTION

CROSS-REFERENCE TO RELATED APPLICATIONS

This application claims priority to U.S. Patent Application Ser. No. 62/157,405, filed May 5, 2015, entitled "Scalable Topological Summary Construction," which is incorporated by reference. This application is a continuation-in-part of and claims priority to U.S. patent application Ser. No. 14/884,511, filed Oct. 15, 2015, entitled "Landmark Point Selection," which is a continuation-in-part of and claims priority to U.S. patent application Ser. No. 14/639,954, filed Mar. 5, 2015, entitled "Systems and Methods for Capture of Relationships Within Information," which claims priority to U.S. Provisional Patent Application Ser. No. 61/948,490, filed Mar. 5, 2014, entitled "Systems and Methods For Landmarked Stochastic Neighbor Embedding," all of which are incorporated by reference herein.

BACKGROUND

1. Field of the Invention(s)

Embodiments discussed herein are directed to grouping of data points for data analysis and more particularly to generating a graph utilizing improved groupings of data points based on scores of the groupings.

2. Related Art

As the collection and storage data has increased, there is an increased need to analyze and make sense of large amounts of data. Examples of large datasets may be found in financial services companies, oil expiration, biotech, and academia. Unfortunately, previous methods of analysis of large multidimensional datasets tend to be insufficient (if possible at all) to identify important relationships and may be computationally inefficient.

In order to process large datasets, some previous methods of analysis use clustering. Clustering often breaks important relationships and is often too blunt an instrument to assist in the identification of important relationships in the data. Similarly, previous methods of linear regression, projection pursuit, principal component analysis, and multidimensional scaling often do not reveal important relationships. Further, existing linear algebraic and analytic methods are too sensitive to large scale distances and, as a result, lose detail.

Even if the data is analyzed, sophisticated experts are often necessary to interpret and understand the output of previous methods. Although some previous methods allow graphs that depict some relationships in the data, the graphs are not interactive and require considerable time for a team of such experts to understand the relationships. Further, the output of previous methods does not allow for exploratory data analysis where the analysis can be quickly modified to discover new relationships. Rather, previous methods require the formulation of a hypothesis before testing.

SUMMARY OF THE INVENTION(S)

An example method comprises receiving a large number of data points, determining at least one size of a plurality of subsets of the large number of data points based on constraints of at least one of a plurality of computation devices or an analysis server, each data point of the large number of data points being a member of at least one of the plurality of subsets of the large number of data points, transferring each of the plurality of subsets of large number of data points to a respective one of the plurality of computation devices, for each of the plurality of subsets of data points by an associated computation device of the plurality of computation devices: selecting, by the associated computation device, a group of data points from the subset of data points to generate a first sub-subset of landmarks, adding, by the associated computation device, a non-landmark data point of the subset of data points to the first sub-subset of landmarks to create an expanded sub-subset of landmarks, adding the non-landmark data points comprising calculating first data point distances between each non-landmark data point and each landmark, identifying a shortest data point distance from among the first data point distances for each non-landmark data point, identifying a particular non-landmark data point with a longest first landmark distance of all the shortest data path distances, and adding the particular non-landmark data point to the first sub-subset of landmarks to expand the first sub-subset of landmarks to generate an expanded set of landmarks, until the expanded sub-subset of the expanded landmarks reaches a predetermined number of members, repeat adding the non-landmark data points, creating an analysis landmark set based on a combination of expanded sub-subsets of expanded landmarks, performing a similarity function on the analysis landmark set to map landmark points of the analysis landmark set to a mathematical reference space, generating a cover of the mathematical reference space to divide the mathematical reference space into overlapping subsets, clustering the mapped landmark points of the analysis landmark set based on the overlapping subsets of the cover in the mathematical reference space, creating a plurality of nodes, each of the plurality of nodes being based on the clustering of the mapped landmark points of the analysis landmark set, each landmark point of the analysis landmark set being a member of at least one node, and connecting at least two of the plurality of nodes with an edge if the at least two of the plurality of nodes share at least one landmark point of the analysis landmark set as a member.

In some embodiments, the method further comprises for each data point that is both a member of the large data set but is not a member of the analysis landmark set: determining a distance between that data point and all landmark points of the analysis landmark set, identifying a closest landmark of the analysis landmark set to that data point, identifying node that includes the closest landmark of the analysis landmark set, and adding that data point as a member of the node that includes the closest landmark of the analysis landmark set. In some embodiments, the method further comprises generating a visualization of the plurality of nodes and edge.

In various embodiments, the method further comprises for each data point that is both a member of the large data set but is not a member of the analysis landmark set: determining a distance between that data point and all landmark points of the analysis landmark set, identifying a closest landmark of the analysis landmark set to that data point, comparing a distance between the closest landmark of the analysis landmark set and that data point to a node threshold, and if the distance between the closest landmark of the analysis landmark set and that data point is greater than the node threshold, generating a new node including that data point as a member of the new node, if the distance the distance between the closest landmark of the analysis landmark set and that data point is less than the node threshold, adding that data point as a member of the node that includes the closest landmark of the analysis landmark set.

The method may further comprise for each data point that is both a member of the large data set but is not a member of the analysis landmark set: determining a distance between that data point and all landmark points of the analysis landmark set, identifying a predetermined number of closest landmark of the analysis landmark set to that data point, identifying a node which includes a majority of the predetermined number of closest landmarks of the analysis landmark set as members, and adding that data point as a member of the node that includes a majority of the predetermined number of closest landmarks of the analysis landmark set as members. The method may further comprise generating a visualization of the plurality of nodes and edge.

In various embodiments, the method comprises determining the predetermined number of members of the expanded sub-subset of the expanded landmarks based on the constraints of the at least one of a plurality of computation devices or an analysis server. The method may also further comprise wherein the determination of the predetermined number of members of the expanded sub-subset of the expanded landmarks is based, at least in part, on a determination of a predetermined number of members of the analysis landmark set. Selecting, by the associated computation device, the group of data points from the subset of data points to generate the first sub-subset of landmarks may be performed randomly.

An example non-transitory computer readable medium may comprise instructions executable by a processor to perform a method, the method comprising: receiving a large number of data points, determining at least one size of a plurality of subsets of the large number of data points based on constraints of at least one of a plurality of computation devices or an analysis server, each data point of the large number of data points being a member of at least one of the plurality of subsets of the large number of data points, transferring each of the plurality of subsets of large number of data points to a respective one of the plurality of computation devices, each of the plurality of subsets of data points by an associated computation device of the plurality of computation devices being configured to: select, by the associated computation device, a group of data points from the subset of data points to generate a first sub-subset of landmarks, add, by the associated computation device, a non-landmark data point of the subset of data points to the first sub-subset of landmarks to create an expanded sub-subset of landmarks, add the non-landmark data points, the adding the non-landmark data points comprising calculating first data point distances between each non-landmark data point and each landmark, identifying a shortest data point distance from among the first data point distances for each non-landmark data point, identifying a particular non-landmark data point with a longest first landmark distance of all the shortest data path distances, and adding the particular non-landmark data point to the first sub-subset of landmarks to expand the first sub-subset of landmarks to generate an expanded set of landmarks, until the expanded sub-subset of the expanded landmarks reaches a predetermined number of members, repeat adding the non-landmark data points, creating an analysis landmark set based on a combination of expanded sub-subsets of expanded landmarks, performing a similarity function on the analysis landmark set to map landmark points of the analysis landmark set to a mathematical reference space, generating a cover of the mathematical reference space to divide the mathematical reference space into overlapping subsets, clustering the mapped landmark points of the analysis landmark set based on the overlapping subsets of the cover in the mathematical reference space, creating a plurality of nodes, each of the plurality of nodes being based on the clustering of the mapped landmark points of the analysis landmark set, each landmark point of the analysis landmark set being a member of at least one node, and connecting at least two of the plurality of nodes with an edge if the at least two of the plurality of nodes share at least one landmark point of the analysis landmark set as a member.

An example system includes memory and a processor, the memory may include instructions to configure the processor to receive a large number of data points, determine at least one size of a plurality of subsets of the large number of data points based on constraints of at least one of a plurality of computation devices or an analysis server, each data point of the large number of data points being a member of at least one of the plurality of subsets of the large number of data points, transfer each of the plurality of subsets of large number of data points to a respective one of the plurality of computation devices to enable for each of the plurality of subsets of data points by an associated computation device of the plurality of computation devices: select, by the associated computation device, a group of data points from the subset of data points to generate a first sub-subset of landmarks, add, by the associated computation device, a non-landmark data point of the subset of data points to the first sub-subset of landmarks to create an expanded sub-subset of landmarks, adding the non-landmark data points comprising: calculate first data point distances between each non-landmark data point and each landmark, identify a shortest data point distance from among the first data point distances for each non-landmark data point, identify a particular non-landmark data point with a longest first landmark distance of all the shortest data path distances, and add the particular non-landmark data point to the first sub-subset of landmarks to expand the first sub-subset of landmarks to generate an expanded set of landmarks until the expanded sub-subset of the expanded landmarks reaches a predetermined number of members, repeat adding the non-landmark data points, create an analysis landmark set based on a combination of expanded sub-subsets of expanded landmarks, perform a similarity function on the analysis landmark set to map landmark points of the analysis landmark set to a mathematical reference space, generate a cover of the mathematical reference space to divide the mathematical reference space into overlapping subsets, cluster the mapped landmark points of the analysis landmark set based on the overlapping subsets of the cover in the mathematical reference space, create a plurality of nodes, each of the plurality of nodes being based on the clustering of the mapped landmark points of the analysis landmark set, each landmark point of the analysis landmark set being a member of at least one node, and connect at least two of the plurality of nodes with an edge if the at least two of the plurality of nodes share at least one landmark point of the analysis landmark set as a member.

BRIEF DESCRIPTION OF THE DRAWINGS

FIG. 13 is an example data structure including biological data for a number of patients that may be used to generate the cancer map visualization in some embodiments.

DETAILED DESCRIPTION OF DRAWINGS

Some embodiments described herein may be a part of the subject of Topological Data Analysis (TDA). TDA is an area of research which has produced methods for studying point cloud data sets from a geometric point of view. Other data analysis techniques use "approximation by models" of various types. Examples of other data analysis techniques include regression methods which model data as a graph of a function in one or more variables. Unfortunately, certain qualitative properties (which one can readily observe when the data is two-dimensional) may be of a great deal of importance for understanding, and these features may not be readily represented within such models.

Figure 1A:
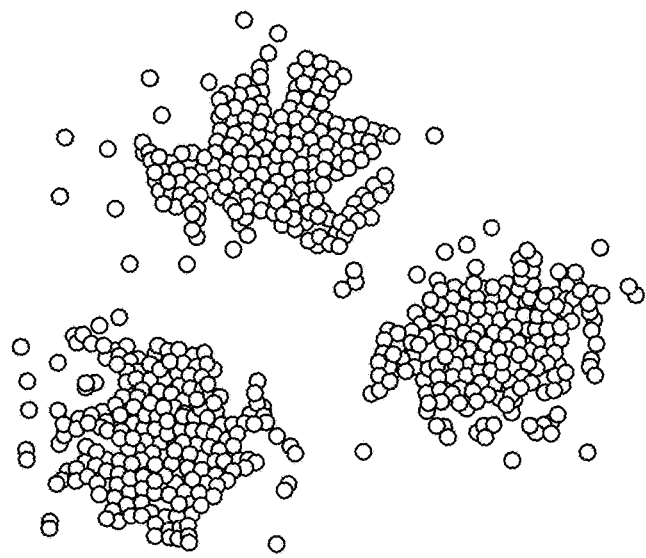
FIG. 1A is an example graph representing data that appears to be divided into three disconnected groups.

FIG. 1A is an example graph representing data that appears to be divided into three disconnected groups. In this example, the data for this graph may be associated with various physical characteristics related to different population groups or biomedical data related to different forms of a disease. Seeing that the data breaks into groups in this fashion can give insight into the data, once one understands what characterizes the groups.

Figure 1B:
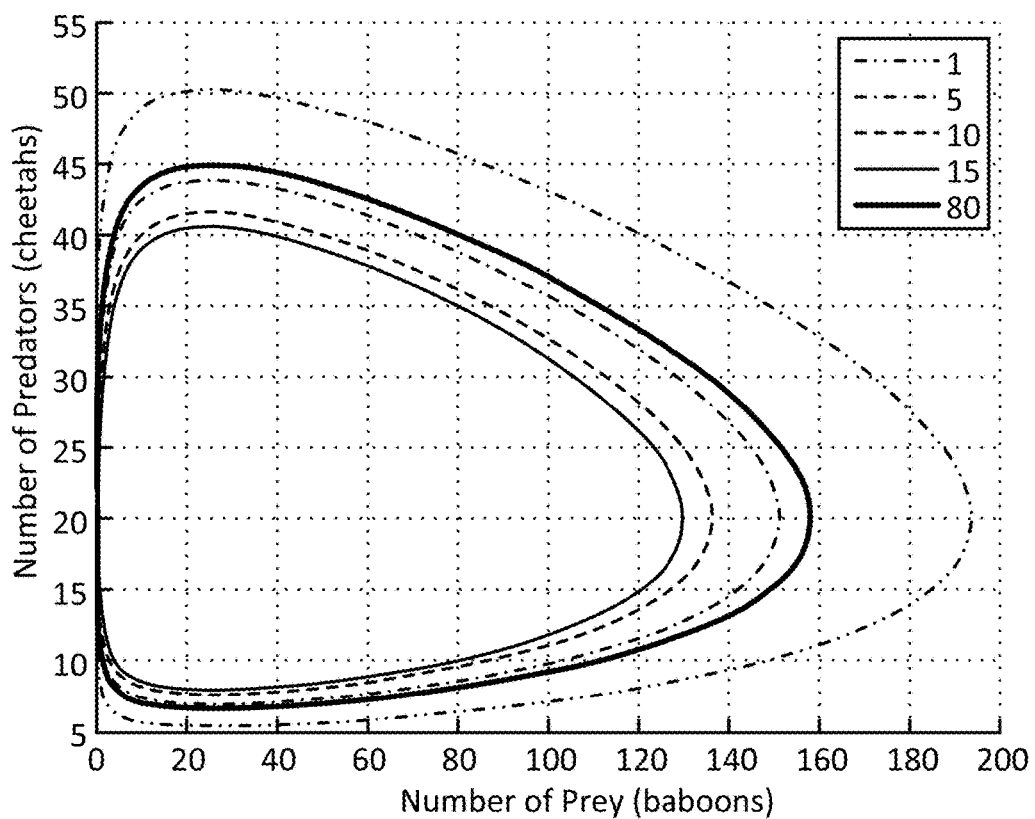
FIG. 1B is an example graph representing data set obtained from a Lotka-Volterra equation modeling the populations of predators and prey over time.

FIG. 1B is an example graph representing data set obtained from a Lotka-Volterra equation modeling the populations of predators and prey over time. From FIG. 1B, one observation about this data is that it is arranged in a loop. The loop is not exactly circular, but it is topologically a circle. The exact form of the equations, while interesting, may not be of as much importance as this qualitative observation which reflects the fact that the underlying phenomenon is recurrent or periodic. When looking for periodic or recurrent phenomena, methods may be developed which can detect the presence of loops without defining explicit models. For example, periodicity may be detectable without having to first develop a fully accurate model of the dynamics.

Figure 1C:
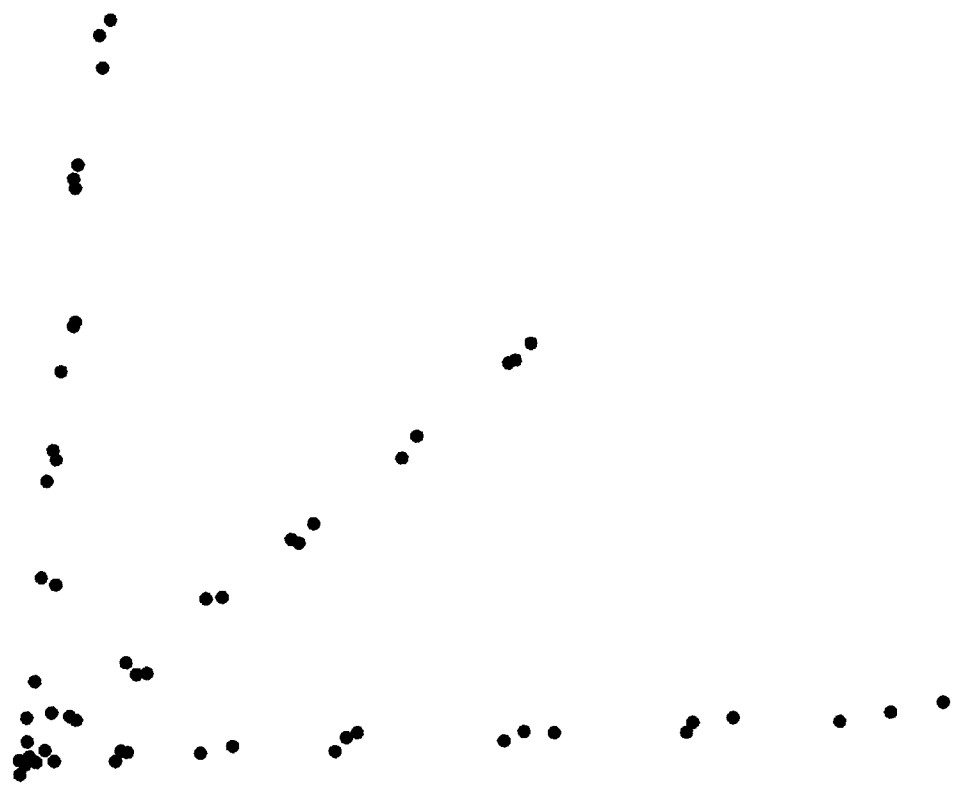
FIG. 1C is an example graph of data sets whereby the data does not break up into disconnected groups, but instead has a structure in which there are lines (or flares) emanating from a central group.

FIG. 1C is an example graph of data sets whereby the data does not break up into disconnected groups, but instead has a structure in which there are lines (or flares) emanating from a central group. In this case, the data also suggests the presence of three distinct groups, but the connectedness of the data does not reflect this. This particular data that is the basis for the example graph in FIG. 1C arises from a study of single nucleotide polymorphisms (SNPs).

In each of the examples above, aspects of the shape of the data are relevant in reflecting information about the data. Connectedness (the simplest property of shape) reflects the presence of a discrete classification of the data into disparate groups. The presence of loops, another simple aspect of shape, often reflect periodic or recurrent behavior. Finally, in the third example, the shape containing flares suggests a classification of the data descriptive of ways in which phenomena can deviate from the norm, which would typically be represented by the central core. These examples support the idea that the shape of data (suitably defined) is an important aspect of its structure, and that it is therefore important to develop methods for analyzing and understanding its shape. The part of mathematics which concerns itself with the study of shape is called topology, and topological data analysis attempts to adapt methods for studying shape which have been developed in pure mathematics to the study of the shape of data, suitably defined.

One question is how notions of geometry or shape are translated into information about point clouds, which are, after all, finite sets? What we mean by shape or geometry can come from a dissimilarity function or metric (e.g., a non-negative, symmetric, real-valued function d on the set of pairs of points in the data set which may also satisfy the triangle inequality, and $d(x; y)=0$ if and only if $x=y$). Such functions exist in profusion for many data sets. For example, when data comes in the form of a numerical matrix, where the rows correspond to the data points and the columns are the fields describing the data, the n-dimensional Euclidean distance function is natural when there are n fields. Similarly, in this example, there are Pearson correlation distances, cosine distances, and other choices.

When the data is not Euclidean, for example if one is considering genomic sequences, various notions of distance may be defined using measures of similarity based on Basic Local Alignment Search Tool (BLAST) type similarity scores. Further, a measure of similarity can come in non-numeric forms, such as social networks of friends or similarities of hobbies, buying patterns, tweeting, and/or professional interests. In any of these ways the notion of shape may be formulated via the establishment of a useful notion of similarity of data points.

One of the advantages of TDA is that TDA may depend on nothing more than such a notion, which is a very primitive or low-level model. TDA may rely on many fewer assumptions than standard linear or algebraic models, for example. Further, the methodology may provide new ways of visualizing and compressing data sets, which facilitate understanding and monitoring data. The methodology may enable study of interrelationships among disparate data sets and/or multiscale/multiresolution study of data sets. Moreover, the methodology may enable interactivity in the analysis of data, using point and click methods.

In some embodiments, TDA may be a very useful complement to more traditional methods, such as Principal Component Analysis (PCA), multidimensional scaling, and hierarchical clustering. These existing methods are often quite useful, but suffer from significant limitations. PCA, for example, is an essentially linear procedure and there are therefore limits to its utility in highly non-linear situations. Multidimensional scaling is a method which is not intrinsically linear, but can in many situations wash out detail, since it may overweight large distances. In addition, when metrics do not satisfy an intrinsic flatness condition, it may have difficulty in faithfully representing the data. Hierarchical clustering does exhibit multiscale behavior, but represents data only as disjoint clusters, rather than retaining any of the geometry of the data set. In all four cases, these limitations matter for many varied kinds of data.

We now summarize example properties of an example construction, in some embodiments, which may be used for representing the shape of data sets in a useful, understandable fashion as a finite graph:

The input may be a collection of data points equipped in some way with a distance or dissimilarity function, or other description. This can be given implicitly when the data is in the form of a matrix, or explicitly as a matrix of distances or even the generating edges of a mathematical network.

One construction may also use one or more lens functions (i.e. real valued functions on the data). Lens function(s) may depend directly on the metric. For example, lens function(s) might be the result of a density estimator or a measure of centrality or data depth. Lens function(s) may, in some embodiments, depend on a particular representation of the data, as when one uses the first one or two coordinates of a principal component or multidimensional scaling analysis. In some embodiments, the lens function(s) may be columns which expert knowledge identifies as being intrinsically interesting, as in cholesterol levels and BMI in a study of heart disease.

In some embodiments, the construction may depend on a choice of two or more processing parameters, resolution, and gain. Increase in resolution typically results in more nodes and an increase in the gain increases the number of edges in a visualization and/or graph in a reference space as further described herein.

The output may be, for example, a visualization (e.g., a display of connected nodes or "network") or simplicial complex. One specific combinatorial formulation in one embodiment may be that the vertices form a finite set, and then the additional structure may be a collection of edges (unordered pairs of vertices) which are pictured as connections in this network.

In various embodiments, a system for handling, analyzing, and visualizing data using drag and drop methods as opposed to text based methods is described herein. Philosophically, data analytic tools are not necessarily regarded as "solvers," but rather as tools for interacting with data. For example, data analysis may consist of several iterations of a process in which computational tools point to regions of interest in a data set. The data set may then be examined by people with domain expertise concerning the data, and the data set may then be subjected to further computational analysis. In some embodiments, methods described herein provide for going back and forth between mathematical constructs, including interactive visualizations (e.g., graphs), on the one hand and data on the other.

In one example of data analysis in some embodiments described herein, an exemplary clustering tool is discussed which may be more powerful than existing technology, in that one can find structure within clusters and study how clusters change over a period of time or over a change of scale or resolution.

An example interactive visualization tool (e.g., a visualization module which is further described herein) may produce combinatorial output in the form of a graph which can be readily visualized. In some embodiments, the example interactive visualization tool may be less sensitive to changes in notions of distance than current methods, such as multidimensional scaling.

Some embodiments described herein permit manipulation of the data from a visualization. For example, portions of the data which are deemed to be interesting from the visualization can be selected and converted into database objects, which can then be further analyzed. Some embodiments described herein permit the location of data points of interest within the visualization, so that the connection between a given visualization and the information the visualization represents may be readily understood.

Figure 2:
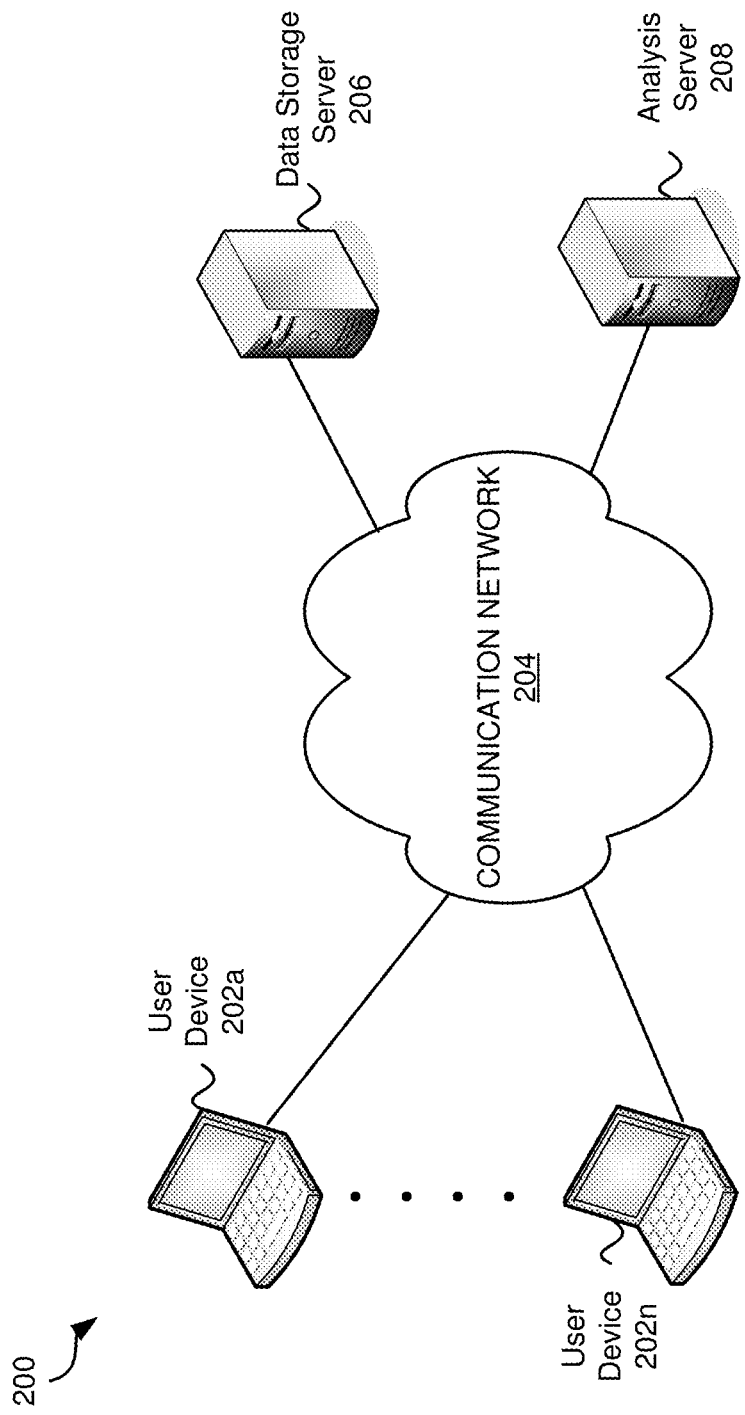
FIG. 2 is an example environment in which embodiments may be practiced.

FIG. 2 is an example environment 200 in which embodiments may be practiced. In various embodiments, data analysis and interactive visualization may be performed locally (e.g., with software and/or hardware on a local digital device), across a network (e.g., via cloud computing), or a combination of both. In many of these embodiments, a data structure is accessed to obtain the data for the analysis, the analysis is performed based on properties and parameters selected by a user, and an interactive visualization is generated and displayed. There are many advantages between performing all or some activities locally and many advantages of performing all or some activities over a network.

Environment 200 comprises user devices 202a-202n, a communication network 204, data storage server 206, and analysis server 208. Environment 200 depicts an embodiment wherein functions are performed across a network. In this example, the user(s) may take advantage of cloud computing by storing data in a data storage server 206 over a communication network 204. The analysis server 208 may perform analysis and generation of an interactive visualization.

User devices 202a-202n may be any digital devices. A digital device is any device that includes memory and a processor. Digital devices are further described in FIG. 18. The user devices 202a-202n may be any kind of digital device that may be used to access, analyze and/or view data including, but not limited to a desktop computer, laptop, notebook, or other computing device.

In various embodiments, a user, such as a data analyst, may generate and/or receive a database or other data structure with the user device 202a to be saved to the data storage server 206. The user device 202a may communicate with the analysis server 208 via the communication network 204 to perform analysis, examination, and visualization of data within the database.

The user device 202a may comprise any number of client programs. One or more of the client programs may interact with one or more applications on the analysis server 208. In other embodiments, the user device 202a may communicate with the analysis server 208 using a browser or other standard program. In various embodiments, the user device 202a communicates with the analysis server 208 via a virtual private network. Those skilled in the art will appreciate that that communication between the user device 202a, the data storage server 206, and/or the analysis server 208 may be encrypted or otherwise secured.

The communication network 204 may be any network that allows digital devices to communicate. The communication network 204 may be the Internet and/or include LAN and WANs. The communication network 204 may support wireless and/or wired communication.

The data storage server 206 is a digital device that is configured to store data. In various embodiments, the data storage server 206 stores databases and/or other data structures. The data storage server 206 may be a single server or a combination of servers. In one example the data storage server 206 may be a secure server wherein a user may store data over a secured connection (e.g., via https). The data may be encrypted and backed-up. In some embodiments, the data storage server 206 is operated by a third-party such as Amazon's S3 service.

The database or other data structure may comprise large high-dimensional datasets. These datasets are traditionally very difficult to analyze and, as a result, relationships within the data may not be identifiable using previous methods. Further, previous methods may be computationally inefficient.

The analysis server 208 may include any number of digital devices configured to analyze data (e.g., the data in the stored database and/or other dataset received and/or generated by the user device 202a). Although only one digital device is depicted in FIG. 2 corresponding to the analysis server 208, it will be appreciated that any number of functions of the analysis server 208 may be performed by any number of digital devices.

In various embodiments, the analysis server 208 may perform many functions to interpret, examine, analyze, and display data and/or relationships within data. In some embodiments, the analysis server 208 performs, at least in part, topological analysis of large datasets applying metrics, filters, and resolution parameters chosen by the user. The analysis is further discussed regarding FIG. 8 herein.

The analysis server 208 may generate graphs in memory, visualized graphs, and/or an interactive visualization of the output of the analysis. The interactive visualization allows the user to observe and explore relationships in the data. In various embodiments, the interactive visualization allows the user to select nodes comprising data that has been clustered. The user may then access the underlying data, perform further analysis (e.g., statistical analysis) on the underlying data, and manually reorient the graph(s) (e.g., structures of nodes and edges described herein) within the interactive visualization. The analysis server 208 may also allow for the user to interact with the data, see the graphic result. The interactive visualization is further discussed in FIGS. 9-11.

The graphs in memory and/or visualized graphs may also include nodes and/or edges as described herein. Graphs that are generated in memory may not be depicted to a user but rather may be in memory of a digital device. Visualized graphs are rendered graphs that may be depicted to the user (e.g., using user device 202a).

In some embodiments, the analysis server 208 interacts with the user device(s) 202a-202n over a private and/or secure communication network. The user device 202a may include a client program that allows the user to interact with the data storage server 206, the analysis server 208, another user device (e.g., user device 202n), a database, and/or an analysis application executed on the analysis server 208.

It will be appreciated that all or part of the data analysis may occur at the user device 202a. Further, all or part of the interaction with the visualization (e.g., graphic) may be performed on the user device 202a. Alternately, all or part of the data analysis may occur on any number of digital devices including, for example, on the analysis server 208.

Although two user devices 202a and 202n are depicted, those skilled in the art will appreciate that there may be any number of user devices in any location (e.g., remote from each other). Similarly, there may be any number of communication networks, data storage servers, and analysis servers.

Cloud computing may allow for greater access to large datasets (e.g., via a commercial storage service) over a faster connection. Further, those skilled in the art will appreciate that services and computing resources offered to the users) may be scalable.

Figure 3:
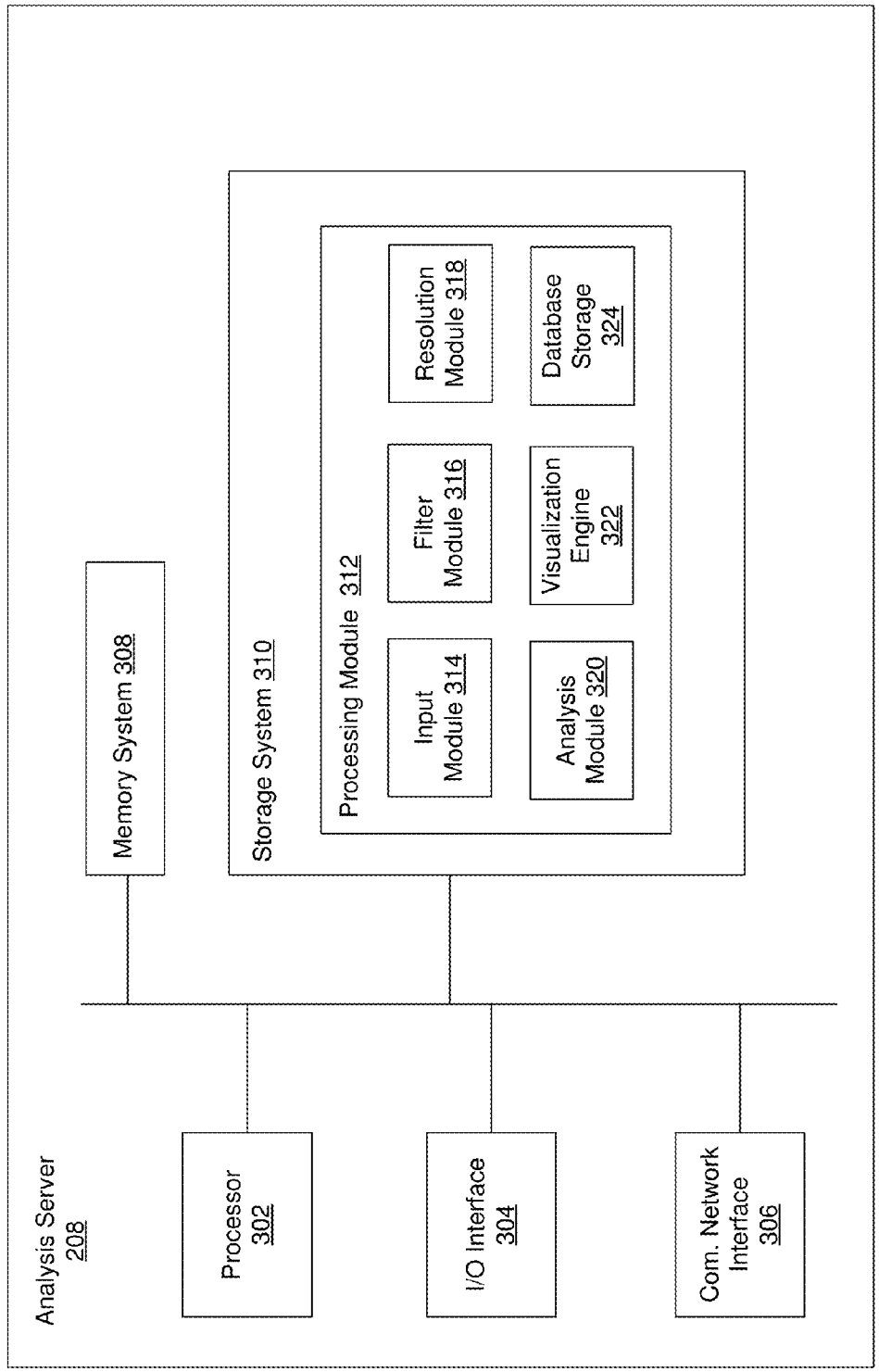
FIG. 3 is a block diagram of an example analysis server.

FIG. 3 is a block diagram of an example analysis server 208. In some embodiments the analysis server 208 comprises a processor 302, input/output (I/O) interface 304, a communication network interface 306, a memory system 308, a storage system 310, and a processing module 312. The processor 302 may comprise any processor or combination of processors with one or more cores.

The input/output (I/O) interface 304 may comprise interfaces for various I/O devices such as, for example, a keyboard, mouse, and display device. The example communication network interface 306 is configured to allow the analysis server 208 to communication with the communication network 204 (see FIG. 2). The communication network interface 306 may support communication over an Ethernet connection, a serial connection, a parallel connection, and/or an ATA connection. The communication network interface 306 may also support wireless communication (e.g., 802.11 a/b/g/n, WiMax, LTE, WiFi). It will be apparent to those skilled in the art that the communication network interface 306 can support many wired and wireless standards.

The memory system 308 may be any kind of memory including RAM, ROM, or flash, cache, virtual memory, etc. In various embodiments, working data is stored within the memory system 308. The data within the memory system 308 may be cleared or ultimately transferred to the storage system 310.

The storage system 310 includes any storage configured to retrieve and store data. Some examples of the storage system 310 include flash drives, hard drives, optical drives, and/or magnetic tape. Each of the memory system 308 and the storage system 310 comprises a non-transitory computer-readable medium, which stores instructions (e.g., software programs) executable by processor 302.

The storage system 310 comprises a plurality of modules utilized by embodiments of discussed herein. A module may be hardware, software e.g., including instructions executable by a processor), or a combination of both. In one embodiment, the storage system 310 includes a processing module 312. The processing module 312 may include memory and/or hardware and includes an input module 314, a filter module 316, a resolution module 318, an analysis module 320, a visualization engine 322, and database storage 324. Alternative embodiments of the analysis server 208 and/or the storage system 310 may comprise more, less, or functionally equivalent components and modules.

The input module 314 may be configured to receive commands and preferences from the user device 202a. In various examples, the input module 314 receives selections from the user which will be used to perform the analysis. The output of the analysis may be an interactive visualization.

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multidimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, those skilled in the art will appreciate that any window, graphical user interface, and/or command line may be used to receive or prompt a user or user device 202a for information.

The filter module 316 may subsequently provide the user with an interface window to allow the user to select a metric to be used in analysis of the data within the chosen data fields. The filter module 316 may also allow the user to select and/or define one or more filters.

The resolution module 318 may allow the user to select a resolution, including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. Those skilled in the art will appreciate that the analysis module 320 may use parallel algorithms or use generalizations of various statistical techniques (e.g., generalizing the bootstrap to zig-zag methods) to increase the size of data sets that can be processed. The analysis is further discussed herein (e.g., see discussion regarding FIG. 8). It will be appreciated that the analysis module 320 is not limited to algebraic topological analysis but may perform any analysis.

The visualization engine 322 generates an interactive visualization based on the output from the analysis module 320. The interactive visualization allows the user to see all or part of the analysis graphically. The interactive visualization also allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described herein (e.g., see discussion regarding FIGS. 9-11).

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

Those skilled in the art will appreciate that that all or part of the processing module 312 may be at the user device 202a or the database storage server 206. In some embodiments, all or some of the functionality of the processing module 312 may be performed by the user device 202a.

In various embodiments, systems and methods discussed herein may be implemented with one or more digital devices. In some examples, some embodiments discussed herein may be implemented by a computer program (instructions) executed by a processor. The computer program may provide a graphical user interface. Although such a computer program is discussed, those skilled in the art will appreciate that embodiments may be performed using any of the following, either alone or in combination, including, but not limited to, a computer program, multiple computer programs, firmware, and/or hardware.

A module and/or engine may include any processor or combination of processors. In some examples, a module and/or engine may include or be a part of a processor, digital signal processor (DSP), application specific integrated circuit (ASIC), an integrated circuit, and/or the like. In various embodiments, the module and/or engine may be software or firmware.

Figure 4:
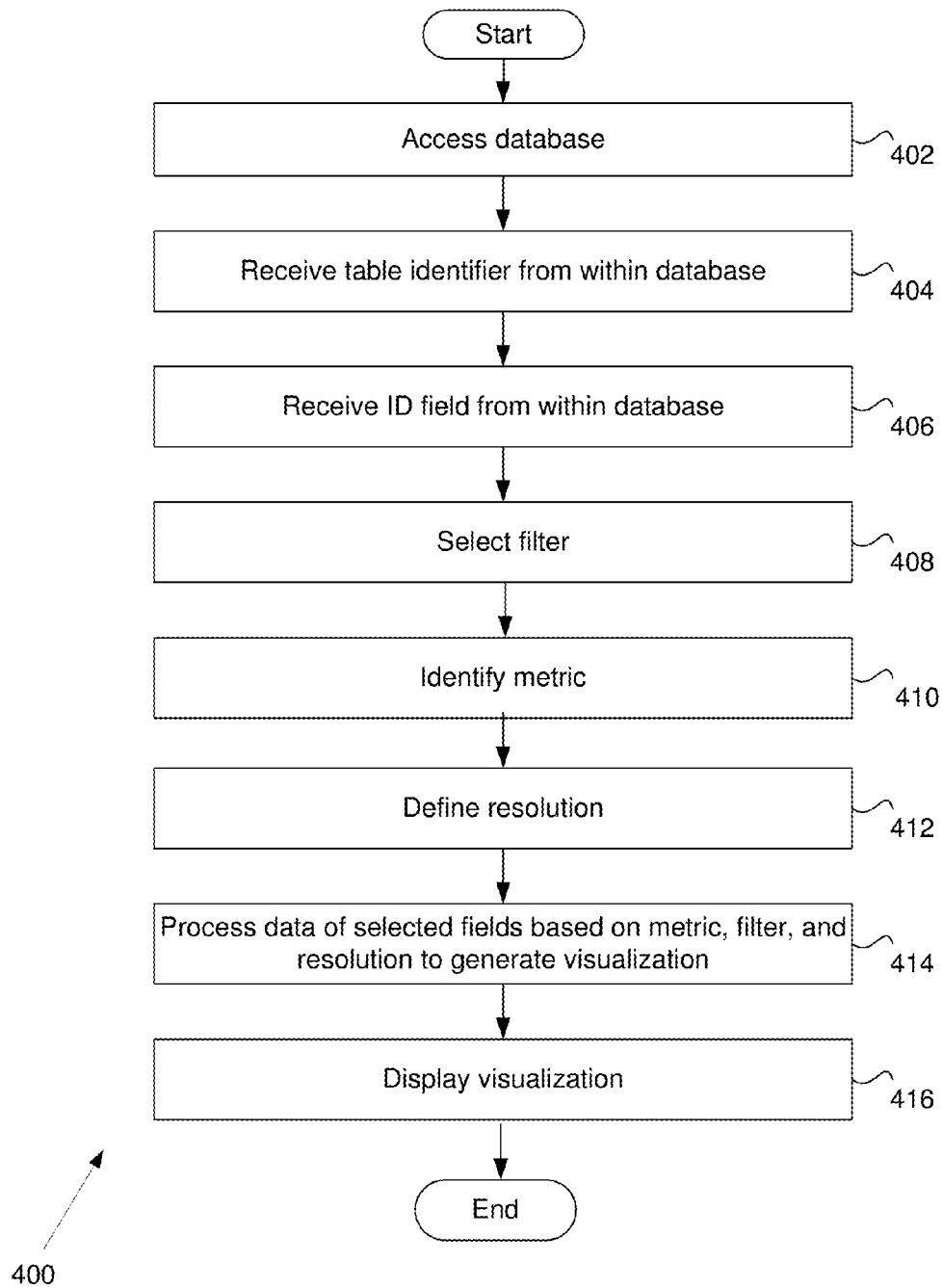
FIG. 4 is a flow chart, depicting an example method of dataset analysis and visualization in some embodiments.

FIG. 4 is a flow chart 400 depicting an example method of dataset analysis and visualization in some embodiments. In step 402, the input module 314 accesses a database. The database may be any data structure containing data (e.g., a very large dataset of multidimensional data). In some embodiments, the database may be a relational database. In some examples, the relational database may be used with MySQL, Oracle, Microsoft SQL Server, Aster nCluster, Teradata, and/or Vertica. Those skilled in the art will appreciate that the database may not be a relational database.

In some embodiments, the input module 314 receives a database identifier and a location of the database (e.g., the data storage server 206) from the user device 202a (see FIG. 2). The input module 314 may then access the identified database. In various embodiments, the input module 314 may read data from many different sources, including, but not limited to MS Excel files, text files (e.g., delimited or CSV), Matlab .mat format, or any other file.

In some embodiments, the input module 314 receives an IP address or hostname of a server hosting the database, a username, password, and the database identifier. This information (herein referred to as "connection information") may be cached for later use. It will be appreciated that the database may be locally accessed and that all, some, or none of the connection information may be required. In one example, the user device 202a may have full access to the database stored locally on the user device 202a so the IP address is unnecessary. In another example, the user device 202a may already have loaded the database and the input module 314 merely begins by accessing the loaded database.

In various embodiments, the identified database stores data within tables. A table may have a "column specification" which stores the names of the columns and their data types. A "row" in a table, may be a tuple with one entry for each column of the correct type. In one example, a table to store employee records might have a column specification such as:
  employee_id primary key int (this may store the employee's ID as an integer, and uniquely identifies a row)
  age int
  gender char(1) (gender of the employee may be a single character either M or F)
  salary double (salary of an employee may be a floating point number)
  name varchar (name of the employee may be a variable-length string)

In this example, each employee corresponds to a row in this table. Further, the tables in this example relational database are organized into logical units called databases. An analogy to file systems is that databases can be thought of as folders and files as tables. Access to databases may be controlled by the database administrator by assigning a username/password pair to authenticate users.

Once the database is accessed, the input module 314 may allow the user to access a previously stored analysis or to begin a new analysis. If the user begins a new analysis, the input module 314 may provide the user device 202a with an interface window allowing the user to identify a table from within the database. In one example, the input module 314 provides a list of available tables from the identified database.

In step 404, the input module 314 receives a table identifier identifying a table from within the database. The input module 314 may then provide the user with a list of available ID fields from the table identifier. In step 406, the input module 314 receives the ID field identifier from the user and/or user device 202a. The ID field is, in some embodiments, the primary key.

Having selected the primary key, the input module 314 may generate a new interface window to allow the user to select data fields for analysis. In step 408, the input module 314 receives data field identifiers from the user device 202a. The data within the data fields may be later analyzed by the analysis module 320.

In step 408, the filter module 316 selects one or more filters. In some embodiments, the filter module 316 and/or the input module 314 generates an interface window allowing the user of the user device 202a options for a variety of different metrics and filter preferences. The interface window may be a drop down menu identifying a variety of distance metrics to be used in the analysis.

In some embodiments, the user selects and/or provides filter identifier(s) to the filter module 316. The role of the filters in the analysis is also further described herein. The filters, for example, may be user defined, geometric, or based on data which has been pre-processed. In some embodiments, the data based filters are numerical arrays which can assign a set of real numbers to each row in the table or each point in the data generally.

A variety of geometric filters may be available for the user to choose. Geometric filters may include, but are not limited to:
  Density
  L1 Eccentricity
  L-infinity Eccentricity
  Witness based Density
  Witness based Eccentricity
  Eccentricity as distance from a fixed point
  Approximate Kurtosis of the Eccentricity In step 410, the filter module 316 identifies a metric. Metric options may include, but are not limited to, Euclidean, DB Metric, variance normalized Euclidean, and total normalized Euclidean. The metric and the analysis are further described herein.

In step 412, the resolution module 318 defines the resolution to be used with a filter in the analysis. The resolution may comprise a number of intervals and an overlap parameter. In various embodiments, the resolution module 318 allows the user to adjust the number of intervals and overlap parameter (e.g., percentage overlap) for one or more filters.

In step 414, the analysis module 320 processes data of selected fields based on the metric, filter(s), and resolution(s)

to generate the visualization. This process is further discussed herein (e.g., see discussion regarding FIG. 8).

In step 416, the visualization engine 322 displays the interactive visualization. In various embodiments, the visualization may be rendered in two or three dimensional space. The visualization engine 322 may use an optimization algorithm for an objective function which is correlated with good visualization (e.g., the energy of the embedding). The visualization may show a collection of nodes corresponding to each of the partial clusters in the analysis output and edges connecting them as specified by the output. The interactive visualization is further discussed herein (e.g., see discussion regarding FIGS. 9-11).

Although many examples discuss the input module 314 as providing interface windows, it will be appreciated that all or some of the interface may be provided by a client on the user device 202a. Further, in some embodiments, the user device 202a may be running all or some of the processing module 312.

Figure 5:
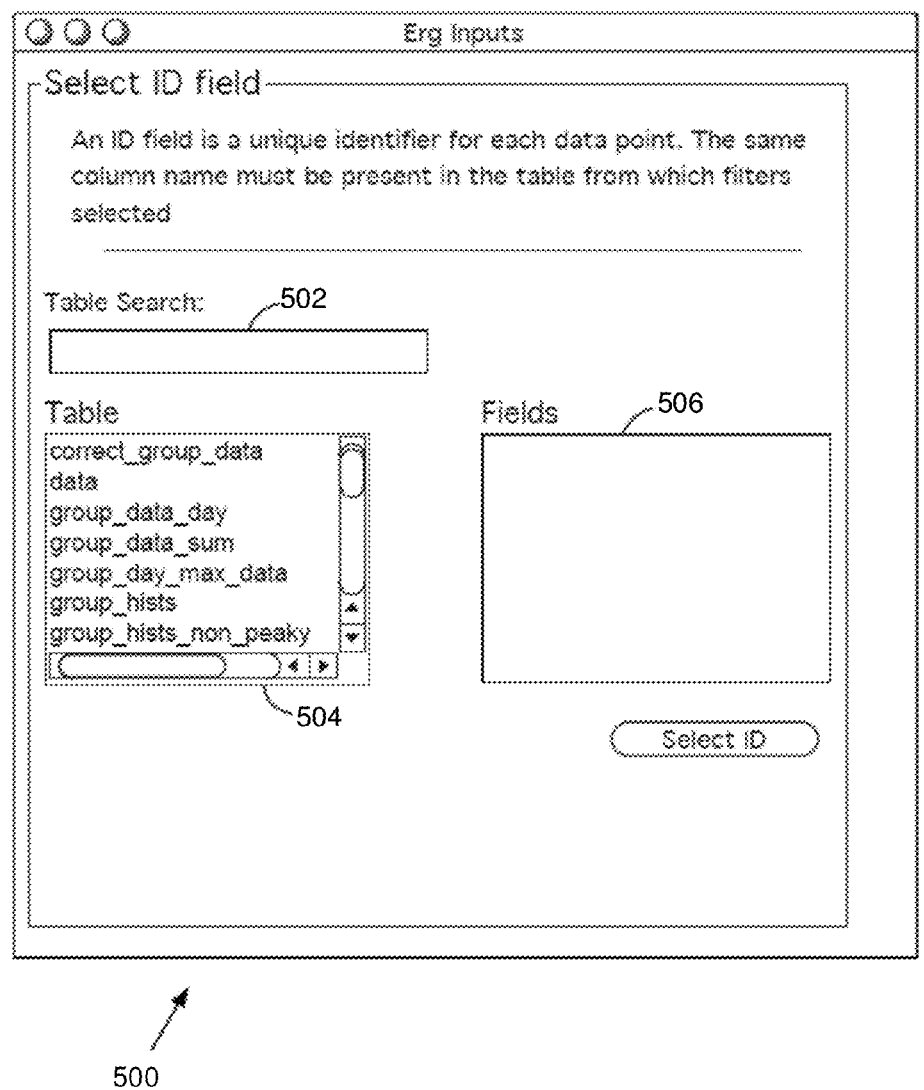
FIG. 5 is an example ID field selection interface window in some embodiments.
Figure 6A:
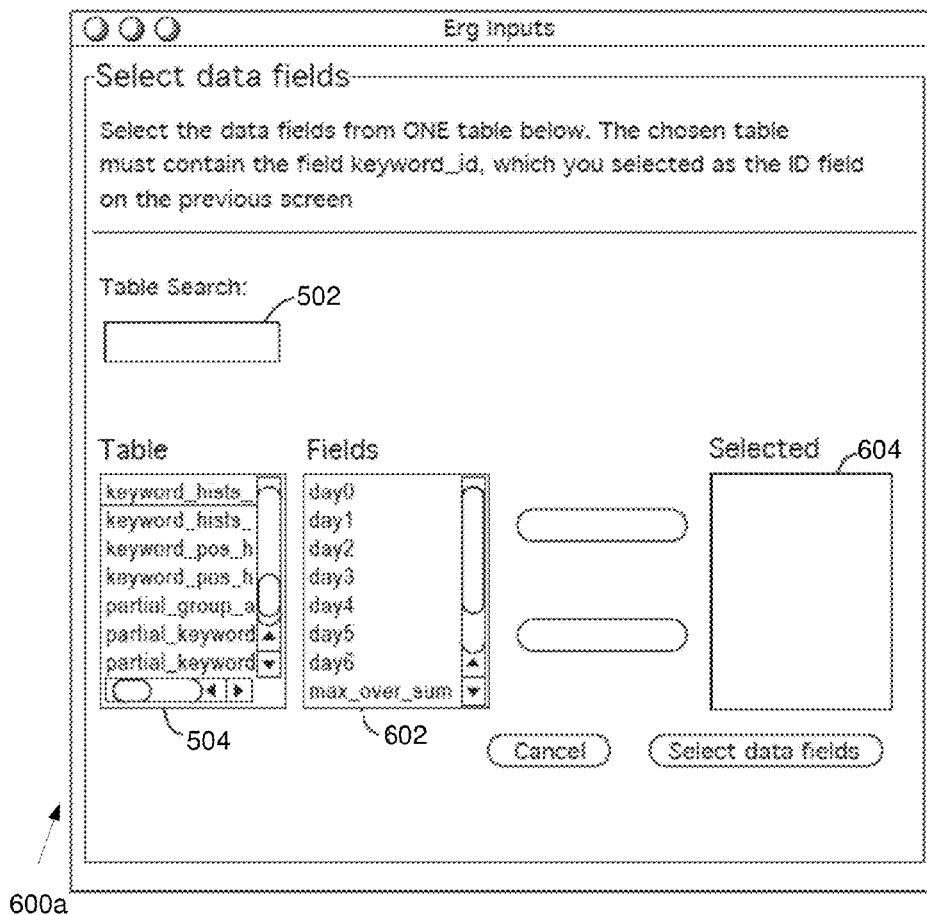
FIG. 6a is an example data field selection interface window in some embodiments.
Figure 6B:
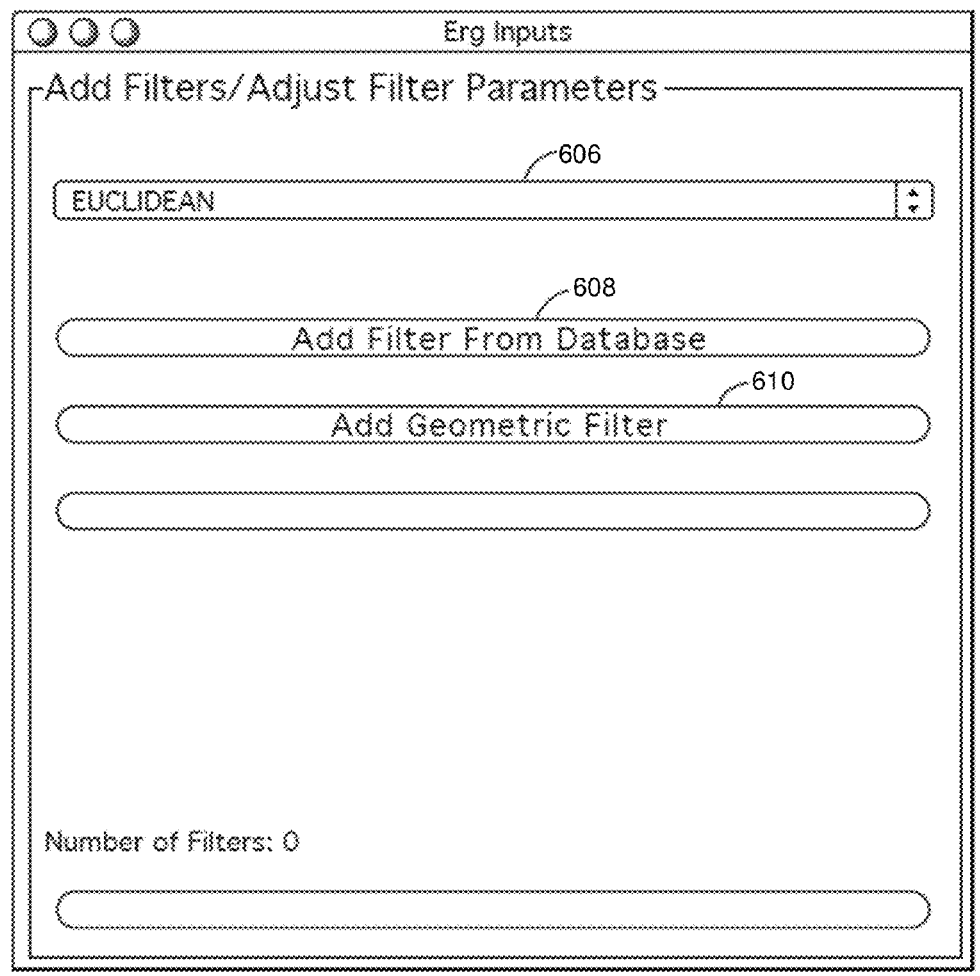
FIG. 6b is an example metric and filter selection interface window in some embodiments.
Figure 7:
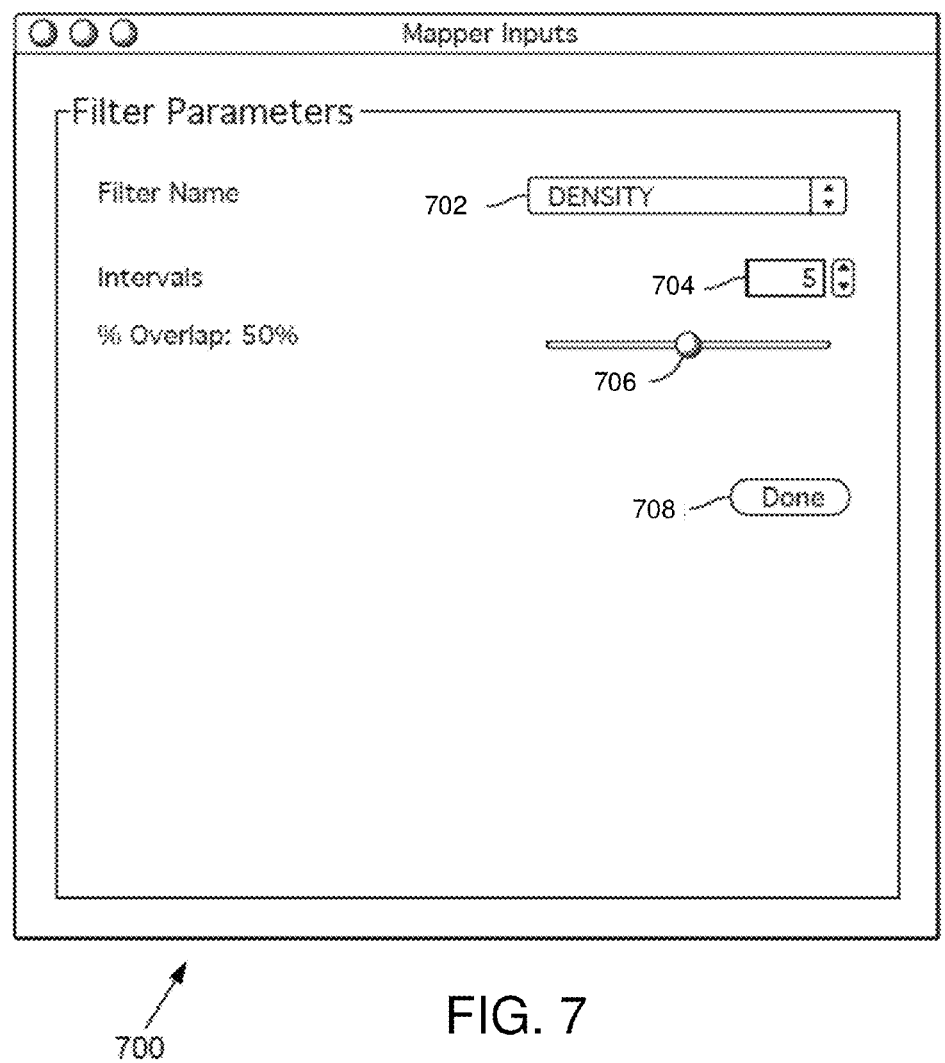
FIG. 7 is an example filter parameter interface window in some embodiments.

FIGS. 5-7 depict various interface windows to allow the user to make selections, enter information (e.g., fields, metrics, and filters), provide parameters (e.g., resolution), and provide data (e.g., identify the database) to be used with analysis. It will be appreciated that any graphical user interface or command line may be used to make selections, enter information, provide parameters, and provide data.

FIG. 5 is an exemplary ID field selection interface window 500 in some embodiments. The ID field selection interface window 500 allows the user to identify an ID field. The ID field selection interface window 500 comprises a table search field 502, a table list 504, and a fields selection window 506.

In various embodiments, the input module 314 identifies and accesses a database from the database storage 324, user device 202a, or the data storage server 206. The input module 314 may then generate the ID field selection interface window 500 and provide a list of available tables of the selected database in the table list 504. The user may click on a table or search for a table by entering a search query (e.g., a keyword) in the table search field 502. Once a table is identified (e.g., clicked on by the user), the fields selection window 506 may provide a list of available fields in the selected table. The user may then choose a field from the fields selection window 506 to be the ID field. In some embodiments, any number of fields may be chosen to be the ID field(s).

FIG. 6a is an example data field selection interface window 600a in some embodiments. The data field selection interface window 600a allows the user to identify data fields. The data field selection interface window 600a comprises a table search field 502, a table list 504, a fields selection window 602, and a selected window 604.

In various embodiments, after selection of the ID field, the input module 314 provides a list of available tables of the selected database in the table list 504. The user may click on a table or search for a table by entering a search query (e.g., a keyword) in the table search field 502. Once a table is identified (e.g., clicked on by the user), the fields selection window 506 may provide a list of available fields in the selected table. The user may then choose any number of fields from the fields selection window 602 to be data fields. The selected data fields may appear in the selected window 604. The user may also deselect fields that appear in the selected window 604.

Those skilled in the art will appreciate that the table selected by the user in the table list 504 may be the same table selected with regard to FIG. 5. In some embodiments, however, the user may select a different table. Further, the user may, in various embodiments, select fields from a variety of different tables.

FIG. 6b is an example metric and filter selection interface window 600b in some embodiments. The metric and filter selection interface window 600b allows the user to identify a metric, add filter(s), and adjust filter parameters. The metric and filter selection interface window 600b comprises a metric pull down menu 606, an add filter from database button 608, and an add geometric filter button 610.

In various embodiments, the user may click on the metric pull down menu 606 to view a variety of metric options. Various metric options are described herein. In some embodiments, the user may define a metric. The user defined metric may then be used with the analysis.

In one example, finite metric space data may be constructed from a data repository (i.e., database, spreadsheet, or Matlab file). This may mean selecting a collection of fields whose entries will specify the metric using the standard Euclidean metric for these fields, when they are floating point or integer variables. Other notions of distance, such as graph distance between collections of points, may be supported.

The analysis module 320 may perform analysis using the metric as a part of a distance function. The distance function can be expressed by a formula, a distance matrix, or other routine which computes it. The user may add a filter from a database by clicking on the add filter from database button 608. The metric space may arise from a relational database, a Matlab file, an Excel spreadsheet, or other methods for storing and manipulating data. The metric and filter selection interface window 600b may allow the user to browse for other filters to use in the analysis. The analysis and metric function are further described herein (e.g., see discussion regarding FIG. 8).

The user may also add a geometric filter 610 by clicking on the add geometric filter button 610. In various embodiments, the metric and filter selection interface window 600b may provide a list of geometric filters from which the user may choose.

FIG. 7 is an example filter parameter interface window 700 in some embodiments. The filter parameter interface window 700 allows the user to determine a resolution for one or more selected filters (e.g., filters selected in the metric and filter selection interface window 600). The filter parameter interface window 700 comprises a filter name menu 702, an interval field 704, an overlap bar 706, and a done button 708.

The filter parameter interface window 700 allows the user to select a filter from the filter name menu 702. In some embodiments, the filter name menu 702 is a drop down box indicating all filters selected by the user in the metric and filter selection interface window 600. Once a filter is chosen, the name of the filter may appear in the filter name menu 702. The user may then change the intervals and overlap for one, some, or all selected filters.

The interval field 704 allows the user to define a number of intervals for the filter identified in the filter name menu 702. The user may enter a number of intervals or scroll up or down to get to a desired number of intervals. Any number of intervals may be selected by the user. The function of the intervals is further discussed herein (e.g., see discussion regarding FIG. 8).

The overlap bar 706 allows the user to define the degree of overlap of the intervals for the filter identified in the filter name menu 702. In one example, the overlap bar 706 includes a slider that allows the user to define the percentage overlap for the interval to be used with the identified filter. Any percentage overlap may be set by the user.

Once the intervals and overlap are defined for the desired filters, the user may click the done button. The user may then go back to the metric and filter selection interface window 600 and see a new option to run the analysis. In some embodiments, the option to run the analysis may be available in the filter parameter interface window 700. Once the analysis is complete, the result may appear in an interactive visualization further described herein (e.g., see discussion regarding FIGS. 9-11).

It will be appreciated that interface windows in FIGS. 4-7 are examples. The example interface windows are not limited to the functional objects (e.g., buttons, pull down menus, scroll fields, and search fields) shown. Any number of different functional objects may be used. Further, as described herein, any other interface, command line, or graphical user interface may be used.

Figure 8:
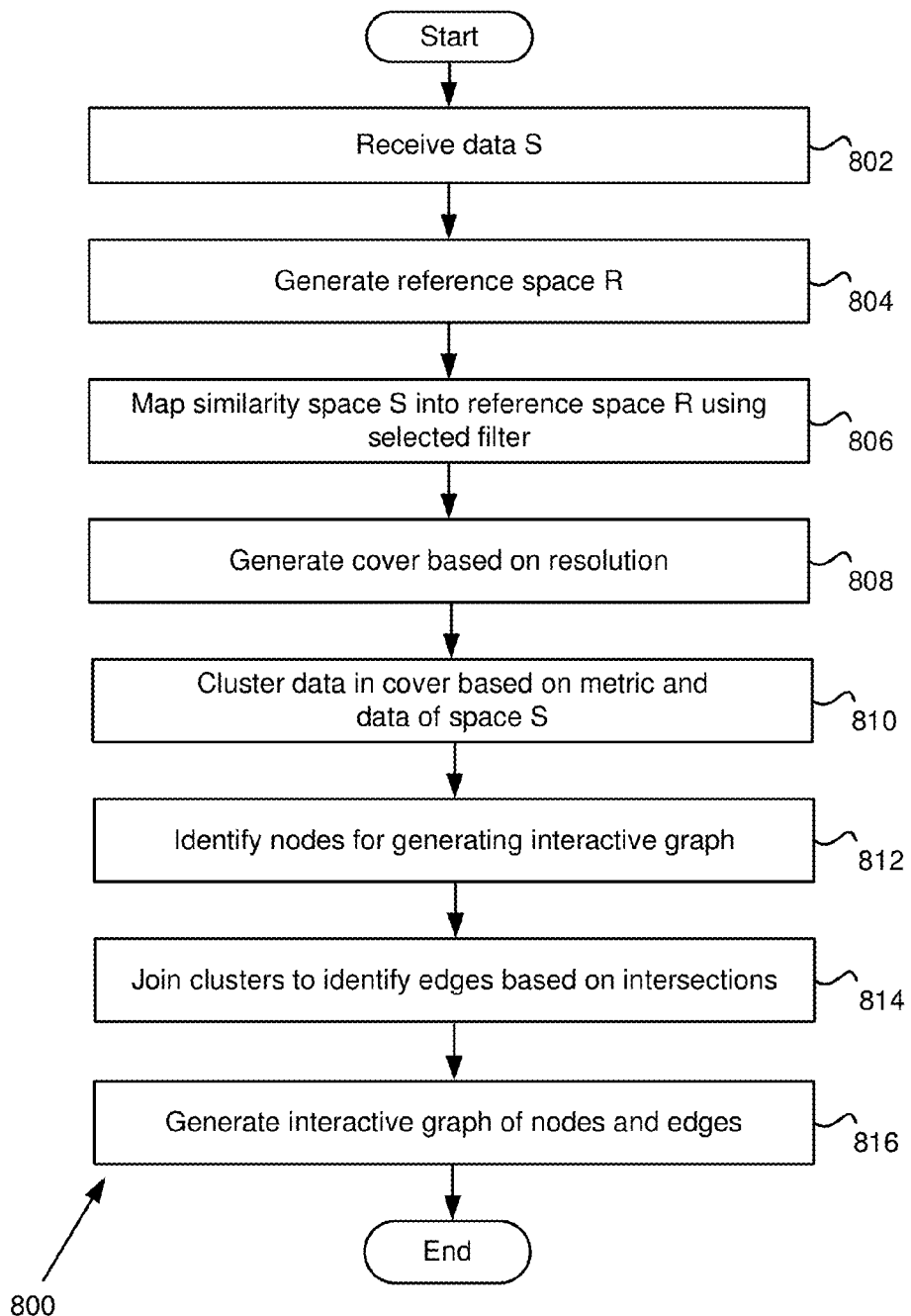
FIG. 8 is a flowchart for data analysis and generating a visualization in some embodiments.

FIG. 8 is a flowchart 800 for data analysis and generating an interactive visualization in some embodiments. In various embodiments, the processing on data and user-specified options is motivated by techniques from topology and, in some embodiments, algebraic topology. These techniques may be robust and general. In one example, these techniques apply to almost any kind of data for which some qualitative idea of "closeness" or "similarity" exists. The techniques discussed herein may be robust because the results may be relatively insensitive to noise in the data and even to errors in the specific details of the qualitative measure of similarity, which, in some embodiments, may be generally refer to as "the distance function" or "metric." It will be appreciated that while the description of the algorithms below may seem general, the implementation of techniques described herein may apply to any level of generality.

In step 802, the input module 314 receives data S. In one example, a user identifies a data structure and then identifies ID and data fields. Data S may be based on the information within the ID and data fields. In various embodiments, data S is treated as being processed as a finite "similarity space," where data. S has a real-valued function d defined on pairs of points s and t in S, such that:

$d(s,s)=0$ $d(s,t)=d(t,s)$ $d(s,t)>=0$

These conditions may be similar to requirements for a finite metric space, but the conditions may be weaker. In various examples, the function is a metric.

It will be appreciated that data S may be a finite metric space, or a generalization thereof, such as a graph or weighted graph. In some embodiments, data S be specified by a formula, an algorithm, or by a distance matrix which specifies explicitly every pairwise distance.

In step 804, the input module 314 generates reference space R. In one example, reference space R may be a well-known metric space (e.g., such as the real line). The reference space R may be defined by the user. In step 806, the analysis module 320 generates a map ref( ) from S into R. The map ref( ) from S into R may be called the "reference map."

In one example, a reference of map from S is to a reference metric space R. R may be Euclidean space of some dimension, but it may also be the circle, torus, a tree, or other metric space. The map can be described by one or more filters (i.e., real valued functions on S). These filters can be defined by geometric invariants, such as the output of a density estimator, a notion of data depth, or functions specified by the origin of S as arising from a data set.

In step 808, the resolution module 318 generates a cover of R based on the resolution received from the user (e.g., filter(s), intervals, and overlap—see discussion regarding FIG. 7 for example). The cover of R may be a finite collection of open sets (in the metric of R) such that every point in R lies in at least one of these sets. In various examples, R is k-dimensional Euclidean space, where k is the number of filter functions. More precisely in this example, R is a box in k-dimensional Euclidean space given by the product of the intervals [min_k, max_k], where min_k is the minimum value of the k-th filter function on 5, and max_k is the maximum value.

For example, suppose there are 2 filter functions, F1 and F2, and that F1's values range from −1 to +1, and F2's values range from 0 to 5. Then the reference space is the rectangle in the x/y plane with corners (−1,0), (1,0), (−1, 5), (1, 5), as every point s of S will give rise to a pair (F1(s), F2(s)) that lies within that rectangle.

In various embodiments, the cover of R is given by taking products of intervals of the covers of [min_k,max_k] for each of the k filters. In one example, if the user requests 2 intervals and a 50% overlap for F1, the cover of the interval [−1,+1] will be the two intervals (−1.5, 0.5), (−.5, 1.5). If the user requests 5 intervals and a 30% overlap for F2, then that cover of [0, 5] will be (−0.3, 1.3), (0.7, 2.3), (1.7, 3.3), (2.7, 4.3), (3.7, 5.3). These intervals may give rise to a cover of the 2-dimensional box by taking all possible pairs of intervals where the first of the pair is chosen from the cover for F1 and the second from the cover for F2. This may give rise to 2*5, or 10, open boxes that covered the 2-dimensional reference space. However, those skilled in the art will appreciate that the intervals may not be uniform, or that the covers of a k-dimensional box may not be constructed by products of intervals. In some embodiments, there are many other choices of intervals. Further, in various embodiments, a wide range of covers and/or more general reference spaces may be used.

In one example, given a cover, $C_1, \ldots, C_m$, of R, the reference map is used to assign a set of indices to each point in S, which are the indices of the $C_j$ such that ref(s) belongs to $C_j$. This function may be called ref_tags(s). In a language such as Java, ref_tags would be a method that returned an int[ ]. Since the C's cover R in this example, ref(s) must lie in at least one of them, but the elements of the cover usually overlap one another, which means that points that "land near the edges" may well reside in multiple cover sets. In considering the two filter example, if F1(s) is −0.99, and F2(s) is 0.001, then ref(s) is (−0.99, 0.001), and this lies in the cover element (−1.5, 0.5)×(−0.3,1.3). Supposing that was labeled $C_1$, the reference map may assign s to the set {1}. On the other hand, if t is mapped by F1, F2 to (0.1, 2.1), then ref(t) will be in (−1.5,0.5)×(0.7, 2.3), (−0.5, 1.5)×(0.7, 2.3), (−1.5,0.5)×(1.7,3.3), and (−0.5, 1.5)×(1.7,3.3), so the set of indices would have four elements for t.

Having computed, for each point, which "cover tags" it is assigned to, for each cover element, $C_d$, the points may be constructed, whose tags included, as set S(d). This may mean that every point s is in S(d) for some d, but some points may belong to more than one such set. In some embodiments, there is, however, no requirement that each S(d) is non-empty, and it is frequently the case that some of these sets are empty. In the non-parallelized version of some embodiments, each point x is processed in turn, and x is inserted into a hash-bucket for each j in ref_tags(t) (that is, this may be how S(d) sets are computed).

It will be appreciated that the cover of the reference space R may be controlled by the number of intervals and the overlap identified in the resolution (e.g., see further discussion regarding FIG. 7). For example, the more intervals, the finer the resolution in S—that is, the fewer points in each S(d), but the more similar (with respect to the filters) these points may be. The greater the overlap, the more times that clusters in S(d) may intersect clusters in S(e)—this means that more "relationships" between points may appear, but, in some embodiments, the greater the overlap, the more likely that accidental relationships may appear.

In step 810, the analysis module 320 clusters each S(d) based on the metric, filter, and the space S. In some embodiments, a dynamic single-linkage clustering algorithm may be used to partition S(d). It will be appreciated that any number of clustering algorithms may be used with embodiments discussed herein. For example, the clustering scheme may be k-means clustering for some k, single linkage clustering, average linkage clustering, or any method specified by the user.

The significance of the user-specified inputs may now be seen. In some embodiments, a filter may amount to a "forced stretching" in a certain direction. In some embodiments, the analysis module 320 may not cluster two points unless ALL of the filter values are sufficiently "related" (recall that while normally related may mean "close," the cover may impose a much more general relationship on the filter values, such as relating two points s and t if ref(s) and ref(t) are sufficiently close to the same circle in the plane). In various embodiments, the ability of a user to impose one or more "critical measures" makes this technique more powerful than regular clustering, and the fact that these filters can be anything, is what makes it so general.

The output may be a simplicial complex, from which one can extract its 1-skeleton. The nodes of the complex may be partial clusters, (i.e., clusters constructed from subsets of S specified as the preimages of sets in the given covering of the reference space R).

In step 812, the visualization engine 322 identifies nodes which are associated with a subset of the partition elements of all of the S(d) for generating an interactive visualization. For example, suppose that S={1, 2, 3, 4}, and the cover is $C_1, C_2, C_3$. Then if ref_tags(1)={1, 2, 3} and ref_tags(2)={2, 3}, and ref_tags(3)={3}, and finally ref_tags(4)=, {1, 3}, then S(1) in this example is {1, 4}, S(2)={1,2}, and S(3)={1,2,3,4}. If 1 and 2 are close enough to be clustered, and 3 and 4 are, but nothing else, then the clustering for S(1) may be {1} {3}, and for S(2) it may be {1,2}, and for S(3) it may be {1,2}, {3,4}. So the generated graph has, in this example, at most four nodes, given by the sets {1}, {4}, {1,2}, and {3,4} (note that {1,2} appears in two different clusterings). Of the sets of points that are used, two nodes intersect provided that the associated node sets have a non-empty intersection (although this could easily be modified to allow users to require that the intersection is "large enough" either in absolute or relative terms).

Nodes may be eliminated for any number of reasons. For example, a node may be eliminated as having too few points and/or not being connected to anything else. In some embodiments, the criteria for the elimination of nodes (if any) may be under user control or have application-specific requirements imposed on it. For example, if the points are consumers, for instance, clusters with too few people in area codes served by a company could be eliminated. If a cluster was found with "enough" customers, however, this might indicate that expansion into area codes of the other consumers in the cluster could be warranted.

In step 814, the visualization engine 322 joins clusters to identify edges (e.g., connecting lines between nodes). Once the nodes are constructed, the intersections (e.g., edges) may be computed "all at once," by computing, for each point, the set of node sets (not ref_tags, this time). That is, for each s in S, node_id_set(s) may be computed, which is an int[ ]. In some embodiments, if the cover is well behaved, then this operation is linear in the size of the set S, and we then iterate over each pair in node_id_set(s). There may be an edge between two node_id's if they both belong to the same node_id_set( ) value, and the number of points in the intersection is precisely the number of different node_id sets in which that pair is seen. This means that, except for the clustering step (which is often quadratic in the size of the sets S(d), but whose size may be controlled by the choice of cover), all of the other steps in the graph construction algorithm may be linear in the size of S, and may be computed quite efficiently.

Figure 9:
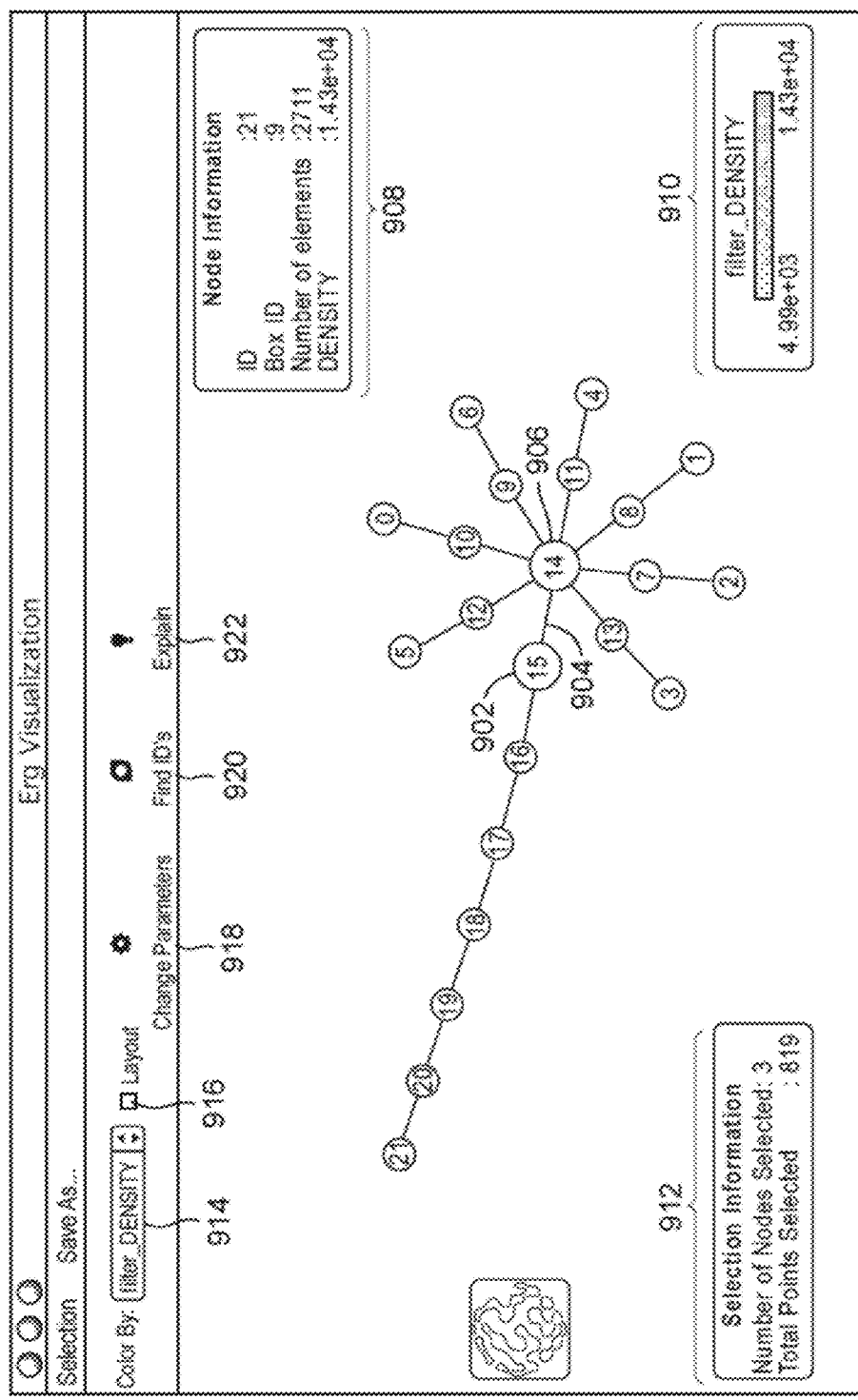
FIG. 9 is an example interactive visualization in some embodiments.
Figure 10:
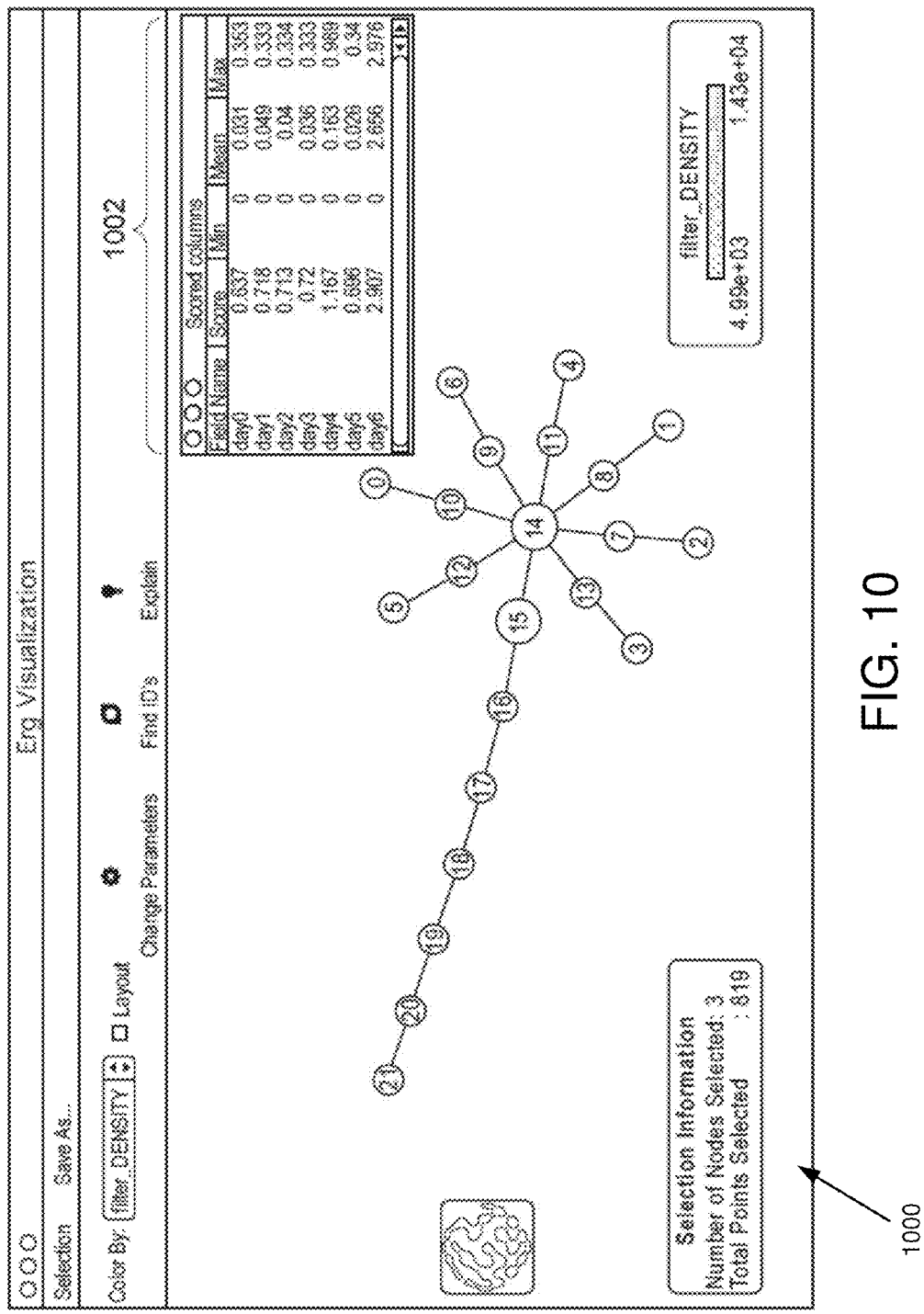
FIG. 10 is an example interactive visualization displaying an explain information window in some embodiments.

In step 816, the visualization engine 322 generates the interactive visualization of interconnected nodes (e.g., nodes and edges displayed in FIGS. 9 and 10).

It will be appreciated that it is possible, in some embodiments, to make sense in a fairly deep way of connections between various ref( ) maps and/or choices of clustering. Further, in addition to computing edges (pairs of nodes), the embodiments described herein may be extended to compute triples of nodes, etc. For example, the analysis module 320 may compute simplicial complexes of any dimension (by a variety of rules) on nodes, and apply techniques from homology theory to the graphs to help users understand a structure in an automatic (or semi-automatic) way.

Further, it will be appreciated that uniform intervals in the covering may not always be a good choice. For example, if the points are exponentially distributed with respect to a given filter, uniform intervals can fail—in such case adaptive interval sizing may yield uniformly-sized S(d) sets, for instance.

Further, in various embodiments, an interface may be used to encode techniques for incorporating third-party extensions to data access and display techniques. Further, an interface may be used to for third-party extensions to underlying infrastructure to allow for new methods for generating coverings, and defining new reference spaces.

FIG. 9 is an example interactive visualization 900 in some embodiments. The display of the interactive visualization may be considered a "graph" in the mathematical sense. The interactive visualization comprises of two types of objects: nodes (e.g., nodes 902 and 906) (which may be balls and may be colored) and the edges (e.g., edge 904) (the black lines). The edges connect pairs of nodes (e.g., edge 904 connects node 902 with node 906). As discussed herein, each node may represent a collection of data points (rows in the database identified by the user). In one example, connected nodes tend to include data points which are "similar to" (e.g., clustered with) each other. The collection of data points may be referred to as being "in the node." The interactive visualization may be two-dimensional, three-dimensional, or a combination of both.

In various embodiments, connected nodes and edges may form a graph or structure. There may be multiple graphs in the interactive visualization. In one example, the interactive visualization may display two or more unconnected structures of nodes and edges.

The visual properties of the nodes and edges (such as, but not limited to, color, stroke color, text, texture, shape, coordinates of the nodes on the screen) can encode any data based property of the data points within each node. For example, coloring of the nodes and/or the edges may indicate (but is not limited to) the following:

Values of fields or filters

Any general functions of the data in the nodes (e.g., if the data were unemployment rates by state, then GDP of the states may be identifiable by color the nodes)

Number of data points in the node

The interactive visualization 900 may contain a "bar" 910 which may comprise a legend indicating patterns and/or coloring of the nodes (e.g., balls) and may also identify what the patterns and/or colors indicate. For example, in FIG. 9, bar 910 may indicate that color of some nodes is based on the density filter with blue (on the far left of the bar 910) indicating "4.99e+03" and red (on the far right of the bar 910) indicating "1.43e+04." In general this might be expanded to show any other legend by which nodes and/or edges are colored. It will be appreciated that, in some embodiments, the user may control the color as well as what the color (and/or stroke color, text, texture, shape, coordinates of the nodes on the screen) indicates.

The user may also drag and drop objects of the interactive visualization 900. In various embodiments, the user may reorient structures of nodes and edges by dragging one or more nodes to another portion of the interactive visualization (e.g., a window). In one example, the user may select node 902, hold node 902, and drag the node across the window. The node 902 will follow the user's cursor, dragging the structure of edges and/or nodes either directly or indirectly connected to the node 902. In some embodiments, the interactive visualization 900 may depict multiple unconnected structures. Each structure may include nodes, however, none of the nodes of either structure are connected to each other. If the user selects and drags a node of the first structure, only the first structure will be reoriented with respect to the user action. The other structure will remain unchanged. The user may wish to reorient the structure in order to view nodes, select nodes, and/or better understand the relationships of the underlying data.

In one example, a user may drag a node to reorient the interactive visualization (e.g., reorient the structure of nodes and edges). While the user selects and/or drags the node, the nodes of the structure associated with the selected node may move apart from each other in order to provide greater visibility. Once the user lets go (e.g., deselects or drops the node that was dragged), the nodes of the structure may continue to move apart from each other.

In various embodiments, once the visualization engine 322 generates the interactive display, the depicted structures may move by spreading out the nodes from each other. In one example, the nodes spread from each other slowly allowing the user to view nodes distinguish from each other as well as the edges. In some embodiments, the visualization engine 322 optimizes the spread of the nodes for the user's view. In one example, the structure(s) stop moving once an optimal view has been reached.

It will be appreciated that the interactive visualization 900 may respond to gestures (e.g., multi-touch), stylus, or other interactions allowing the user to reorient nodes and edges and/or interacting with the underlying data.

The interactive visualization 900 may also respond to user actions such as when the user drags, clicks, or hovers a mouse cursor over a node. In some embodiments, when the user selects a node or edge, node information or edge information may be displayed. In one example, when a node is selected (e.g., clicked on by a user with a mouse or a mouse cursor hovers over the node), a node information box 908 may appear that indicates information regarding the selected node. In this example, the node information box 908 indicates an ID, box ID, number of elements (e.g., data points associated with the node), and density of the data associated with the node.

The user may also select multiple nodes and/or edges by clicking separate on each object, or drawing a shape (such as a box) around the desired objects. Once the objects are selected, a selection information box 912 may display some information regarding the selection. For example, selection information box 912 indicates the number of nodes selected and the total points (e.g., data points or elements) of the selected nodes.

The interactive visualization 900 may also allow a user to further interact with the display. Color option 914 allows the user to display different information based on color of the objects. Color option 914 in FIG. 9 is set to filter_Density, however, other filters may be chosen and the objects re-colored based on the selection. It will be appreciated that the objects may be colored based on any filter, property of data, or characterization. When a new option is chosen in the color option 914, the information and/or colors depicted in the color bar 910 may be updated to reflect the change.

Layout checkbox 916 may allow the user to anchor the interactive visualization 900. In one example, the layout checkbox 916 is checked indicating that the interactive visualization 900 is anchored. As a result, the user will not be able to select and drag the node and/or related structure. Although other functions may still be available, the layout checkbox 916 may help the user keep from accidentally moving and/or reorienting nodes, edges, and/or related structures. It will be appreciated the layout checkbox 916 may indicate that the interactive visualization 900 is anchored when the layout checkbox 916 is unchecked and that when the layout checkbox 916 is checked the interactive visualization 900 is no longer anchored.

The change parameters button 918 may allow a user to change the parameters (e.g., add/remove filters and/or change the resolution of one or more filters). In one example, when the change parameters button 918 is activated, the user may be directed back to the metric and filter selection interface window 600 (see FIG. 6) which allows the user to add or remove filters (or change the metric). The user may then view the filter parameter interface 700 (see FIG. 7) and change parameters (e.g., intervals and overlap) for one or more filters. The analysis module 320 may then re-analyze the data based on the changes and display a new interactive visualization 900 without again having to specify the data sets, filters, etc.

The find ID's button 920 may allow a user to search for data within the interactive visualization 900. In one example, the user may click the find ID's button 920 and receive a window allowing the user to identify data or identify a range of data. Data may be identified by ID or searching for the data based on properties of data and/or metadata. If data is found and selected, the interactive visualization 900 may highlight the nodes associated with the selected data. For example, selecting a single row or collection of rows of a database or spreadsheet may produce a highlighting of nodes whose corresponding partial cluster contains any element of that selection.

In various embodiments, the user may select one or more objects and click on the explain button 922 to receive in-depth information regarding the selection. In some embodiments, when the user selects the explain button 922, the information about the data from which the selection is based may be displayed. The function of the explain button 922 is further discussed herein (e.g., see discussion regarding FIG. 10).

In various embodiments, the interactive visualization 900 may allow the user to specify and identify subsets of interest, such as output filtering, to remove clusters or connections which are too small or otherwise uninteresting. Further, the interactive visualization 900 may provide more general coloring and display techniques, including, for example, allowing a user to highlight nodes based on a user-specified predicate, and coloring the nodes based on the intensity of user-specified weighting functions.

The interactive visualization 900 may comprise any number of menu items. The "Selection" menu may allow the following functions:
  Select singletons (select nodes which are not connected to other nodes)
  Select all (selects all the nodes and edges)
  Select all nodes (selects all nodes)
  Select all edges
  Clear selection (no selection)
  invert Selection (selects the complementary set of nodes or edges)
  Select "small" nodes (allows the user to threshold nodes based on how many points they have)
  Select leaves (selects all nodes which are connected to long "chains" in the graph)
  Remove selected nodes
  Show in a table (shows the selected nodes and their associated data in a table)
  Save selected nodes (saves the selected data to whatever format the user chooses. This may allow the user to subset the data and create new data sources which may be used for further analysis.)

In one example of the "show in a table" option, information from a selection of nodes may be displayed. The information may be specific to the origin of the data. In various embodiments, elements of a database table may be listed, however, other methods specified by the user may also be included. For example, in the case of microarray data from gene expression data, heat maps may be used to view the results of the selections.

The interactive visualization 900 may comprise any number of menu items. The "Save" menu may allow may allow the user to save the whole output in a variety of different formats such as (but not limited to):
  Image files (PNG/JPG/PDF/SVG etc.)
  Binary output (The interactive output is saved in the binary format. The user may reopen this file at any time to get this interactive window again)
In some embodiments, graphs may be saved in a format such that the graphs may be used for presentations. This may include simply saving the image as a pdf or png file, but it may also mean saving an executable .xml file, which may permit other users to use the search and save capability to the database on the file without having to recreate the analysis.

In various embodiments, a relationship between a first and a second analysis output/interactive visualization for differing values of the interval length and overlap percentage may be displayed. The formal relationship between the first and second analysis output/interactive visualization may be that when one cover refines the next, there is a map of simplicial complexes from the output of the first to the output of the second. This can be displayed by applying a restricted form of a three-dimensional graph embedding algorithm, in which a graph is the union of the graphs for the various parameter values and in which the connections are the connections in the individual graphs as well as connections from one node to its image in the following graph. The constituent graphs may be placed in its own plane in 3D space. In some embodiments, there is a restriction that each constituent graph remain within its associated plane. Each constituent graph may be displayed individually, but a small change of parameter value may result in the visualization of the adjacent constituent graph. In some embodiments, nodes in the initial graph will move to nodes in the next graph, in a readily visualizable way.

FIG. 10 is an example interactive visualization 1000 displaying an explain information window 1002 in some embodiments. In various embodiments, the user may select a plurality of nodes and click on the explain button. When the explain button is clicked, the explain information window 1002 may be generated. The explain information window 1002 may identify the data associated with the selected object(s) as well as information (e.g., statistical information) associated with the data.

In some embodiments, the explain button allows the user to get a sense for which fields within the selected data fields are responsible for "similarity" of data in the selected nodes and the differentiating characteristics. There can be many ways of scoring the data fields. The explain information window 1002 (i.e., the scoring window in FIG. 10) is shown along with the selected nodes. The highest scoring fields may distinguish variables with respect to the rest of the data.

In one example, the explain information window 1002 indicates that data from fields day0-day6 has been selected. The minimum value of the data in all of the fields is 0. The explain information window 1002 also indicates the maximum values. For example, the maximum value of all of the data associated with the day0 field across all of the points of the selected nodes is 0.353. The average (i.e., mean) of all of the data associated with the day0 field across all of the points of the selected nodes is 0.031. The score may be a relative (e.g., normalized) value indicating the relative function of the filter; here, the score may indicate the relative density of the data associated with the day0 field across all of the points of the selected nodes. Those skilled in the art will appreciate that any information regarding the data and/or selected nodes may appear in the explain information window 1002.

It will be appreciated that the data and the interactive visualization 1000 may be interacted with in any number of ways. The user may interact with the data directly to see where the graph corresponds to the data, make changes to the analysis and view the changes in the graph, modify the graph and view changes to the data, or perform any kind of interaction.

Figure 11:
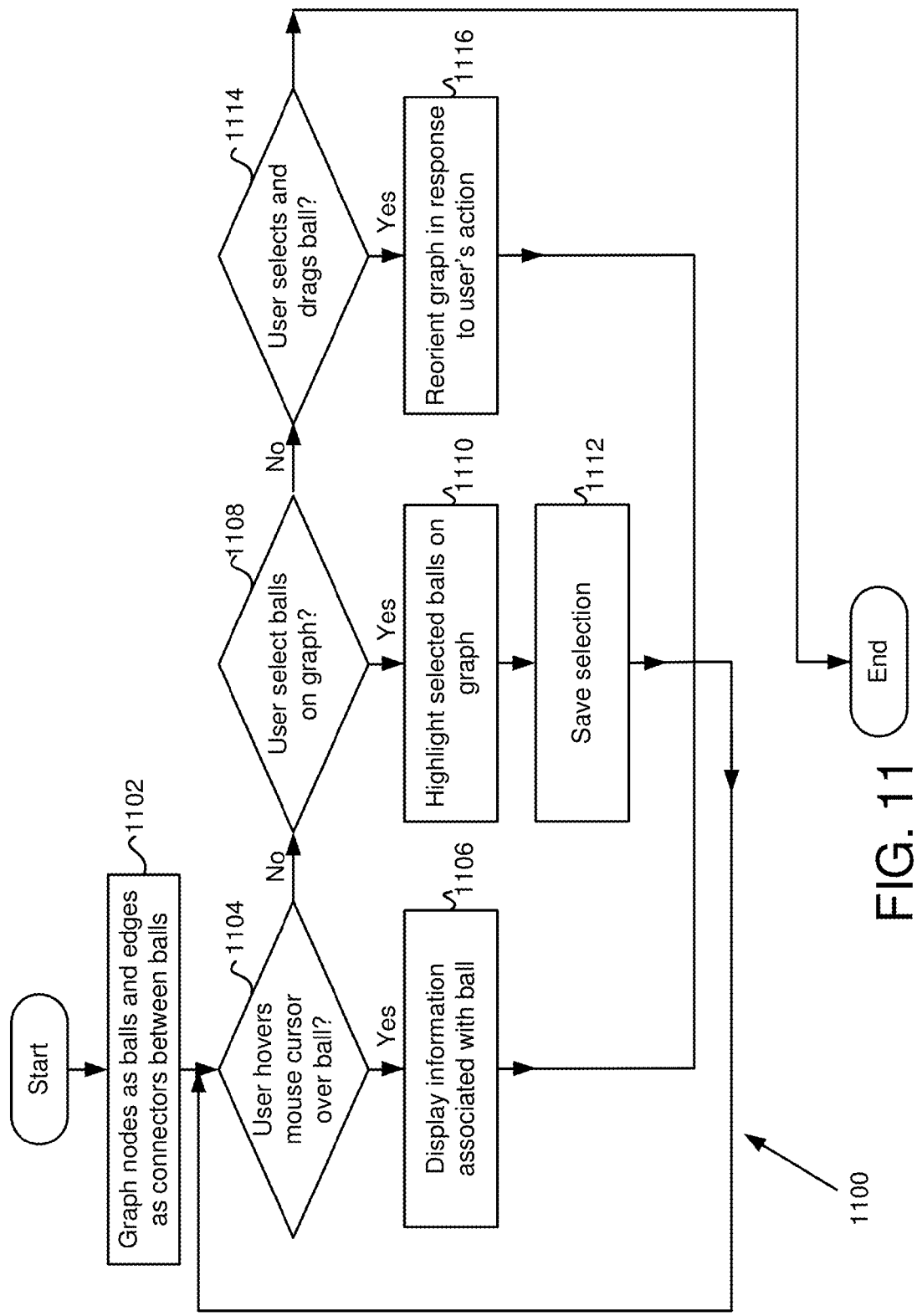
FIG. 11 is a flowchart of functionality of the interactive visualization in some embodiments.

FIG. 11 is a flowchart 1100 of functionality of the interactive visualization in some embodiments. In step 1102, the visualization engine 322 receives the analysis from the analysis module 320 and graphs nodes as balls and edges as connectors between balls 1202 to create interactive visualization 900 (see FIG. 9).

In step 1104, the visualization engine 322 determines if the user is hovering a mouse cursor over (or has selected) a ball (i.e., a node). If the user is hovering a mouse cursor over a ball or is selecting a ball, then information may be displayed regarding the data associated with the ball. In one example, the visualization engine 322 displays a node information window 908.

If the visualization engine 322 does not determine that the user is hovering a mouse cursor over (or has selected) a ball, then the visualization engine 322 determines if the user has selected balls on the graph (e.g., by clicking on a plurality of balls or drawing a box around a plurality of balls). If the user has selected a plurality of balls on the graph, the visualization engine 322 may highlight the selected balls on the graph in step 1110. The visualization engine 322 may also display information regarding the selection (e.g., by displaying a selection information window 912). The user may also click on the explain button 922 to receive more information associated with the selection the visualization engine 322 may display the explain information window 1002).

In step 1112, the user may save the selection. For example, the visualization engine 322 may save the underlying data, selected metric, filters, and/or resolution. The user may then access the saved information and create a new structure in another interactive visualization 900 thereby allowing the user to focus attention on a subset of the data.

If the visualization engine 322 does not determine that the user has selected balls on the graph, the visualization engine 322 may determine if the user selects and drags a ball on the graph in step 1114. If the user selects and drags a ball on the graph, the visualization engine 322 may reorient the selected balls and any connected edges and balls based on the user's action in step 1116. The user may reorient all or part of the structure at any level of granularity.

It will be appreciated that although FIG. 11 discussed the user hovering over, selecting, and/or dragging a ball, the user may interact with any object in the interactive visualization 900 (e.g., the user may hover over, select, and/or drag an edge). The user may also zoom in or zoom out using the interactive visualization 900 to focus on all or a part of the structure (e.g., one or more balls and/or edges). Any number of actions and operations may be performed using the interactive visualization 900.

Further, although balls are discussed and depicted in FIGS. 9-11, it will be appreciated that the nodes may be any shape and appear as any kind of object. Further, although some embodiments described herein discuss an interactive visualization being generated based on the output of algebraic topology, the interactive visualization may be generated based on any kind of analysis and is not limited.

For years, researchers have been collecting huge amounts of data on breast cancer, yet we are still battling the disease. Complexity, rather than quantity, is one of the fundamental issues in extracting knowledge from data. A topological data exploration and visualization platform may assist the analysis and assessment of complex data. In various embodiments, a predictive and visual cancer map generated by the topological data exploration and visualization platform may assist physicians to determine treatment options.

In one example, a breast cancer map visualization may be generated based on the large amount of available information already generated by many researchers. Physicians may send biopsy data directly to a cloud-based server which may localize a new patient's data within the breast cancer map visualization. The breast cancer map visualization may be annotated (e.g., labeled) such that the physician may view outcomes of patients with similar profiles as well as different kinds of statistical information such as survival probabilities. Each new data point from a patient may be incorporated into the breast cancer map visualization to improve accuracy of the breast cancer map visualization over time.

Although the following examples are largely focused on cancer map visualizations, it will be appreciated that at least some of the embodiments described herein may apply to any biological condition and not be limited to cancer and/or disease. For example, some embodiments, may apply to different industries.

Figure 12:
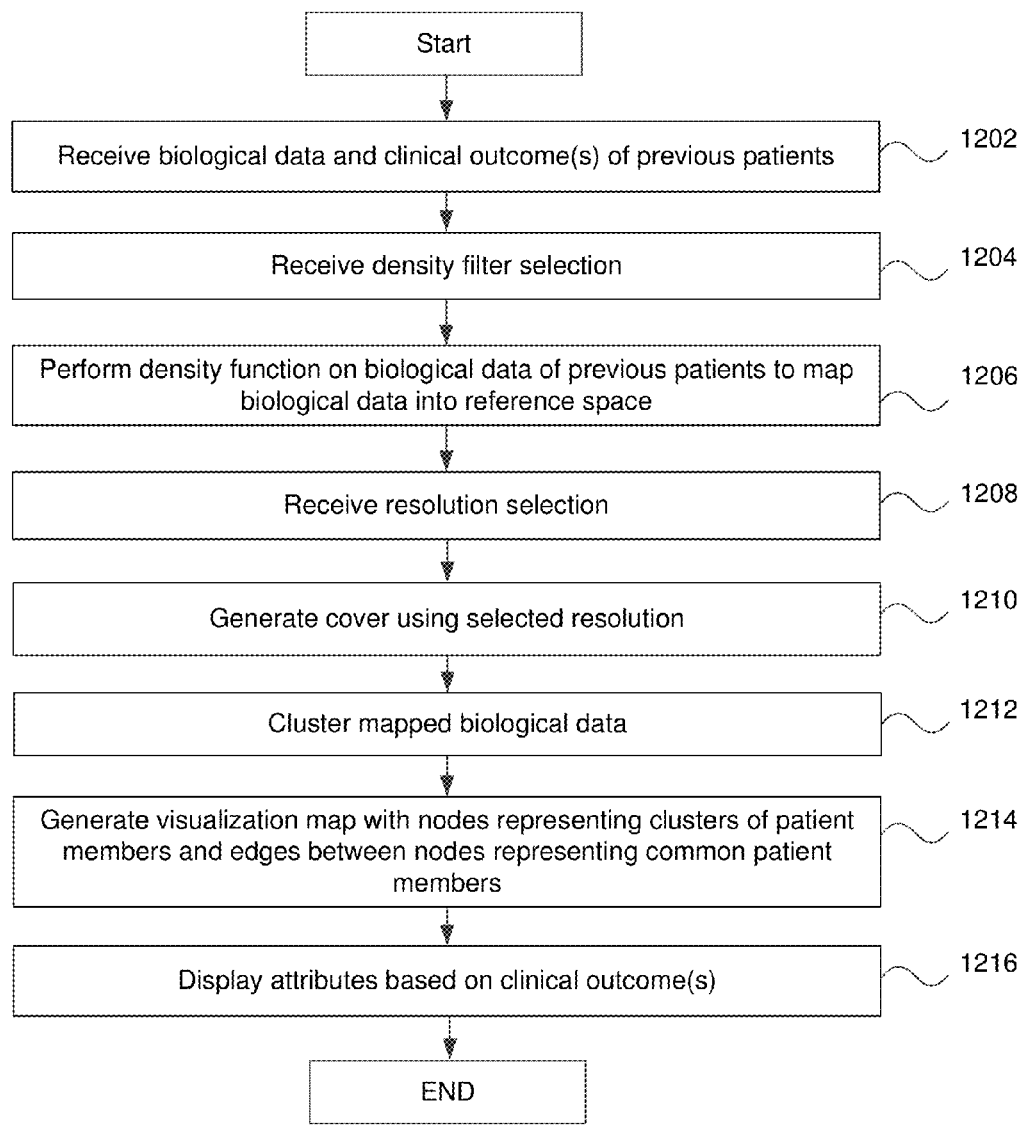
FIG. 12 is a flowchart of for generating a cancer map visualization utilizing biological data of a plurality of patients in some embodiments.

FIG. 12 is a flowchart for generating a cancer map visualization utilizing biological data of a plurality of patients in some embodiments. In various embodiments, the processing of data and user-specified options is motivated by techniques from topology and, in some embodiments, algebraic topology. As discussed herein, these techniques may be robust and general. In one example, these techniques apply to almost any kind of data for which some qualitative idea of "closeness" or "similarity" exists. It will be appreciated that the implementation of techniques described herein may apply to any level of generality.

In various embodiments, a cancer map visualization is generated using genomic data linked to clinical outcomes medical characteristics) which may be used by physicians during diagnosis and/or treatment. Initially, publicly available data sets may be integrated to construct the topological map visualizations of patients (e.g., breast cancer patients). It will be appreciated that any private, public, or combination of private and public data sets may be integrated to construct the topological map visualizations. A map visualization may be based on biological data such as, but not limited to, gene expression, sequencing, and copy number variation. As such, the map visualization may comprise many patients with many different types of collected data. Unlike traditional methods of analysis where distinct studies of breast cancer appear as separate entities, the map visualization may fuse disparate data sets while utilizing many datasets and data types.

In various embodiments, a new patient may be localized on the map visualization. With the map visualization for subtypes of a particular disease and a new patient diagnosed with the disease, point(s) may be located among the data points used in computing the map visualization (e.g., nearest neighbor) which is closest to the new patient point. The new patient may be labeled with nodes in the map visualization containing the closest neighbor. These nodes may be highlighted to give a physician the location of the new patient among the patients in the reference data set. The highlighted nodes may also give the physician the location of the new patient relative to annotated disease subtypes.

The visualization map may be interactive and/or searchable in real-time thereby potentially enabling extended analysis and providing speedy insight into treatment.

In step 1202, biological data and clinical outcomes of previous patients may be received. The clinical outcomes may be medical characteristics. Biological data is any data that may represent a condition (e.g., a medical condition) of a person. Biological data may include any health related, medical, physical, physiological, pharmaceutical data associated with one or more patients. In one example, biological data may include measurements of gene expressions for any number of genes. In another example, biological data may include sequencing information (e.g., RNA sequencing).

In various embodiments, biological data for a plurality of patients may be publicly available. For example, various medical health facilities and/or public entities may provide gene expression data for a variety of patients. In addition to the biological data, information regarding any number of clinical outcomes, treatments, therapies, diagnoses and/or prognoses may also be provided. Those skilled in the art will appreciate that any kind of information may be provided in addition to the biological data.

The biological data, in one example, may be similar to data S as discussed with regard to step 802 of FIG. 8. The biological data may include ID fields that identify patients and data fields that are related to the biological information (e.g., gene expression measurements).

FIG. 13 is an example data structure 1300 including biological data 1304a-1304y for a number of patients 1308a-1308n that may be used to generate the cancer map visualization in some embodiments. Column 1302 represents different patient identifiers for different patients. The patient identifiers may be any identifier.

At least some biological data may be contained within gene expression measurements 1304a-1304y. In FIG. 13, "y" represents any number. For example, there may be 50,000 or more separate columns for different gene expressions related to a single patient or related to one or more samples from a patient. It will be appreciated that column 1304a may represent a gene expression measurement for each patient (if any for some patients) associated with the patient identifiers in column 1302. The column 1304b may represent a gene expression measurement of one or more genes that are different than that of column 1304a. As discussed, there may be any number of columns representing different gene expression measurements.

Column 1306 may include any number of clinical outcomes, prognoses, diagnoses, reactions, treatments, and/or any other information associated with each patient. All or some of the information contained in column 1306 may be displayed (e.g., by a label or an annotation that is displayed on the visualization or available to the user of the visualization via clicking) on or for the visualization.

Rows 1308a-1.308n each contains biological data associated with the patient identifier of the row. For example, gene expressions in row 1308a are associated with patient identifier P1. As similarly discussed with regard to "y" herein, "n" represents any number. For example, there may be 100,000 or more separate rows for different patients.

It will be appreciated that there may be any number of data structures that contain any amount of biological data for any number of patients. The data structure(s) may be utilized to generate any number of map visualizations.

In step 1204, the analysis server may receive a filter selection. In some embodiments, the filter selection is a density estimation function. It will be appreciated that the filter selection may include a selection of one or more functions to generate a reference space.

In step 1206, the analysis server performs the selected filter(s) on the biological data of the previous patients to map the biological data into a reference space. In one example, a density estimation function, which is well known in the art, may be performed on the biological data (e.g., data associated with gene expression measurement data 1304a-1304y) to relate each patient identifier to one or more locations in the reference space (e.g., on a real line).

In step 1208, the analysis server may receive a resolution selection. The resolution may be utilized to identify overlapping portions of the reference space (e.g., a cover of the reference space R) in step 1210.

As discussed herein, the cover of R may be a finite collection of open sets (in the metric of R) such that every point in R lies in at least one of these sets. In various examples, R is k-dimensional Euclidean space, where k is the number of filter functions. Those skilled in the art will appreciate that the cover of the reference space R may be controlled by the number of intervals and the overlap identified in the resolution (e.g., see FIG. 7). For example, the more intervals, the finer the resolution in S (e.g., the similarity space of the received biological data)—that is, the fewer points in each S(d), but the more similar (with respect to the filters) these points may be. The greater the overlap, the more times that clusters in S(d) may intersect clusters in S(e)—this means that more "relationships" between points may appear, but, in some embodiments, the greater the overlap, the more likely that accidental relationships may appear.

In step 1212, the analysis server receives a metric to cluster the information of the cover in the reference space to partition S(d). In one example, the metric may be a Pearson Correlation. The clusters may form the groupings (e.g., nodes or balls). Various cluster means may be used including, but not limited to, a single linkage, average linkage, complete linkage, or k-means method.

As discussed herein, in some embodiments, the analysis module 320 may not cluster two points unless filter values are sufficiently "related" (recall that while normally related may mean "close," the cover may impose a much more general relationship on the filter values, such as relating two points s and t if ref(s) and ref(t) are sufficiently close to the same circle in the plane where ref( ) represents one or more filter functions). The output may be a simplicial complex, from which one can extract its 1-skeleton. The nodes of the complex may be partial clusters, (i.e., clusters constructed from subsets of S specified as the preimages of sets in the given covering of the reference space R).

In step 1214, the analysis server may generate the visualization map with nodes representing clusters of patient members and edges between nodes representing common patient members. In one example, the analysis server identifies nodes which are associated with a subset of the partition elements of all of the S(d) for generating an interactive visualization.

As discussed herein, for example, suppose that S={1, 2, 3, 4}, and the cover is $C_1$, $C_2$, $C_3$. Suppose cover $C_1$ contains {1, 4}, $C_2$ contains {1,2}, and $C_3$ contains {1,2,3,4}. If 1 and 2 are close enough to be clustered, and 3 and 4 are, but nothing else, then the clustering for S(1) may be {1}, {4}, and for S(2) it may be {1,2}, and for S(3) it may be {1,2}, {3,4}. So the generated graph has, in this example, at most four nodes, given by the sets {1}, {4}, {1, 2}, and {3, 4} (note that {1, 2} appears in two different clusterings). Of the sets of points that are used, two nodes intersect provided that the associated node sets have a non-empty intersection (although this could easily be modified to allow users to require that the intersection is "large enough" either in absolute or relative terms).

As a result of clustering, member patients of a grouping may share biological similarities (e.g., similarities based on the biological data).

The analysis server may join clusters to identify edges (e.g., connecting lines between nodes). Clusters joined by edges (i.e., interconnections) share one or more member patients. In step 1216, a display may display a visualization map with attributes based on the clinical outcomes contained in the data structures (e.g., see FIG. 13 regarding clinical outcomes). Any labels or annotations may be utilized based on information contained in the data structures. For example, treatments, prognoses, therapies, diagnoses, and the like may be used to label the visualization. In some embodiments, the physician or other user of the map visualization accesses the annotations or labels by interacting with the map visualization.

The resulting cancer map visualization may reveal interactions and relationships that were obscured, untested, and/or previously not recognized.

Figure 14:
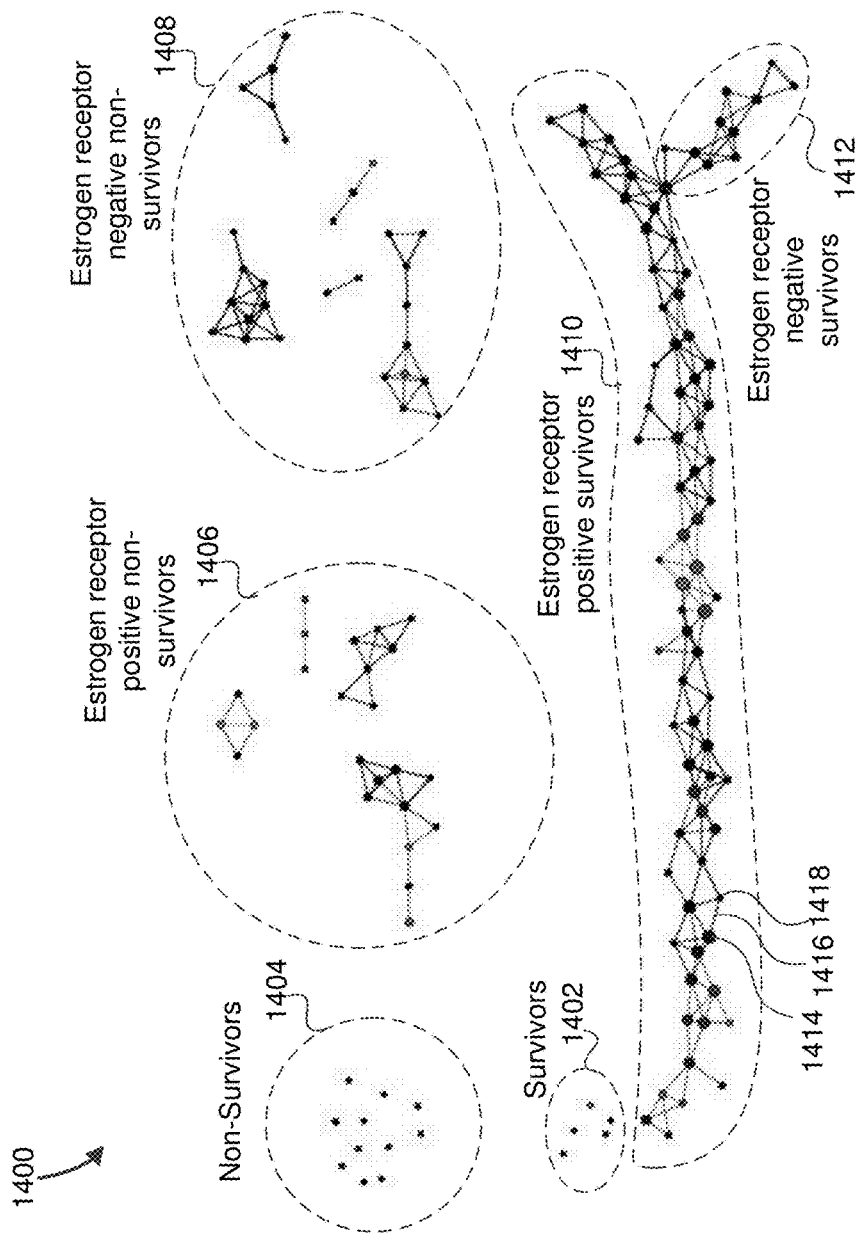
FIG. 14 is an example visualization displaying the cancer map in some embodiments.

FIG. 14 is an example visualization displaying the cancer map visualization 1400 in some embodiments. The cancer map visualization 1400 represents a topological network of cancer patients. The cancer map visualization 1400 may be based on publicly and/or privately available data.

In various embodiments, the cancer map visualization 1400 is created using gene expression profiles of excised tumors. Each node (i.e., ball or grouping displayed in the map visualization 1400) contains a subset of patients with similar genetic profiles.

As discussed herein, one or more patients (i.e., patient members of each node or grouping) may occur in multiple nodes. A patient may share a similar genetic profile with multiple nodes or multiple groupings. In one example, of 50,000 different gene expressions of the biological data, multiple patients may share a different genetic profiles (e.g., based on different gene expression combinations) with different groupings. When a patient shares a similar genetic profile with different groupings or nodes, the patient may be included within the groupings or nodes.

The cancer map visualization 1400 comprises groupings and interconnections that are associated with different clinical outcomes. All or some of the clinical outcomes may be associated with the biological data that generated the cancer map visualization 1400. The cancer map visualization 1400 includes groupings associated with survivors 1402 and groupings associated with non-survivors 1404. The cancer map visualization 1400 also includes different groupings associated with estrogen receptor positive non-survivors 1406, estrogen receptor negative non-survivors 1408, estrogen receptor positive survivors 1410, and estrogen receptor negative survivors 1412.

In various embodiments, when one or more patients are members of two or more different nodes, the nodes are interconnected by an edge (e.g., a line or interconnection). If there is not an edge between the two nodes, then there are no common member patients between the two nodes. For example, grouping 1414 shares at least one common member patient with grouping 1418. The intersection of the two groupings is represented by edge 1416. As discussed herein, the number of shared member patients of the two groupings may be represented in any number of ways including color of the interconnection, color of the groupings, size of the interconnection, size of the groupings, animations of the interconnection, animations of the groupings, brightness, or the like. In some embodiments, the number and/or identifiers of shared member patients of the two groupings may be available if the user interacts with the groupings 1414 and/or 1418 (e.g., draws a box around the two groupings and the interconnection utilizing an input device such as a mouse).

In various embodiments, a physician, on obtaining some data on a breast tumor, direct the data to an analysis server (e.g., analysis server 208 over a network such as the Internet) which may localize the patient relative to one or more groupings on the cancer map visualization 1400. The context of the cancer map visualization 1400 may enable the physician to assess various possible outcomes (e.g., proximity of representation of new patient to the different associations of clinical outcomes).

Figure 15:
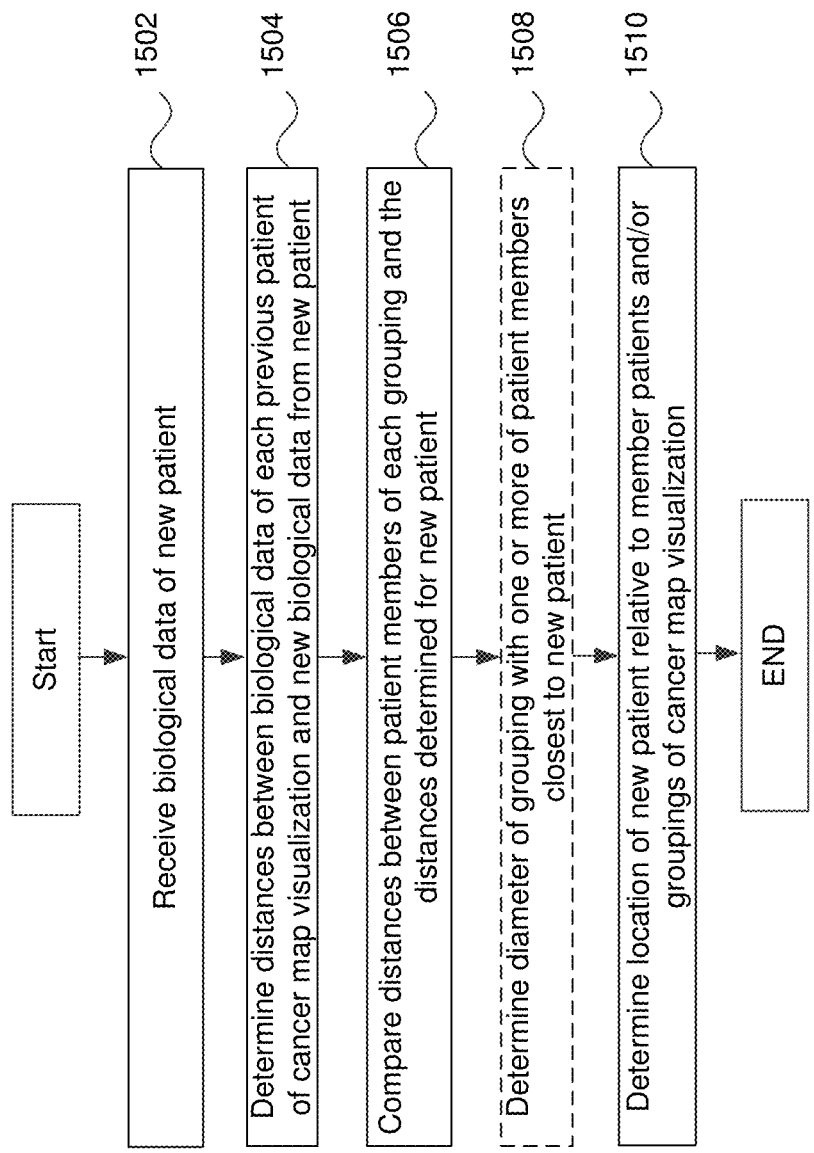
FIG. 15 is a flowchart of for positioning new patient data relative to the cancer map visualization in some embodiments.

FIG. 15 is a flowchart of for positioning new patient data relative to a cancer map visualization in some embodiments. In step 1502, new biological data of a new patient is received. In various embodiments, an input module 314 of an analysis server (e.g., analysis server 208 of FIGS. 1 and 2) may receive biological data of a new patient from a physician or medical facility that performed analysis of one or more samples to generate the biological data. The biological data may be any data that represents a biological data of the new patient including, for example, gene expressions, sequencing information, or the like.

In some embodiments, the analysis server 208 may comprise a new patient distance module and a location engine. In step 1504, the new patient distance module determines distances between the biological data of each patient of the cancer map visualization 1600 and the new biological data from the new patient. For example, the previous biological data that was utilized in the generation of the cancer map visualization 1600 may be stored in mapped data structures. Distances may be determined between the new biological data of the new patient and each of the previous patient's biological data in the mapped data structure.

It will be appreciated that distances may be determined in any number of ways using any number of different metrics or functions. Distances may be determined between the biological data of the previous patients and the new patients. For example, a distance may be determined between a first gene expression measurement of the new patient and each (or a subset) of the first gene expression measurements of the previous patients (e.g., the distance between G1 of the new patient and G1 of each previous patient may be calculated). Distances may be determined between all (or a subset of) other gene expression measurements of the new patient to the gene expression measurements of the previous patients.

In various embodiments, a location of the new patient on the cancer map visualization 1600 may be determined relative to the other member patients utilizing the determined distances.

In step 1506, the new patient distance module may compare distances between the patient members of each grouping to the distances determined for the new patient. The new patient may be located in the grouping of patient members that are closest in distance to the new patient. In some embodiments, the new patient location may be determined to be within a grouping that contains the one or more patient members that are closest to the new patient (even if other members of the grouping have longer distances with the new patient). In some embodiments, this step is optional.

In various embodiments, a representative patient member may be determined for each grouping. For example, some or all of the patient members of a grouping may be averaged or otherwise combined to generate a representative patient member of the grouping (e.g., the distances and/or biological data of the patient members may be averaged or aggregated). Distances may be determined between the new patient biological data and the averaged or combined biological data of one or more representative patient members of one or more groupings. The location engine may determine the location of the new patient based on the distances. In some embodiments, once the closest distance between the new patient and the representative patient member is found, distances may be determined between the new patient and the individual patient members of the grouping associated with the closest representative patient member.

In optional step 1508, a diameter of the grouping with the one or more of the patient members that are closest to the new patient (based on the determined distances) may be determined. In one example, the diameters of the groupings of patient members closest to the new patient are calculated. The diameter of the grouping may be a distance between two patient members who are the farthest from each other when compared to the distances between all patient members of the grouping. If the distance between the new patient and the closest patient member of the grouping is less than the diameter of the grouping, the new patient may be located within the grouping. If the distance between the new patient and the closest patient member of the grouping is greater than the diameter of the grouping, the new patient may be outside the grouping (e.g., a new grouping may be displayed on the cancer map visualization with the new patient as the single patient member of the grouping). If the distance between the new patient and the closest patient member of the grouping is equal to the diameter of the grouping, the new patient may be placed within or outside the grouping.

It will be appreciated that the determination of the diameter of the grouping is not required in determining whether the new patient location is within or outside of a grouping. In various embodiments, a distribution of distances between member patients and between member patients and the new patient is determined. The decision to locate the new patient within or outside of the grouping may be based on the distribution. For example, if there is a gap in the distribution of distances, the new patient may be separated from the grouping (e.g., as a new grouping). In some embodiments, if the gap is greater than a preexisting threshold (e.g., established by the physician, other user, or previously programmed), the new patient may be placed in a new grouping that is placed relative to the grouping of the closest member patients. The process of calculating the distribution of distances of candidate member patients to determine whether there may be two or more groupings may be utilized in generation of the cancer map visualization further described herein (e.g., in the process as described with regard to FIG. 12). It will be appreciated that there may be any number of ways to determine whether a new patient should be included within a grouping of other patient members.

In step 1510, the location engine determines the location of the new patient relative to the member patients and/or groupings of the cancer map visualization. The new location may be relative to the determined distances between the new patient and the previous patients. The location of the new patient may be part of a previously existing grouping or may form a new grouping.

In some embodiments, the location of the new patient with regard to the cancer map visualization may be performed locally to the physician. For example, the cancer map visualization 1400 may be provided to the physician (e.g., via a digital device). The physician may load the new patient's biological data locally and the distances may be determined locally or via a cloud-based server. The location(s) associated with the new patient may be overlaid on the previously existing cancer map visualization either locally or remotely.

It will be appreciated that, in some embodiments, the previous state of the cancer map visualization (e.g., cancer map visualization 1400) may be retained or otherwise stored and a new cancer map visualization generated utilizing the new patient biological data (e.g., in a method similar to that discussed with regard to FIG. 12). The newly generated map may be compared to the previous state and the differences may be highlighted thereby, in some embodiments, highlighting the location(s) associated with the new patient. In this way, distances may be not be calculated as described with regard to FIG. 15, but rather, the process may be similar to that as previously discussed.

Figure 16:
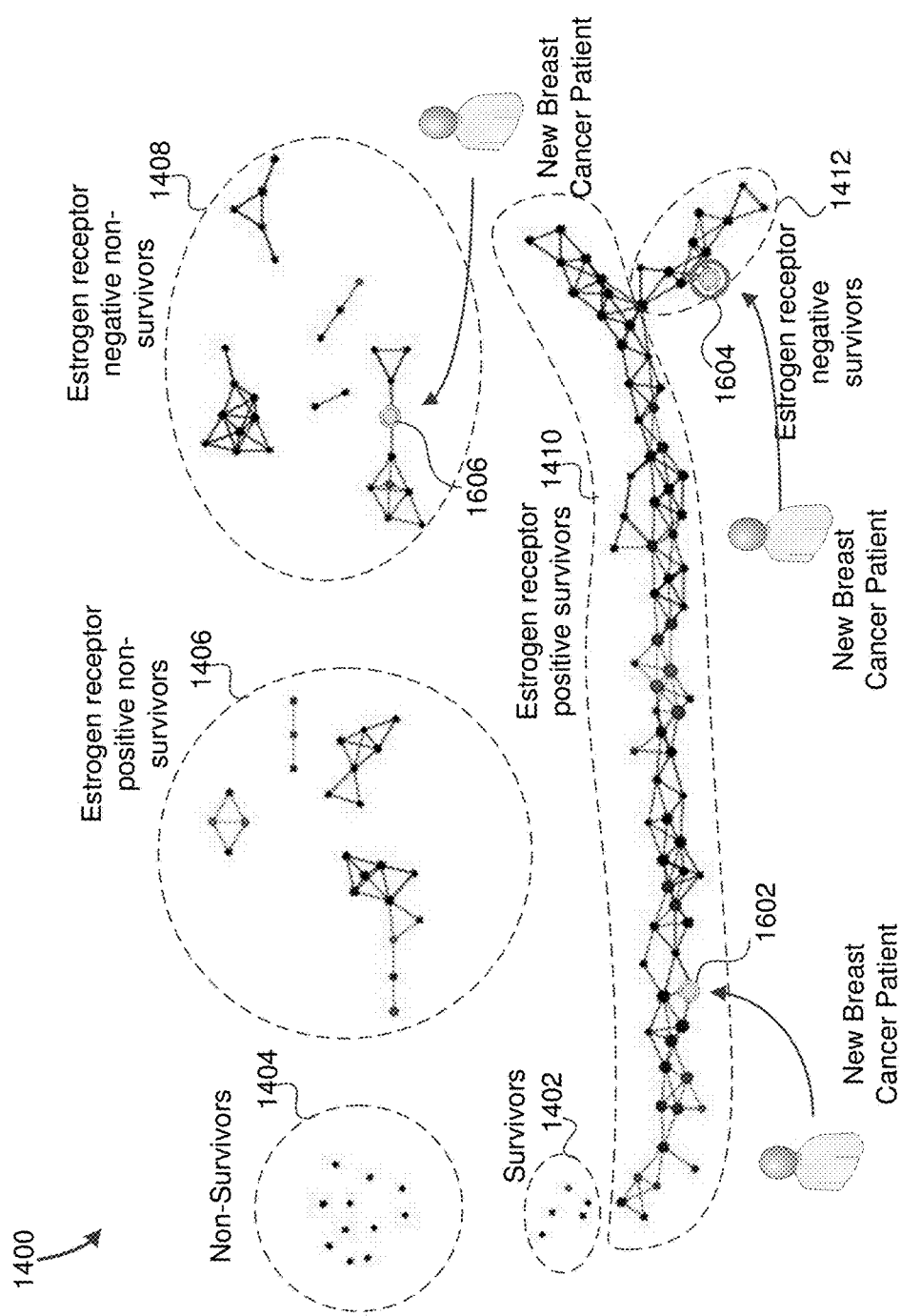
FIG. 16 is an example visualization displaying the cancer map including positions for three new cancer patients in some embodiments.

FIG. 16 is an example visualization displaying the cancer map including positions for three new cancer patients in some embodiments. The cancer map visualization 1400 comprises groupings and interconnections that are associated with different clinical outcomes as discussed with regard to FIG. 14. All or some of the clinical outcomes may be associated with the biological data that generated the cancer map visualization 1400. The cancer map visualization 1400 includes different groupings associated with survivors 1402, groupings associated with non-survivors 1404, estrogen receptor positive non-survivors 1406, estrogen receptor negative non-survivors 1408, estrogen receptor positive survivors 1410, and estrogen receptor negative survivors 1412.

The cancer map visualization 1400 includes three locations for three new breast cancer patients. The breast cancer patient location 1602 is associated with the clinical outcome of estrogen receptor positive survivors. The breast cancer patient location 1604 is associated with the clinical outcome of estrogen receptor negative survivors. Unfortunately, breast cancer patient location 1606 is associated with estrogen receptor negative non-survivors. Based on the locations, a physician may consider different diagnoses, prognoses, treatments, and therapies to maintain or attempt to move the breast cancer patient to a different location utilizing the cancer map visualization 1400.

In some embodiments, the physician may assess the underlying biological data associated with any number of member patients of any number of groupings to better understand the genetic similarities and/or dissimilarities. The physician may utilize the information to make better informed decisions.

The patient location 1604 is highlighted on the cancer map visualization 1400 as active (e.g., selected by the physician). It will be appreciated that the different locations may be of any color, size, brightness, and/or animated to highlight the desired location(s) for the physician. Further, although only one location is identified for three different breast cancer patients, any of the breast cancer patients may have multiple locations indicating different genetic similarities.

It will be appreciated that the cancer map visualization 1400 may be updated with new information at any time. As such, as new patients are added to the cancer map visualization 1400, the new data updates the visualization such that as future patients are placed in the map, the map may already include the updated information. As new information and/or new patient data is added to the cancer map visualization 1400, the cancer map visualization 1400 may improve as a tool to better inform physicians or other medical professionals.

In various embodiments, the cancer map visualization 1400 may track changes in patients over time. For example, updates to a new patient may be visually tracked as changes in are measured in the new patient's biological data. In some embodiments, previous patient data is similarly tracked which may be used to determine similarities of changes based on condition, treatment, and/or therapies, for example. In various embodiments, velocity of change and/or acceleration of change of any number of patients may be tracked over time using or as depicted on the cancer map visualization 1400. Such depictions may assist the treating physician or other personnel related to the treating physician to better understand changes in the patient and provide improved, current, and/or updated diagnoses, prognoses, treatments, and/or therapies.

Figure 17:
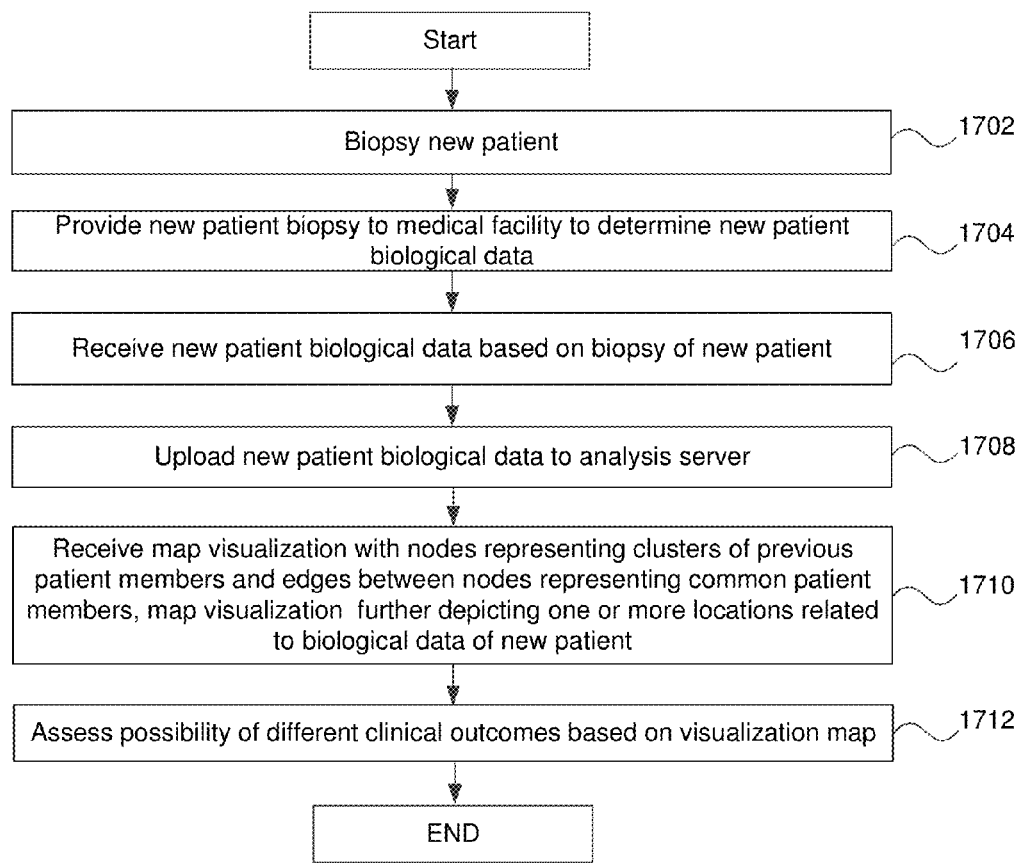
FIG. 17 is a flowchart of utilization the visualization and positioning of new patient data in some embodiments

FIG. 17 is a flowchart of utilization the visualization and positioning of new patient data in some embodiments. In various embodiments, a physician may collect amounts of genomic information from tumors removed from a new patient, input the data (e.g., upload the data to an analysis server), and receive a map visualization with a location of the new patient. The new patient's location within the map may offer the physician new information about the similarities to other patients. In some embodiments, the map visualization may be annotated so that the physician may check the outcomes of previous patients in a given region of the map visualization are distributed and then use the information to assist in decision-making for diagnosis, treatment, prognosis, and/or therapy.

In step 1702, a medical professional or other personnel may remove a sample from a patient. The sample may be of a tumor, blood, or any other biological material. In one example, a medical professional performs a tumor excision. Any number of samples may be taken from a patient.

In step 1704, the sample(s) may be provided to a medical facility to determine new patient biological data. In one example, the medical facility measures genomic data such as gene expression of a number of genes or protein levels.

In step 1706, the medical professional or other entity associated with the medical professional may receive the new patient biological data based on the sample(s) from the new patient. In one example, a physician may receive the new patient biological data. The physician may provide all or some of the new patient biological data to an analysis server over the Internet (e.g., the analysis server may be a cloud-based server). In some embodiments, the analysis server is the analysis server 208 of FIG. 2. In some embodiments, the medical facility that determines the new patient biological data provides the biological data in an electronic format which may be uploaded to the analysis server. In some embodiments, the medical facility that determines the new patient biological data (e.g., the medical facility that measures the genomic data) provide the biological data to the analysis server at the request of the physician or others associated with the physician. It will be appreciated that the biological data may be provided to the analysis server in any number of ways.

The analysis server may be any digital device and may not be limited to a digital device on a network. In some embodiments, the physician may have access to the digital device. For example, the analysis server may be a table, personal computer, local server, or any other digital device.

Once the analysis server receives the biological data of the new patient (e.g., the new patient biological data may be uploaded to the analysis serer in step 1708), the new patient may be localized in the map visualization and the information may be sent back to the physician in step 1710. The visualization may be a map with nodes representing clusters of previous patient members and edges between nodes representing common patient members. The visualization may further depict one or more locations related to the biological data of the new patient.

The map visualization may be provided to the physician or other associated with the physician in real-time. For example, once the biological data associated with the new patient is provided to the analysis server, the analysis server may provide the map visualization back to the physician or other associated with the physician within a reasonably short time (e.g., within seconds or minutes). In some embodiments, the physician may receive the map visualization over any time.

The map visualization may be provided to the physician in any number of ways. For example, the physician may receive the map visualization over any digital device such as, but not limited to, an office computer, IPad, tablet device, media device, smartphone, e-reader, or laptop.

In step 1712, the physician may assess possible different clinical outcomes based on the map visualization. In one example, the map-aided physician may make decisions on therapy and treatments depending on where the patient lands on the visualization (e.g., survivor or non-survivor). The map visualization may include annotations or labels that identify one or more sets of groupings and interconnections as being associated with one or more clinical outcomes. The physician may assess possible clinical outcomes based on the position(s) on the map associated with the new patient.

Figure 18:
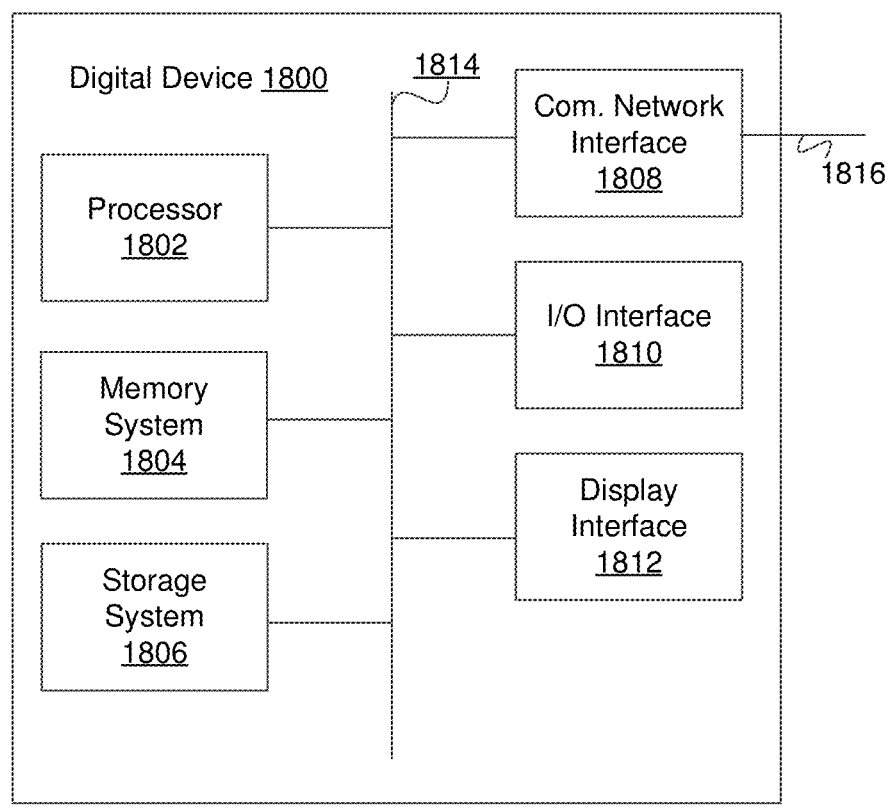
FIG. 18 is an example digital device in some embodiments.

FIG. 18 is a block diagram of an exemplary, digital device 1800. The digital device 1800 comprises a processor 1802, a memory system 1804, a storage system 1806, a communication network interface 1808, an 110 interface 1810, and a display interface 1812 communicatively coupled to a bus 1814. The processor 1802 may be configured to execute executable instructions (e.g., programs). In some embodiments, the processor 1802 comprises circuitry or any processor capable of processing the executable instructions.

The memory system 1804 is any memory configured to store data. Some examples of the memory system 1804 are storage devices, such as RAM or ROM. The memory system 1804 can comprise the ram cache. In various embodiments, data is stored within the memory system 1804. The data within the memory system 1804 may be cleared or ultimately transferred to the storage system 1806.

The storage system 1806 is any storage configured to retrieve and store data. Some examples of the storage system 1806 are flash drives, hard drives, optical drives, and/or magnetic tape. In some embodiments, the digital device 1800 includes a memory system 1804 in the form of RAM and a storage system 1806 in the form of flash data. Both the memory system 1804 and the storage system 1806 comprise computer readable media which may store instructions or programs that are executable by a computer processor including the processor 1802.

The communication network interface (com. network interface) 1808 can be coupled to a data network (e.g., communication network 204) via the link 1816. The communication network interface 1808 may support communication over an Ethernet connection, a serial connection, a parallel connection, or an ATA connection, for example. The communication network interface 1808 may also support wireless communication (e.g., 1802.11 a/b/g/n, WiMAX). It will be apparent to those skilled in the art that the communication network interface 1808 can support many wired and wireless standards.

The optional input/output (I/O) interface 1810 is any device that receives input from the user and output data. The optional display interface 1812 is any device that may be configured to output graphics and data to a display. In one example, the display interface 1812 is a graphics adapter.

It will be appreciated that the hardware elements of the digital device 1800 are not limited to those depicted in FIG. 18. A digital device 1800 may comprise more or less hardware elements than those depicted. Further, hardware elements may share functionality and still be within various embodiments described herein. In one example, encoding and/or decoding may be performed by the processor 1802 and/or a co-processor located on a GPU.

Figure 19:
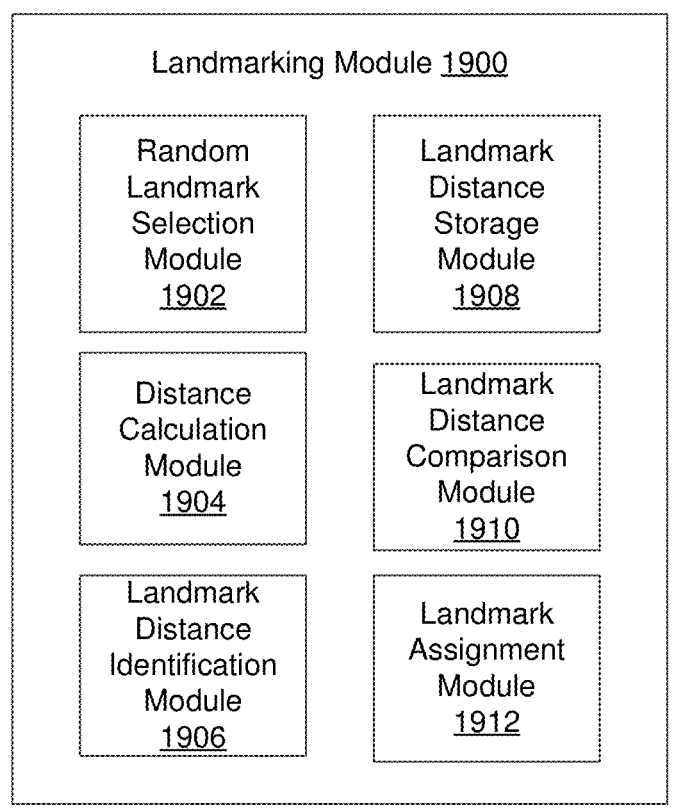
FIG. 19 shows an example landmark module configured to identify landmark points that approximate or represent a larger collection of data points in accordance with various embodiments.

FIG. 19 shows example a landmark module 1900 configured to identify landmark points that approximate or represent a larger collection of data points in accordance with various embodiments. In this example, landmark module 1900 comprises landmark selection module 1902, a distance calculation module 1904, a landmark distance identification module 1906, a landmark distance storage module 1908, a landmark distance comparison module 1910, and a landmark assignment module 1912.

The landmark selection module 1902 may be configured to randomly select a first subset of the data points to assign as an initial set of landmark points. For example, the landmark selection module 1902 may select an initial set of points from the finite metric space as a landmark set L. It will be appreciated that the landmark selection module 1902 may select points pseudo-randomly (e.g., randomly within the bounds of software or computer implementation) and/or in combination with other methods (e.g., randomly within portions of the finite metric space or based, in part, on density of information). Landmark selection module 1902 may select points in any number of ways (e.g., the landmark selection module 1902 may select points based on any methodology and/or may not select points randomly).

The distance calculation module 1904 may be configured to calculate the distances between a respective non-landmark data point and each landmark point in the finite reference space. In some embodiments, the distance calculation module 1904 stores some or all of the information for later use.

The landmark distance identification module 1906 may be configured to identify the shortest distance from among the distances between the respective non-landmark data point and each landmark. The shortest distance between a non-landmark data point and a landmark data point may indicate the closest landmark to that particular non-landmark data point.

The landmark distance storage module 1908 may be configured to store the shortest data point distance for the respective non-landmark data point as a landmark distance for that data point. The landmark distance comparison module 1910 may be configured to determine a longest landmark distance from among the shortest distances (e.g., stored by the landmark distance storage module 1908) to a nearest landmark for each data point.

The landmark assignment module 1912 may be configured to add a data point associated with the longest landmark distance to the initial set of landmark points thereby adding a new landmark and creating a new set of landmark points.

As described herein, the landmarks (L) are a subset of the collection data points in the finite metric space. The landmarks may be chosen such that the subset is representative of or to approximate the received data. In some embodiments, the landmarks are chosen to reflect both the "average" and "extreme" behavior of the data points in the space and, thus, analytics and other operations performed on the landmark set as an approximation of the behavior of the whole metric space (X). In some embodiments, the landmark points may be used as a means of increasing scale and performance when working with a large collection of data by only operating on a subset of a space.

Figure 20:
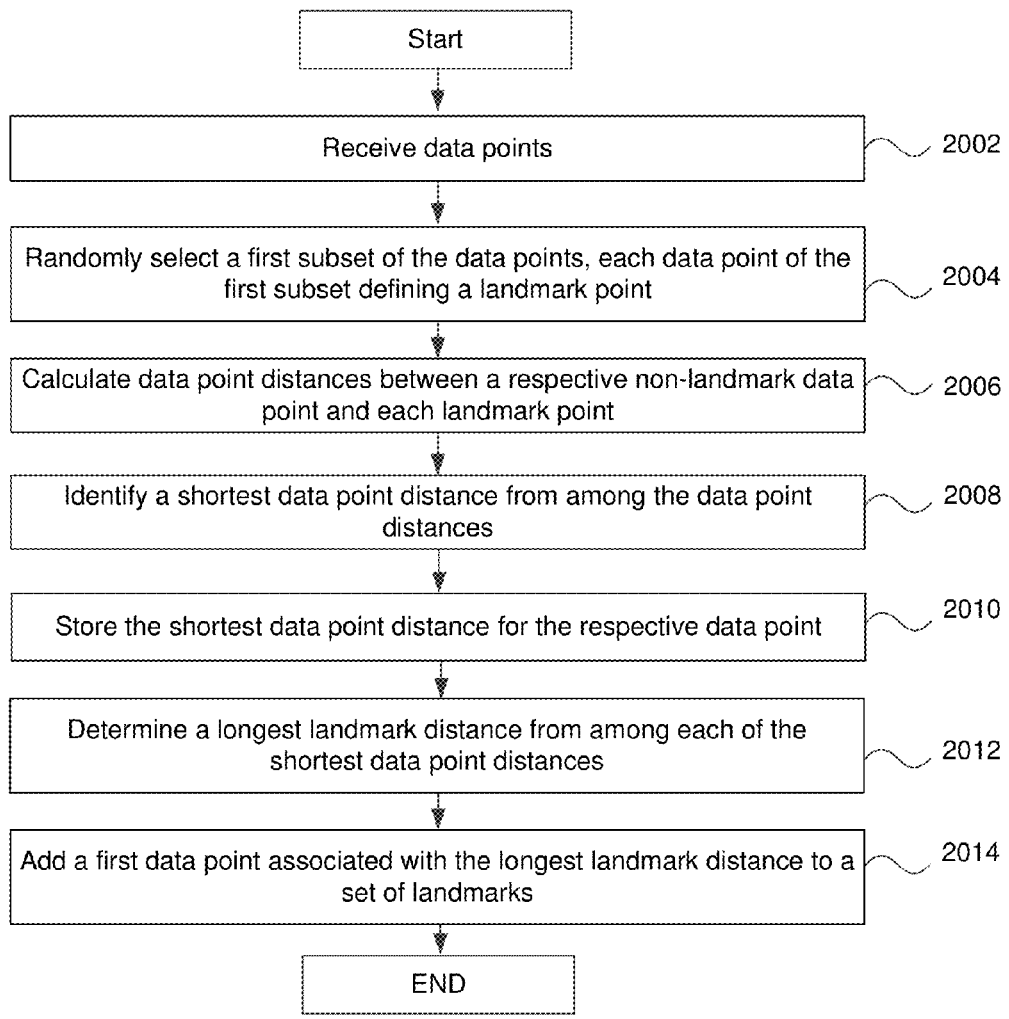
FIG. 20 is a flowchart for generating a set of landmark points in some embodiments.

FIG. 20 is a flow chart 2000 depicting an example method for generating a set of landmark points from a data set in some embodiments. The following discussion regarding the steps in FIG. 20 will be described with references to FIGS. 21A-D and FIG. 22A-C. In step 2002, the landmark selection module 1902 receives a set of data points defining a finite metric space. For example, receiving data may include landmark selection module 1902 accessing a data structure containing a very large volume of multidimensional data, as shown in FIG. 21A.

Figure 21A:
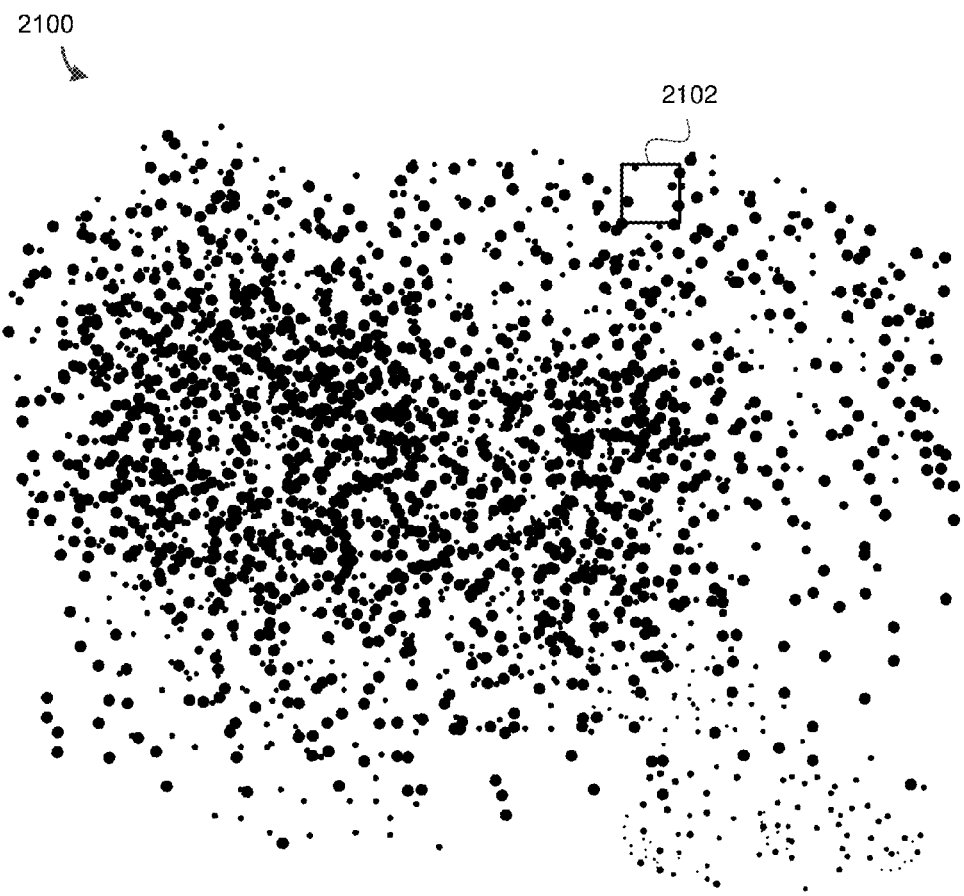
FIG. 21A shows example metric space containing data in accordance with various embodiments.
Figure 21B:
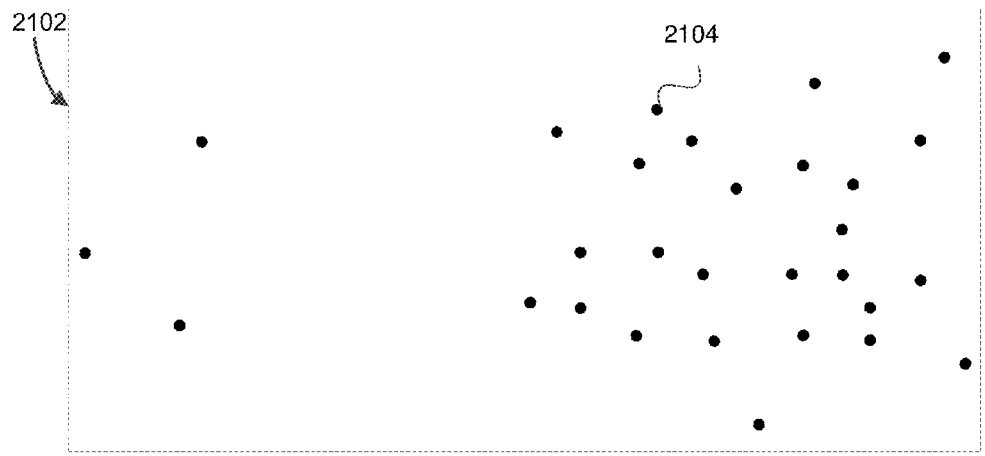
FIG. 21B shows subset composed of individual data points in accordance with some embodiments.

FIG. 21A shows example metric space 2100 containing data in accordance with various embodiments. Since the amount of data shown in metric space 2100 handled by the methods and algorithms discussed herein may be large (e.g., on the order of 200 million+ data points), subset 2102 of metric space 2100 will be used for discussion purposes. Accordingly, FIG. 21B shows subset 2102 composed of individual data points 2104 in accordance with some embodiments.

Figure 21C:
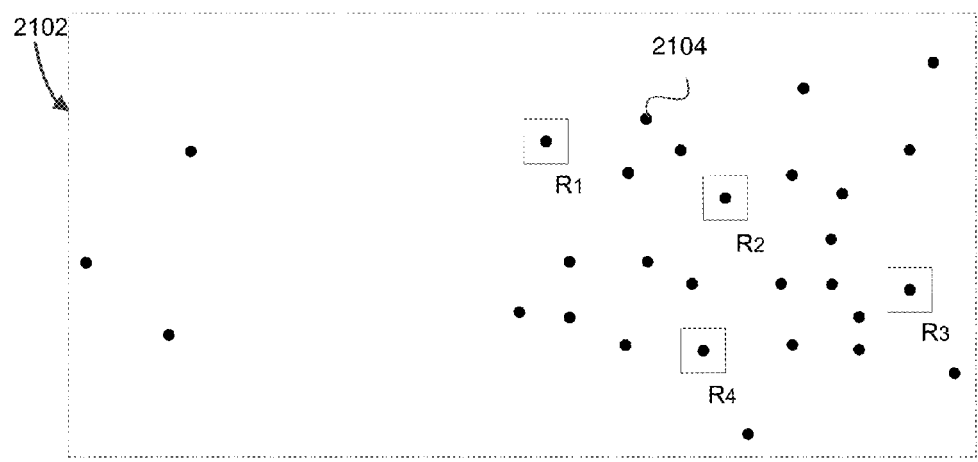
FIG. 21C shows example random landmarks $R_1$, $R_2$, $R_3$, and $R_4$ that have been randomly selected as initial landmarks in the subset identified in FIG. 21A.

At step 2004, the analysis system 2606 selects a random subset of individual data points 2104 as a first set (e.g., an initial set) of landmark points. To illustrate this step, FIG. 21C shows example random landmarks $R_1$, $R_2$, $R_3$, and $R_4$ that have been randomly selected as initial landmarks. Since metric space 2100 is large (e.g., 200 million+ data points), points selected at random tend to be located in high density areas, which is a benefit when attempting to choose a subset of points that represent the characteristics of the larger space. For example, for a metric space of approximately 200 million data points, the number of randomly selected landmark points could be approximately 5,000 points. Thus, the probability that a significant portion of the randomly selected landmarks may end up being outliers, for example, may be quite low and the randomly selected landmarks end up being located in higher density data point regions.

Figure 21D:
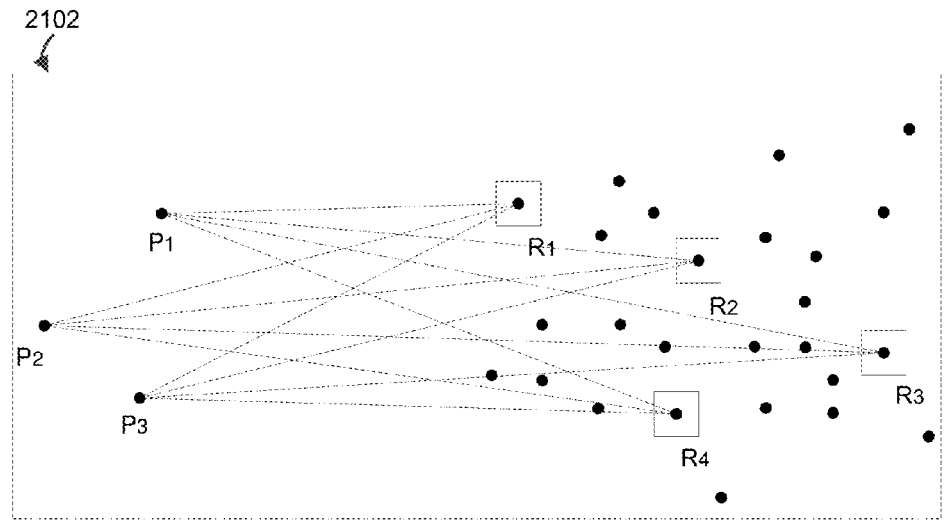
FIG. 21D shows lines corresponding to data point distances to each landmark for three points ($P_1$, $P_2$, and $P_3$) in the subset identified in FIG. 21A.
Figure 22A:
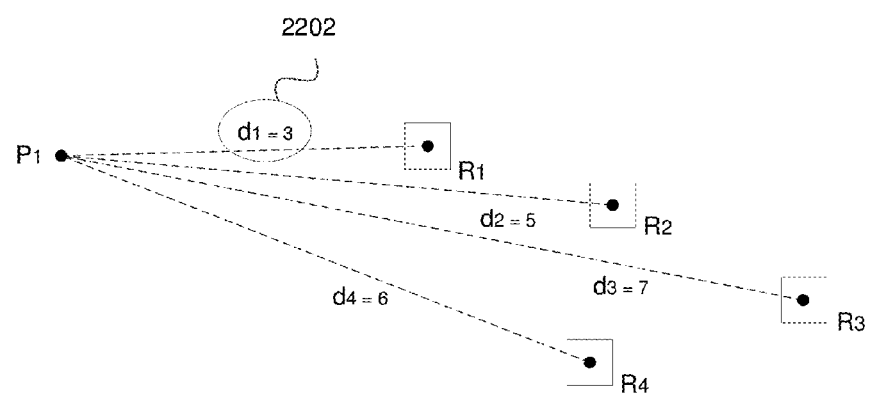
FIG. 22A shows example data point distances between point $P_1$ and random landmarks $R_1$, $R_2$, $R_3$, and $R_4$.

At step 2006, for each non-landmark point, the distance calculation module 1904 calculates distances between that particular non-landmark point and each landmark point. As used herein, the distances between landmark points and individual data points 2104 are referred to as data point distances. Accordingly, FIG. 21D shows lines corresponding to data point distances to each landmark for three points ($P_1$, $P_2$, and $P_3$). It should be appreciated that, in various embodiments, the data point distances for all other points other than $P_1$, $P_2$, and $P_3$ and the landmarks are also calculated, but of clarity and illustrative purposes, the lines shown in FIG. 21D have only been drawn for $P_1$, $P_2$, and $P_3$. Accordingly, in this example, each distance between $P_1$ and $R_1$, $R_2$, $R_3$, and $R_4$ is calculated, each distance between $P_2$ and $R_1$, $R_2$, $R_3$, and $R_4$ is calculated, etc. until the distances between each non-landmark point and all the landmarks are calculated. FIGS. 22A and 229 show this process in more detail.

FIG. 22A shows example data point distances between point $P_1$ and random landmarks $R_1$, $R_2$, $R_3$, and $R_4$. In this example, distance $d_1$ between $P_1$ and $R_1$ is 3, distance $d_2$ between $P_1$ and $R_2$ is 5, distance $d_3$ between $P_1$ and $R_3$ is 7, and distance $d_4$ between $P_1$ and $R_4$ is 6. In various embodiments, the landmark distance for a respective non-landmark point is defined as the shortest distance to its nearest landmark or the shortest data point distance. In this example, distances $d_1$, $d_2$, $d_3$, and $d_4$ are compared to each other to determine which is the shortest distance to a landmark from $P_1$. In this example, distance $d_1$, between $P_1$ and $R_1$, is the shortest distance and, thus, defined as landmark distance 2202 for $P_1$. Accordingly, $R_1$ is the closest landmark to $P_1$ with corresponding landmark distance 2202 (i.e., $d_1=3$).

Figures 22B, 22C:
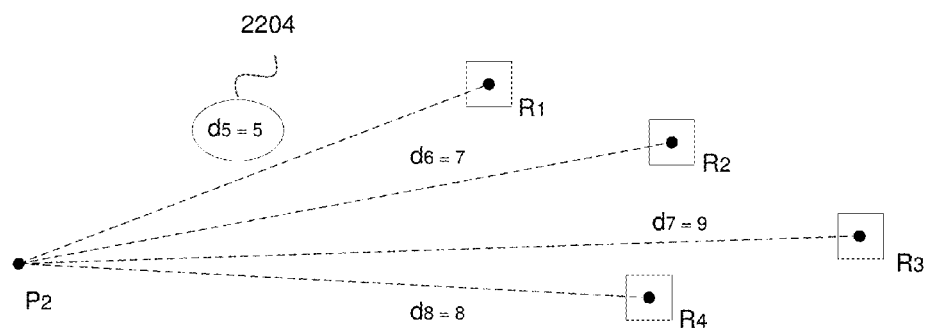
FIG. 22B shows example distances between point $P_2$ and random landmarks $R_1$, $R_2$, $R_3$, and $R_4$.
FIG. 22C shows an example table wherein distances for each point are stored.

Similarly, FIG. 22B shows example distances between point $P_2$ and random landmarks $R_1$, $R_2$, $R_3$, and $R_4$. In this example, distance $d_5$ between $P_2$ and $R_1$ is 5, distance $d_6$ between $P_2$ and $R_2$ is 5, distance $d_7$ between $P_2$ and $R_3$ is 9, and distance $d_8$ between $P_2$ and $R_4$ is 8. As above, distances $d_5$, $d_6$, $d_7$, and $d_8$ are compared to each other to determine which is the shortest distance to $P_2$'s nearest landmark, which is distance $d_5$. Accordingly, distance $d_5$ between $P_2$ and $R_1$ is landmark distance 2204. Thus, $R_1$ is also the closest landmark to $P_2$ at landmark distance 2204 (i.e., $d_5=5$), in this example.

Accordingly, the distance calculations described in FIGS. 22A and 22B are, thus, calculated for $P_3$ and every other non-landmark point in metric space 2100 and the distance calculations may be stored. For example, FIG. 22C shows an example table 2250 wherein distances for each point are stored. Although FIG. 22C depicts a table, it will be appreciated that any data structure(s) or combination of data structure(s) may be utilized. Further, although table 2250 includes all distances from P1 to each landmark, it will be appreciated that, in some embodiments, a subset of the distances may be stored. In one example, only the shortest distance between P1 and the closest landmark may be stored.

Further, in this example, only the distances for points $P_1$ and $P_2$ are shown, but it should be appreciated that such a table or array would include distances for each non-landmark point. Thus, in one embodiment, table 2250 stores the distances for each point to each landmark in metric space 2100. From these distances, a landmark distance (e.g., shortest distance to a nearest landmark) for each point may be identified and compared to generate a second set of landmark points. This process is discussed further with respect to FIGS. 23A-23D.

Figures 23A, 23B:
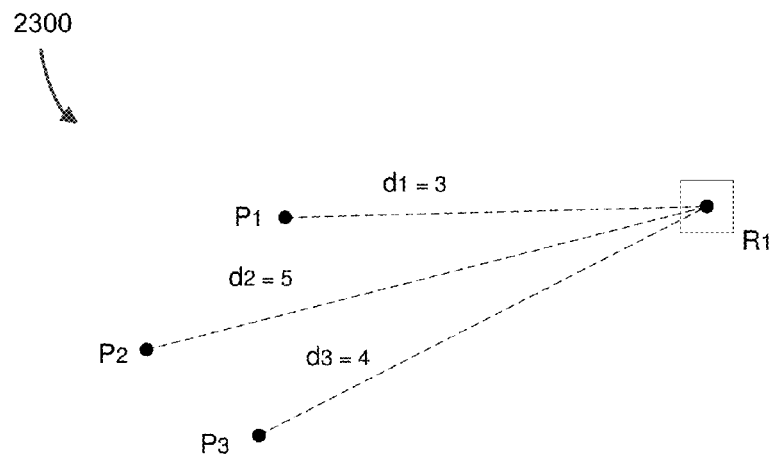
FIG. 23A shows example landmark distances for points $P_1$, $P_2$, and $P_3$ to landmark $R_1$ which can be used to demonstrate the selection of additional landmark points.
FIG. 23B shows example shortest distances from each non-landmark point to each landmark point.

At step 2008, landmark distance identification module 1906 identifies the shortest data point distance from among the data point distances. FIG. 23A shows example landmark distances for points $P_1$, $P_2$, and $P_3$ to landmark $R_1$ which can be used to demonstrate the selection of additional landmark points. For example, landmark distance identification module 1906 determines for each point which landmark point is the closest landmark point for that respective point. This may include, for example, comparing the distance values $d_n$ from table 2250 for each point to determine which distance $d_n$ is the shortest. Accordingly, in this example, the distance between a landmark and $P_1$ is 3 (i.e., between $P_1$ and landmark point $R_1$) and the shortest distance to a landmark point from $P_2$ is 5 which is also to landmark point $R_1$.

Such an operation may use an indexable state for X (i.e., points such as $P_1$, $P_2$, and $P_3$ in metric space 2100), an indexable array for L (e.g., L[l] is the index in X of the l'th landmark) where each random landmark point $R_n$ and subsequently determined landmark point is in L, and dClosest[x] which records the shortest distance between X[x] (i.e., $P_1$, $P_2$, $P_3$, etc.) and a respective closest landmark point, and in L[ ] with is true if x is in L.

At step 2010, landmark distance storage module 1908 stores the shortest distance from each non-landmark point to a landmark point (or the distance to the nearest landmark) in an array. FIG. 23B shows example shortest distances from each non-landmark point to each landmark point. In FIG. 23B, table 2350 contains the shortest distances between each data point $P_1$, $P_2$, and $P_3$ and its closest landmark, respectively.

In various embodiments, for each non-landmark point, the closest landmark point is identified. As a result, a list of non-landmark points that identify the same landmark point as the closest landmark point may be identified. For example, for each such landmark point, a table such as table 2350 may be generated that identifies the non-landmark points that identify the same particular landmark point as being closest. The table 2350 may further identify distances between those non-landmark points and the same particular landmark point. In this example, table 2350 may contain the shortest distances between data points $P_1$, $P_2$, and $P_3$ and landmark point $R_1$. data point and only one landmark $R_1$ At step 2012, landmark distance comparison module 1910 determines a longest landmark distance from among each of the shortest data point distances (or a longest landmark distance) from among each of the landmark distances. For example, returning to FIG. 23A, random landmark point $R_1$ is the landmark nearest to points $P_1$, $P_2$, and $P_3$ and, thus, the landmark distance $l_n$ (i.e., the distance to a nearest landmark) for each of these points is its respective distance to $R_1$, which may be stored in table 2350. Thus, in this example, the landmark distance for $P_1$ is $l_1=3$, the landmark distance for $P_2$ is $l_2=5$, and the landmark distance for $P_3$ is $l_3=4$. Accordingly, landmark distance comparison module 1910 compares these distances to identify the longest distance which, in this example, is $l_2=5$ shown circled in FIG. 23B, belonging to point $P_2$.

Figure 23C:
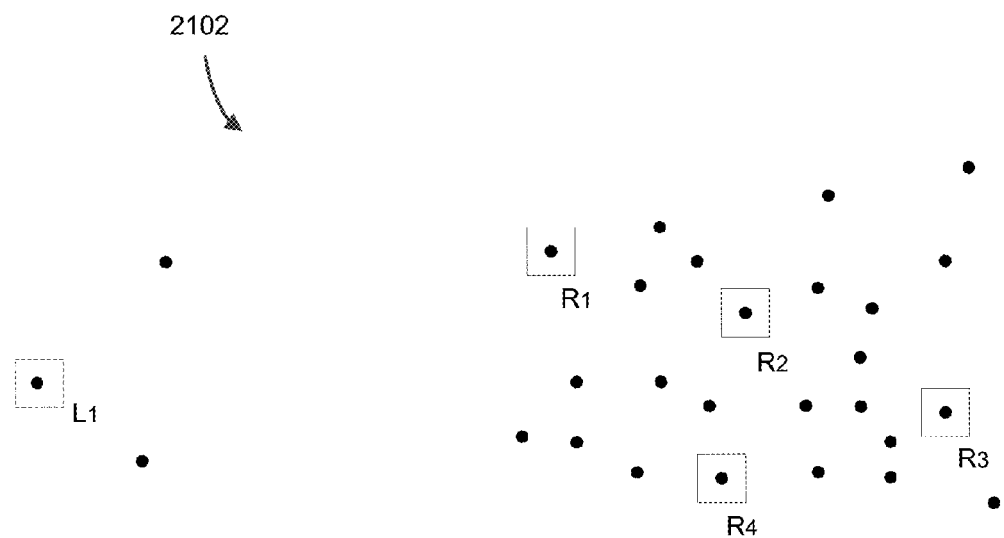
FIG. 23C shows point $P_2$ as new MM landmark point $L_1$ in this example.

Thus, with the longest landmark distance, $P_2$ is maximally far away from the random landmarks relative to the other non-landmark points and, at step 2014, landmark assignment module 1912 adds $P_2$ to the set of random landmark points (or seed landmarks) to generate a new set of landmark points. Thus, there is an initial set of randomly selected landmark points (R) and max-min landmark points (MM) calculated along the way are subsequently added to R to generate a set of landmarks (L). Accordingly, FIG. 23C shows point $P_2$ as new MM landmark point $L_1$.

Figure 23D:
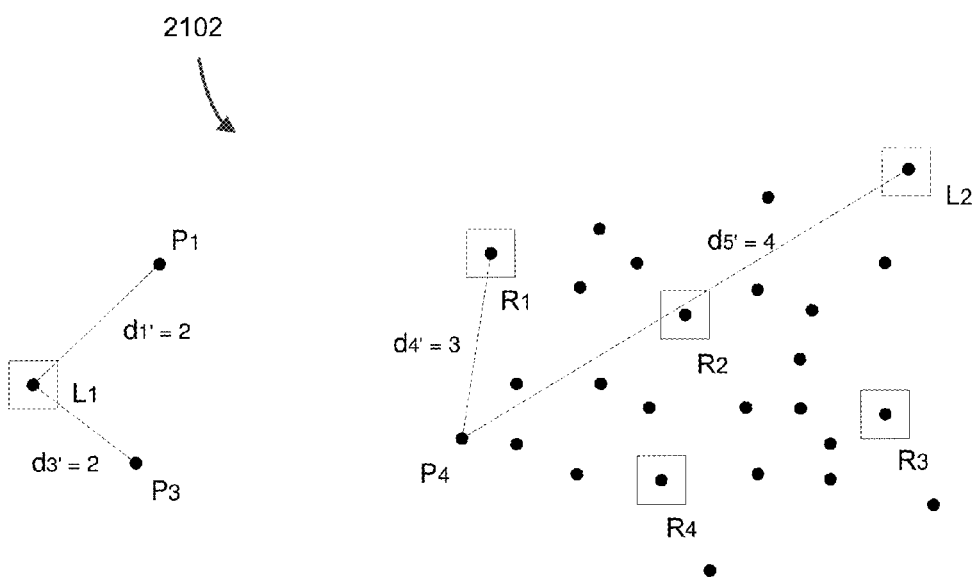
FIG. 23D shows subset with $L_1$ as a new landmark where the distances between various points have been calculated.

In various embodiments, this process may start over to identify and add a second most maximally far away point to the set of landmark points after $L_1$ has been added to the initial set of randomly selected landmark points (R). Thus, steps 2002 to 2014 can be repeated with $L_1$ included into the set of landmark points (L) when determining the landmark distances for each point. Accordingly, FIG. 23D shows subset 2102 with $L_1$ as a new landmark where the distances between various points have been calculated. In this example, $R_1$ is no longer the closest landmark to points $P_1$ and $P_3$ with the inclusion of $L_1$ and $L_2$. For example, $P_1$ is now a distance $d_{1'}=2$ from its nearest landmark $L_1$ and $P_3$, whose nearest landmark is also $L_1$, is now a distance $d_{3'}=2$ from $L_1$. Further, as shown in FIG. 23D, the distance $d_{4'}=3$ between point $P_4$ and $R_1$ and the distance $d_{5'}=4$ between point $P_4$ and newly added MM landmark point $L_2$ since $d_{5'}$ is larger than $d_{4'}$, $d_{3'}$, and $d_{1'}$.

In one example, a method for generating a set of landmark points can utilize a process called PROCESS_x_AND_l(X, l), for example, that determines the distances between each point and each landmark point, identifies the closest landmark for each point (dClosest[ ]), and updates an array of dClosest[ ] for each point. Subsequently, a process called FIND_NEXT_L(l) can add a new MM landmark at l to the set of landmarks (L). For example, PROCESS_x_AND_l(x, l) can be implemented as follows:

```
double dist = distance(x, L[l]);
if (dist < dClosest[x]) dClosest[x] = dist;
```

FIND_NEXT_L(l) can be implemented as follows:

```
double closestD = -Double.MAX_VALUE;
for (int x = 0; x < |X|; x++) {
    if (!inL[x] && (dClosest[x] > closestD)) {
        closestD = dClosest[x];
        L[l] = x;
```

Thus, referring back to FIG. 23D, the method for generating a set of landmark points can proceed by first selecting random landmarks $R_1$, $R_2$, $R_3$, and $R_4$ and, thereafter, successively calling PROCESS_x_AND_l(x,l) for each point in metric space 2100 (e.g., each x in X on every l in L). Accordingly, a first portion of a method for generating a set of landmark points can be implemented as follows:

```
for l = 0, l < |R| l++
    do
        for x = 0, x < |X|, x++
            do
                PROCESS_x_AND_l(x,l)
```

Once the first portion is completed, the remaining landmark points can be looped over one at a time to find the next MM landmark in a second portion of the method:

```
for l = |R|, l < |L|, l++
  do
  FIND_NEXT_L(l)
    for x = 0, x < |X|, x++
    do
      PROCESS_x_AND_l(x,l)
    done
```

If the landmark selection process is improperly implemented, it can be inefficient for large spaces. For example, the |L|×|X| matrix can be huge and, if the distance calculations are not ordered properly, the computation can page wildly. For example, as described above, the landmark selection process iterates |L| (i.e., the number of landmark points) times over the data X (i.e., the number of data points) of metric space 2100. If the data space X does not fit into available memory on a computer system, the data in X gets read repeatedly from disc, with slow results.

It will be appreciated that landmarks may be used instead of an entire data set for analysis. The landmark set may approximate the behavior of a larger data set thereby allowing analysis of the landmark set for computational efficiency and speed.

The landmark process may be used at many different stages in topological analysis (examples of topological analysis are described herein). For example, landmarks of data points mapped to a reference space may be identified. The landmark set may then be utilized to create a visualization as also described herein. In one example, as discussed regarding FIG. 8, the input module 314 may receive data (e.g., data S). In one example, a user identifies a data structure and then identifies ID and data fields. Data S may be based on the information within the ID and data fields. It will be appreciated that data S may be a finite metric space, or a generalization thereof, such as a graph or weighted graph.

The input module 314 may generate reference space R. In one example, reference space R may be a well-known metric space (e.g., such as the real line). The reference space R may be defined by the user. The analysis module 320 may generate a map ref( ) from S into R. The map ref( ) from S into R may be called the "reference map."

A landmark set of data points may be determined using methods described herein. The landmark set of data points may be a subset of the data points mapped into the reference space. For example, a first subset of the data points in the map may be selected to generate an initial set of landmarks. Each data point of the first subset may define a landmark point.

As discussed herein, for each non-landmark data point, first data point distances between a respective non-landmark data point and each landmark point of the initial set of landmarks may be calculated, a first shortest data point distance from among the first data point distances between the respective non-landmark data point and each landmark point of the initial set of landmarks may be identified, and the first shortest data point distance as a first landmark distance for the respective non-landmark data point may be stored. Subsequently, one or a group (i.e., a predetermined number of) non-landmark data point(s) with longest first landmark distance(s) in comparison with other first landmark distances of other non-landmark data points may be identified. The non-landmark data point(s) associated with the longest first landmark distance as a first landmark point may be added to the initial set of landmarks to generate an expanded set of landmark points.

The resolution module 318 may generate a cover of R based on the resolution received from the user (e.g., filter(s), intervals, and overlap—see discussion regarding FIG. 7 for example). The cover of R may be a finite collection of open sets (in the metric of R) such that every point in R lies in at least one of these sets.

Having computed, for each landmark point, which "cover tags" it is assigned to, for each cover element, $C_d$, the points may be constructed, whose tags included, as set S(d). This may mean that every landmark point s is in S(d) for some d, but some landmark points may belong to more than one such set. In some embodiments, there is, however, no requirement that each S(d) is non-empty, and it is frequently the case that some of these sets are empty. In the non-parallelized version of some embodiments, each landmark point x is processed in turn, and x is inserted into a hash-bucket for each j in ref_tags(t) (that is, this may be how S(d) sets are computed).

The analysis module 320 may cluster each landmark S(d) based on the metric, filter, and the space S. In some embodiments, a dynamic single-linkage clustering algorithm may be used to partition S(d).

The visualization engine 322 may identify nodes which are associated with a subset of the partition elements of all of the landmark S(d) for generating a visualization. Of the sets of points that are used, two nodes intersect provided that the associated node sets have a non-empty intersection.

The visualization engine 322 may join clusters to identify edges (e.g., connecting lines between nodes). Once the nodes are constructed, the intersections (e.g., edges) may be computed "all at once," by computing, for each point, the set of node sets (not ref_tags, this time). That is, for each landmark s in S, node_id_set(s) may be computed, which is an int[ ]. In some embodiments, if the cover is well behaved, then this operation is linear in the size of the set S, and we then iterate over each pair in node_id_set(s). There may be an edge between two node_id's if they both belong to the same node_id_set( ) value, and the number of landmark points in the intersection is precisely the number of different node_id sets in which that pair is seen. This means that, except for the clustering step (which is often quadratic in the size of the sets S(d), but whose size may be controlled by the choice of cover), all of the other steps in the graph construction algorithm may be linear in the size of S, and may be computed quite efficiently.

The visualization engine 322 may generate the visualization of interconnected nodes.

The landmark process may be used at other stages in topological analysis. For example, nodes may be determined based on complex data using topological data analysis as described herein. The nodes may also be landmarked and a visualization may be generated that includes the nodes of landmark points. This subset of nodes may have in a manner similar to the larger set of all nodes.

In one example, as discussed regarding FIG. 8, the input module 314 may receive data (e.g., data S). In one example, a user identifies a data structure and then identifies ID and data fields. Data S may be based on the information within the ID and data fields. The input module 314 may generate reference space R. In one example, reference space R may be a well-known metric space (e.g., such as the real line). The analysis module 320 may generate a map ref( ) from S into R. The map ref( ) from S into R may be called the "reference map."

The resolution module 318 may generate a cover of R based on the resolution received from the user (e.g., filter(s), intervals, and overlap—see discussion regarding FIG. 7 for example). The cover of R may be a finite collection of open sets (in the metric of R) such that every point in R lies in at least one of these sets.

The analysis module 320 may cluster each data point S(d) based on the metric, filter, and the space S. In some embodiments, a dynamic single-linkage clustering algorithm may be used to partition S(d).

The visualization engine 322 may identify nodes which are associated with a subset of the partition elements of all of the data points S(d) for generating a visualization. Of the sets of points that are used, two nodes intersect provided that the associated node sets have a non-empty intersection.

The nodes may be landmarked. For example, an initial set of nodes may be identified as landmark nodes. For each non-landmark node, first data point distances between a respective non-landmark node and each landmark node of the initial set of landmarks may be calculated, a first shortest data point distance from among the first data point distances between the respective non-landmark node and each landmark node of the initial set of landmarks may be identified, and the first shortest data point distance as a first landmark distance for the respective non-landmark node may be stored. Subsequently, one or a group (i.e., a predetermined number of) non-landmark data point(s) with longest first landmark distance(s) in comparison with other first landmark distances of other non-landmark nodes may be identified. The non-landmark node(s) associated with the longest first landmark distance as a first landmark node may be added to the initial set of landmarks to generate an expanded set of landmark nodes.

The visualization engine 322 may join clusters to identify edges (e.g., connecting lines between nodes). Once the nodes are constructed, the intersections (e.g., edges) may be computed "all at once," by computing, for each point, the set of node sets. The visualization engine 322 may generate the visualization of interconnected nodes.

Figure 24A:
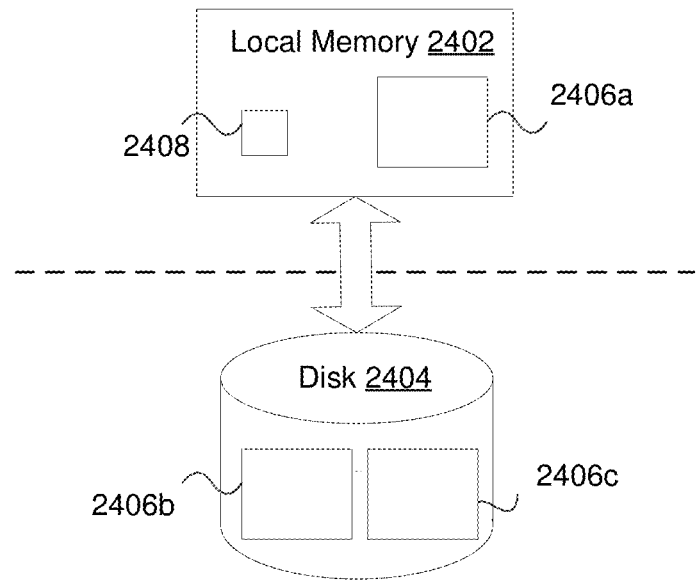
FIG. 24A shows an example wherein data in X does not fit into local memory (e.g., Random Access Memory (RAM)) and is, therefore, read off of long term storage.

FIG. 24A shows an example wherein data in X does not fit into local memory 2402 (e.g., Random Access Memory (RAM)) and is, therefore, read off of long term storage 2404. In this example, landmark set 2408 represents storage of the set of all landmark points and data point sets 2406a, 2406b, and 2406c represent three different portions of the data space X (e.g., each of data points sets 2406a, 2406b, and 2406c containing different data). Accordingly, in this example, landmark set 2408 and only a first set 2406a of data space X can fit in local memory 2402.

In the example discussed herein, landmark set 2408 could represent an amount of data points on the order of about 5,000 points and data point sets 2406a, 2406b, and 2406c could represent an amount of data points on the order of about 100 million+ data points. Thus, once data point set 2406a has been compared to landmark set 2408 to determine the distance calculations, data point set 2406a must be removed from local memory 2402 to make room for data point set 2406b. After removal of data point set 2406a from local memory 2402, data point set 2406b is read off disk 2404 and loaded into local memory 2402. Accordingly, once data point set 2406b has been compared to landmark set 2408 to determine those distance calculations, data point set 2406b is removed from local memory 2402 and data point set 2406c is read off disk 2404 and loaded into local memory 2402. The process of reading this much data off of disk 2404 creates significant latency.

Figure 24B:
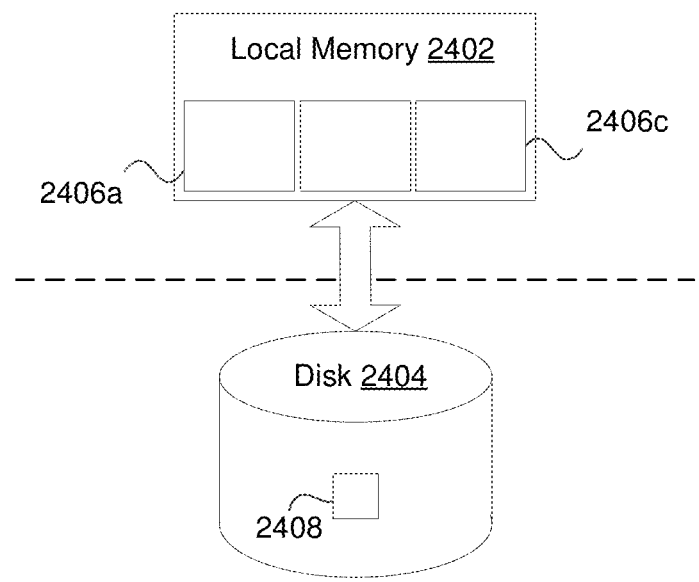
FIG. 24B shows an example wherein data point sets are stored in local memory instead of the landmark set in accordance with various embodiments.

Since the number of landmark points does not change until after a new landmark has been determined and added (i.e., after each iteration), the number of landmark points is effectively limited for each round of distance calculations and, thus, PROCESS_x_AND_l( ) may only depend on x (e.g., data point sets 2406a, 2406b, and 2406c). Therefore, PROCESS_x_AND_l( ) can be called in any order on x and the set L values (Landmark point values), provided that the process is being called on all landmark (landmark set 2408) and non-landmark point pairs (e.g., data point sets 2406a, 2406b, and 2406c). As a result, the first process described above may be reordered to process all landmark points (e.g., landmark set 2408) for each x (e.g., data point sets 2406a, 2406b, and 2406c) instead of all points in X for each landmark point L. Accordingly, FIG. 24B shows an example wherein data point sets 2406a, 2406b, and 2406c are stored in local memory 2402 instead of landmark set 2408 in accordance with various embodiments. Thus, instead of repeatedly reading the large amount of data associated with data point sets 2406a, 2406b, and 2406c off of disk 2404, the comparatively much smaller amount of data associated with landmark set 2408 is read off disk 2404. Thus, the first portion of a method for generating a set of landmark points may be reordered (STEP1A) and implemented as follows:

```
for x = 0, x < |X|, x++
do
    for l = 0, l < |R|, l++
    do
        PROCESS_x_AND_l(x,l)
    done
```

Since PROCESS_x_AND_l( ) only depends on x, a current state or snapshot of the set of landmarks can be stored in local memory 2402 and PROCESS_x_AND_l( ) can be altered to use that state when performing a next iteration of distance calculations. Accordingly, if that state fits into local memory 2402 along with, for example, J rows of X, and the reordered first portion (STEP1A) of the method for generating the set of landmarks and be run with only |X|/J page faults. For example, since the number of landmark points L is generally much smaller than the set of data points |X|, the number of page faults when scanning X with L in local memory 2402 is approximately the same as the number of page faults when scanning X without L. For example, if M is a number of rows of X which can be simultaneously stored in local memory 2402, then the number of page faults associated with the first portion of the method (STEP1) before reordering is approximately |L|*|X|/M and the number of page faults associated with the first portion of the method after reordering (STEP1A) is approximately |X|/(M−|L|).

Further, given T threads, the data points of X can be split into stripes such that at least T of these stripes can fit into local memory 2402 along with L. Accordingly, each thread of T can independently process a stripe, such that there are 'T versions' of STEP1A concurrently operating. As the x values are partitioned, contention is minimal and we see in practice speedups of a factor of T. Concurrent operations do not always finish precisely at the same time, thus, in one example, each thread may include spin-locks to acquire new a stripe in order. This can also enable the stripes to be fairly small and kept roughly together as X is iterated over.

The max-min landmark selection process for T threads is somewhat different, but it can be understood as a FIND_NEXT_L(1) followed by a STEP1 with only one landmark (which is equivalent to STEP1A, in this case) instead of a STEP2. This means that the end of each STEP1A thread can be synchronized to then run a FIND_NEXT_L( ) and then partition X into stripes and run the STEP1A piece in parallel. As FIND_NEXT_L( ) iterates over two (or more) arrays (e.g., one of booleans and another of doubles or floats), it may have paging issues only for truly gigantic spaces or machines with small amounts of memory.

Figures 25A, 25B:
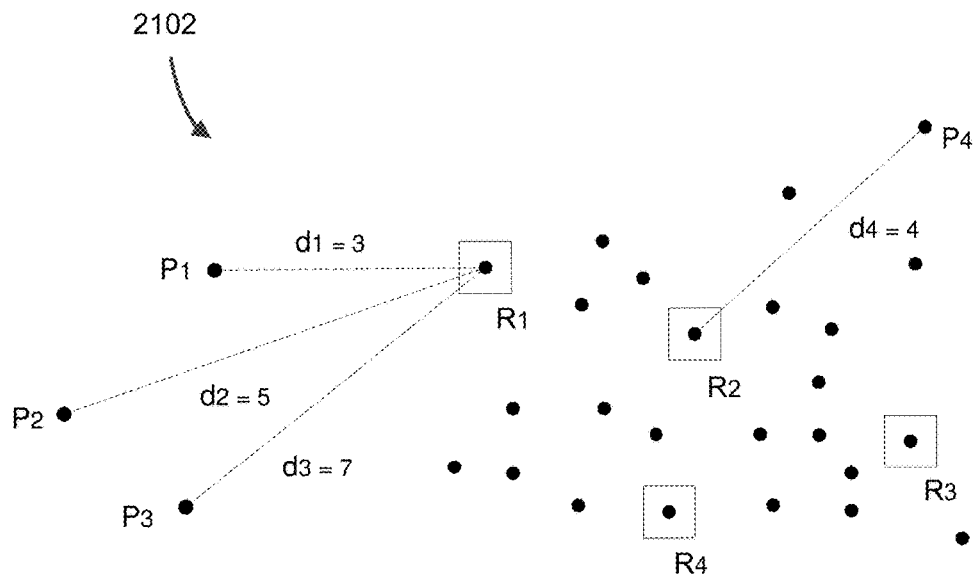
FIG. 25A shows subset with distances shown for points $P_1$, $P_2$, $P_3$, and $P_4$ to their respective closest random landmark ($R_1$, $R_2$, $R_3$, $R_4$).
FIG. 25B shows example shortest distances from each non-landmark point to each landmark point.
Figure 25C:
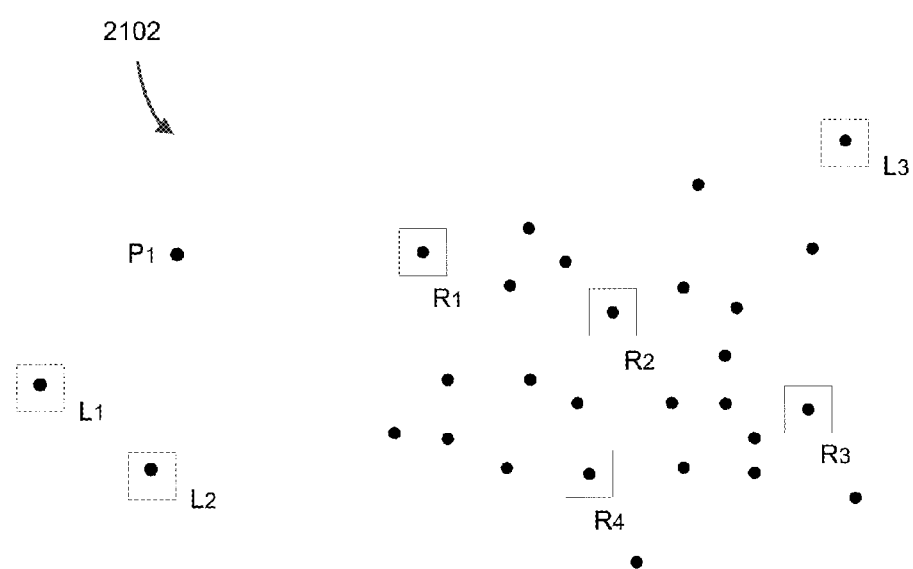
FIG. 25C shows points $P_2$, $P_3$, and $P_4$ as landmarks $L_1$, $L_2$, and $L_3$ in this example.

In various embodiments, instead of determining a single new landmark point for each iteration of the aforementioned method of generating a set of landmark points, multiple landmark points can be chosen at a time. FIGS. 25A-25C show a process for generating a set of landmark points wherein multiple landmark points are selected for each iteration of distance calculations described above. In at least one embodiment, for each iteration of distance calculations, the top "n" data points associated with the longest distances to a nearest landmark point could be selected. The number "n" could vary, such as with the size of data space X, or it could be fixed to select a top predetermined number (e.g., 5) of the most distant data points, for example, from a respective landmark point for each iteration of distance calculations.

FIG. 25A shows subset 2102 with distances shown for points $P_1$, $P_2$, $P_3$, and $P_4$ to their respective closest random landmark ($R_1$, $R_2$, $R_3$, $R_4$). In this example, distance $d_1$ between $P_1$ and $R_1$ is 3, distance $d_2$ between $P_1$ and $R_2$ is 5, distance $d_3$ between $P_3$ and $R_3$ is 7, and distance $d_4$ between $P_4$ and $R_2$ is 4 and these distances are shown in table 2550 of FIG. 25B. FIG. 25B shows example shortest distances from each non-landmark point to each landmark point.

In this example, points $P_2$, $P_3$, and $P_4$ are in a top "n" data points being selected for this iteration based on each of their corresponding distances to their nearest landmark point. For example, among an "n" number of landmark points being selected for this particular iteration, the distance $d_1$=3, between $P_1$ and $R_1$, is too short relative to other data points in subset 2102 and may not, therefore, be chosen for inclusion in the set of landmark points. Points $P_2$, $P_3$, and $P_4$, however, are chosen for inclusion in the set of landmark points with random landmark points ($R_1$, $R_2$, $R_3$, $R_4$).

Accordingly, FIG. 25C shows points $P_2$, $P_3$, and $P_4$ as landmarks $L_1$, $L_2$, and $L_3$ in this example. As can be seen in FIG. 25C, $L_1$ and $L_2$ are close together since they were selected without taking their relative distances to each other into consideration and at least one of them would not have been chose as a landmark point if only one landmark were chosen at a time. However, this process may work as an approximation and the landmark points may not necessarily need to be perfectly spaced when the collection of data points is large. One way to potentially avoid choosing landmarks that are too close to each other is by first selecting a single landmark in a first iteration, a few such as 5 landmarks in a second iteration, a single landmark again in a third iteration, and so on. However, even if a few landmark points end up being close to each other, when taken into account with all other landmarks, the space can still be effectively approximated.

In some embodiments, more than one landmark point can be selected at a time by executing STEP1A on all landmarks at once, further resulting in fewer iterations over X. In this example, identifying multiple MM landmarks at a time may be accomplished by noticing that values of dClosest[ ] decrease as more landmark points are added. Thus, the values of dClosest[x] may only stay the same or go down as more data points are added to the set of landmark points. The landmark at l is, thus, the x in dClosest[ ] at step l-1 which has the largest value. As a result, if x is the MM landmark at l, an obvious candidate for the MM landmark at l+1 may be the x' which has the second largest value in dClosest[ ] at l-1. In one example, if dClosest[x'] does not decrease, x' will be the landmark point chosen at l+1 using any of the aforementioned processes for selecting landmark points. In other words, if x' is further from x than from the closest of the previous l-1 landmark points, then it may be the l+1th landmark. This pruning can be extended by remembering some fixed number K of largest indices and values for dClosest[ ], and then pruning these by various heuristic processes. For instance, STEP2 from above can be altered as the following:

```
double dist = distance(x, L[l]);
if (dist < dClosest[x]) {
    dClosest[x] = dist;
    insertKLargest(x, dist);
```

In this example, insertKLargest( ) maintains a data structure which recalls the K-largest pairs (x,distance). We can then iterate over the K pairs, largest first, to recompute the dClosest[ ] values by adding the point with associated with the largest distance to the set of landmark points. Any values which remain larger than other dClosest[ ] values can be considered reliable and values which remain as the process continues to add additional points to the set of landmark points as the values of dClosest[ ] are adjusted along the way are themselves the landmark points this process is searching for. This process might fail to find any additional landmark points, however, as all the K-largest pairs might be part of a cluster eliminated by a newest landmark in the process. In practice, however, this process generally results in additional landmark points, and can reduce the number of iterations over X by the average number of landmarks generated.

In one example, the distance calculations can use only the smallest values of the distances for a given data point x, such that the number varies depending on the K in STEP2. The following method (STEP2A) is equivalent, and for certain spaces, can be more efficient:

```
double dist = distanceUpToLimit(x, L[l], KLargest(x));
if (dist < dClosest[x]) {
    dClosest[x] = dist;
    insertKLargest(x, dist);
```

In this example, distanceUpToLimit( ) will quit calculating the distance when it is known that the distance may be "too large to be interesting." Since many points can be considered relatively far away, and spaces of dimensionality in the millions are not uncommon (and those in the thousands and tens of thousands are routine), this can lead to significant performance improvements.

In another example, the distances within a stripe can be computed in a single pass where the computation for each pairwise distances are interleaved, rather than computed serially. Such a process can be utilized at a low level and useful when using a smaller number of threads and metrics for which the distances can make use of specialized vectorization hardware. This approach has the potential to deliver improved performance, as it eliminates a lot of the redundant computations introduced when each distance in a stripe is computed serially. Testing, however, indicates that under load, the performance advantage associated with interleaving is marginalized, as threads spend an increasing amount of time waiting for the memory subsystem to respond.

Accordingly, interleaving, in effect, may do a kind of loop unrolling at the lowest level of the metric calculation. For example:

```
double l2(double *in0, double *in1, int len) {
    double accum = 0;
    for (int i = 0; i < len; i++) {
        accum += (in0[i] - in1[i]) * (in0[i] - in1[i]);
    }
    return sqrt(accum);
}
void interleaved_l2(double *x0, double *x1, double *x2,
double *x3, double *y, int len, double *accum) {
    double accum0 = 0, accum1 = 0, accum2 = 0, accum3 = 0;
    for (i = 0; i < len; i++) {
        double yval = y[i];
        accum0 += (x0[i] - yval) * (x0[i] - yval);
        accum1 += (x1[i] - yval) * (x1[i] - yval);
        accum2 += (x2[i] - yval) * (x2[i] - yval);
        accum3 += (x3[i] - yval) * (x3[i] - yval);
    }
    accum[0] = sqrt(accum0);
    accum[1] = sqrt(accum1);
    accum[2] = sqrt(accum2);
    accum[3] = sqrt(accum3);
```

In this example, "yval" does not need to be reloaded and the process was able to avoid doing three of the four loop checks. The larger "len" is the more this will matter. Thus, in this example, the distances may all be computed in a single pass where the computation of each pairwise distance was interleaved, rather than computed serially. Accordingly, this approach eliminates some redundant computations introduced when each distance in a stripe is computed serially, thereby, increasing computational efficiency.

Systems and methods described herein may be utilized in big data analysis. Big data is a term that refers to data sets that are large and/or complex such that traditional data processing of the prior art may be inadequate or limited. Massive data sets may include hundreds of thousands, millions, or even billions (or more) data points and/or any number of characteristics per data point. There may be significant hardware, service, and/or financial limitations that must be considered when attempting to analyze large data sets (e.g., up to an including massive data sets as described above).

For example, system resource constraints, network limitations, service constraints, and/or algorithmic limitations (within a larger analytical framework) may impact analysis of large data sets. One or more of these limitations (e.g., insufficient memory) may cause system failure before large data sets are analyzed. Alternately, one or more of these limitations may slow analysis to the point of impracticality. As a result, when considering analyzing large data sets (including how a large data set is to be analyzed), system resource constraints, network limitations, service constraints, and/or algorithmic limitations.

A system resource is any physical or virtual component of limited availability within a computer system. Examples of physical system resources that may have limitations of access and/or performance include, but are not limited to, central processing units (CPUs), random access memory (RAM), hard disk, cache space (e.g., CPU cache, MMU cache), network throughput, electrical power, input/output operations, and the like. Virtual system resources may include but are not limited to files (e.g., file handles), network connections (e.g., network sockets), and memory.

Resource management may include, but is not limited to resource leaks (e.g., releasing a resource when a process has finished using it) and resource contention (when multiple processes wish to access a limited resource).

Network limitations include, but are not limited to, limitations of bandwidth, capacity, performance, and/or the like used for transferring data from one digital device to another. For example, when transferring all or parts of large data sets for analysis or during analysis, network limitations may cause data transfer to fail or to be too slow to be impractical. Network performance limitations may also impact system resources. For example, even if data sets may be transferred across a network, if the performance is not sufficient, system resources may fail or become unstable (e.g., receiving too much data or receiving data too slowly).

Service constraints may include limitations on usage of services provided by others that are used for data analysis. For example, cloud servers (e.g., servers available over the internet) provided by third parties may be used for data analysis. Service providers, however, typically charge for performance including quality of performance. As a result, not only must server and performance limitations be considered when selecting one or more service providers (e.g., and selecting one or more servers of a service provider based on performance to perform all or part of the analysis), server and performance limitations of these servers may be considered for potentially impacting analysis. Further, the costs of using servers may be considered in performing big data analysis. Costs associated with server and performance limitations may include, but are not limited to, cloud constraints, server running hours, storage costs, snapshot costs, read and write request costs, archiving costs, database running costs, database transaction costs (IO), and/or data transfer costs (including within a deployment and outside of a deployment). Financial constraints may render analysis impractical.

Algorithmic limitations may also be considered when determining how to analysis large data sets. Often an issue in optimization (e.g., "Big-O" problems), algorithmic efficiency may relate to the time it takes for the algorithm to run as a function of input size. Algorithmic limitations may slow analysis of large data sets or stop analysis completely.

Multiple systems (e.g., local digital devices and/or digital devices over a network) may be used on different parts of a large data set and/or perform portions of analysis. Each system, including constraints in data transfer, may have limitations that impact performance or capability. Similarly, multiple analytics programs and/or other resources may be impacted by the performance of one or more system resource constraints, network limitations, service constraints, and/or algorithmic limitations. As a result, efficiencies and handling may be considered for speed and performance when planning to use digital devices, analytics programs, and/or other resources that work together.

Landmarking data sets, as described herein (particularly with the discussion regarding FIGS. 19-25A-C), describe systems and methods for generating a landmark data set from an original data set. The landmark data set is generated to potentially include insights, information, and/or behavior of the larger original data set. Landmarking, as described herein, may be used as a process for improving performance and/or overcoming system resource constraints, network limitations, service constraints, and/or algorithmic limitations. For example, landmarking one or more large data sets of analysis may be used to increase speed and/or enable analysis of large data sets when analyzing the entire data set without landmarking is unwieldy, impractical, and/or not possible. Landmarking may also enable more efficient use of computational resources even if the entire data set may be analyzed without significant constraint.

It will be appreciated, however, that data sets may be so large that even landmarking a large data set and/or analyzing such landmarks may be impractical in view of system resource constraints, network limitations, service constraints, and/or algorithmic limitations. Some data sets may be sufficiently massive such that computational resources may be unable to load data into memory, process the data, store the data, generate a visualization, and/or transfer data to identify all landmarks. System resource constraints, network limitations, service constraints, and/or algorithmic limitations may be considered when selecting digital devices to use, determining how landmarking is to be performed, and/or determining how to perform analysis using the landmarks.

In this example, this process has at least two scalability bottlenecks that become problematic when operating on large data sets (e.g., data sets that contain billions of rows and/or are terabytes in size): 1. On a very large set of points X computing the list of functions on X can be computationally prohibitive. 2. Clustering points within each bucket can be a problem if the number of points in the bucket is very large. Some embodiments describe example procedures to construct topological summaries at scale.

In one example solution, a process of topological summary construction can be employed and/or modified with one or more of the following objectives in mind:

Prevent an explosion in computation cost as the size of the dataset grows

Figure 26:
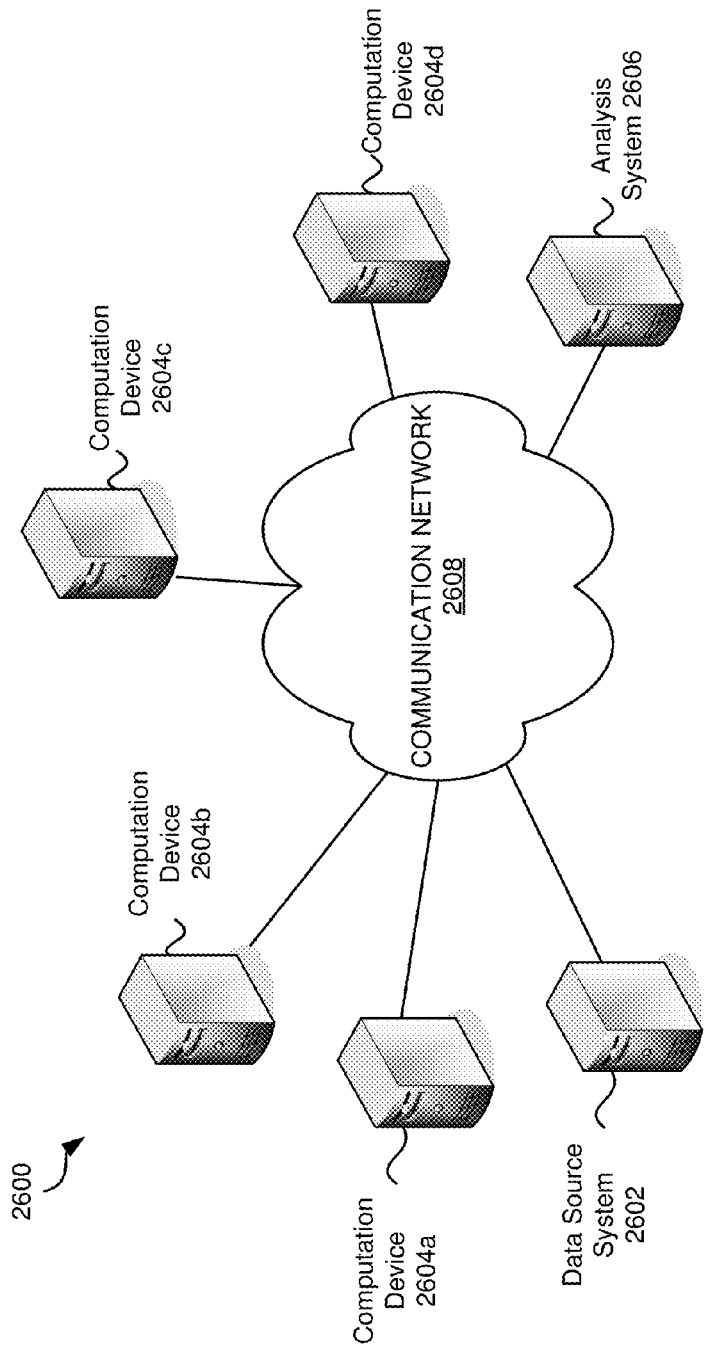
FIG. 26 is an example environment in which embodiments may be practiced.

Be amenable to division into a sub-jobs that can more easily run on commodity compute boxes with limited memory resources; horizontally scalable out-of-core processing with reduced or minimal inter-node communication or synchronization Avoid expensive data shuffling across terabyte files—such as required in step 3 of the original flow FIG. 26 is an example environment 2600 in which embodiments may be practiced. In various embodiments, landmarking, data analysis and/or generation of an interactive visualization may be performed locally (e.g., with software and/or hardware on a local digital device), across a network (e.g., via cloud computing), or a combination of both. In many of these embodiments, a large data set may be distributed and/or landmarked (e.g., identifying and/or determining landmark points in a large data set and/or portions of a large data set discussed herein) by any number of computation devices (e.g., computation devices 2604a-d).

Environment 2600 comprises a data source system 2602, computation devices 2604a-d, an analysis system 2606, and a communication network 2608. Environment 2600 depicts an embodiment wherein functions are performed across a network. In this example, the user(s) may take advantage of cloud computing and/or computation devices accessible over a network.

The data source system 2602, computation devices 2604a-d, and the analysis system 2606 may each be any digital device or any number of digital devices. A digital device is any device that includes memory and a processor. Digital devices are further described in FIG. 18. The data source system 2602, computation devices 2604a-d, and the analysis system 2606 may be any kind of digital device that may be used to access, analyze and/or view data including, but not limited to a server, desktop computer, laptop, notebook, or other computing device.

Although only one device is depicted in FIG. 26 for each of the data source system 2602, computation devices 2604a-d, and the analysis system 2606, it will be appreciated that there may be any number of devices. For example, the data source system 2602 may comprise a system including any number of digital devices that are local or remote from each other (e.g., accessible over a network that may include or may not include communication network 2608). Similarly, each computation devices 2604a-d may include any number of digital devices that are local or remote from each other (e.g., accessible over a network that may include or may not include communication network 2608). Still further, the analysis system 2606 may include any number of digital devices that are local or remote from each other (e.g., accessible over a network that may include or may not include communication network 2608).

The data source system 2602 may provide all or part of a large data set to be analyzed. In some embodiments, the data source system 2602 provides a part of the large data set to each of the computation devices 2604a-d and/or the analysis system 2606 for landmarking (e.g., a process to determine landmark points of all or a part of the data set). In this example, the data source system 2602 may provide one or more subsets of the large data set to each computation device 2604a-d and/or the analysis system 2606. Each subset may or may not contain data exclusive of other subsets of the large data set. In some embodiments, the data source system 2602 may perform landmarking and analysis of all or part of the data set (e.g., the data source system 2602 may be a computation device 2604a and/or an analysis system 2606).

It will be appreciated that the data source system 2602 may include any number of servers or devices that store all or part of a large data set. For example, the large data set may contain hundreds of thousands, millions, or billions of patient records to be analyzed. There may be any number of data source devices 2602 owned and/or operated by any number of health care service providers that may provide all or some of the data sets to be analyzed.

The data source system 2602 may provide and/or store all or part of the data set. In various embodiments, the data source system 2602 stores databases and/or other data structures. In one example the data source system 2602 may be or include a secure server wherein a user may store data over a secured connection (e.g., via hops). The data may be encrypted and/or backed-up. In some embodiments, the data source system 2602 is operated by a third-party such as AMAZON's S3 service.

The computation devices 2604a-d may include any number of digital devices that performs landmarking and/or data analysis (e.g., topological data analysis). For example, each computation device 2604a-d may select landmark points from a different subset of the original large data set. Landmarking of a data subset is described herein. There may be any number of computation devices 2604a-d (e.g., greater or less than 4) to landmark and/or analyze any number of data subsets.

The communication network 2608 may be any network that allows digital devices to communicate. The communication network 2608 may be or include the internet and/or include LAN and WANs. The communication network 204 may support wireless and/or wired communication.

The analysis system 2606 may include any number of digital devices configured to analyze data (e.g., all or part of the data set provided by the data source device(s) 2602). The analysis system 2606 may use topological data analysis on any number of the subsets of the data set, the entire data set, and/or landmark information (e.g., expanded landmark subsets of landmark points) received from the computation devices 2604a-d. Example functions of the analysis system 2606 are further described herein. The analysis server may be the analysis server 208 described herein (e.g., see FIG. 2).

In various embodiments, the analysis system 2606 may perform many functions to interpret, examine, analyze, and display data and/or relationships within data. In some embodiments, the analysis system 2606 performs, at least in part, topological analysis of one or more subsets large datasets applying metrics, filters, and resolution parameters chosen by the user.

The analysis system 2606 may generate graphs in memory, visualized graphs, and/or an interactive visualization of the output of the analysis. As discussed herein, in some embodiments, an interactive visualization allows the user to observe and/or explore relationships in the data. In various embodiments, the interactive visualization allows the user to select nodes comprising data that has been clustered. The user may then access the underlying data, perform further analysis (e.g., statistical analysis) on the underlying data, and/or manually reorient the graph(s) (e.g., structures of nodes and edges described herein) within the interactive visualization. The analysis system 2606 may also allow for the user to interact with the data, see the graphic result.

The graphs in memory and/or visualized graphs may also include nodes (e.g., graphical nodes or vertices) and/or edges as described herein. Graphs that are generated in memory may not be depicted to a user but rather may be generated in memory of a digital device. Visualized graphs are rendered graphs that may be depicted to the user.

In various embodiments, the analysis system 2606 may determine how to divide the data set to subsets. Further, the analysis system 2606 may determine a size for the initial subset of landmarks, the total number of landmarks to be determined for each subset of landmark point, and/or a total number of landmarks to be used for analysis. These determinations may be based on system resource constraints, network limitations, service constraints, and/or algorithmic limitations of any number of the data source system 2602, the computation devices 2604a-d, the analysis system 2606, and/or the communication network 2608. These processes are further described herein.

Figure 27:
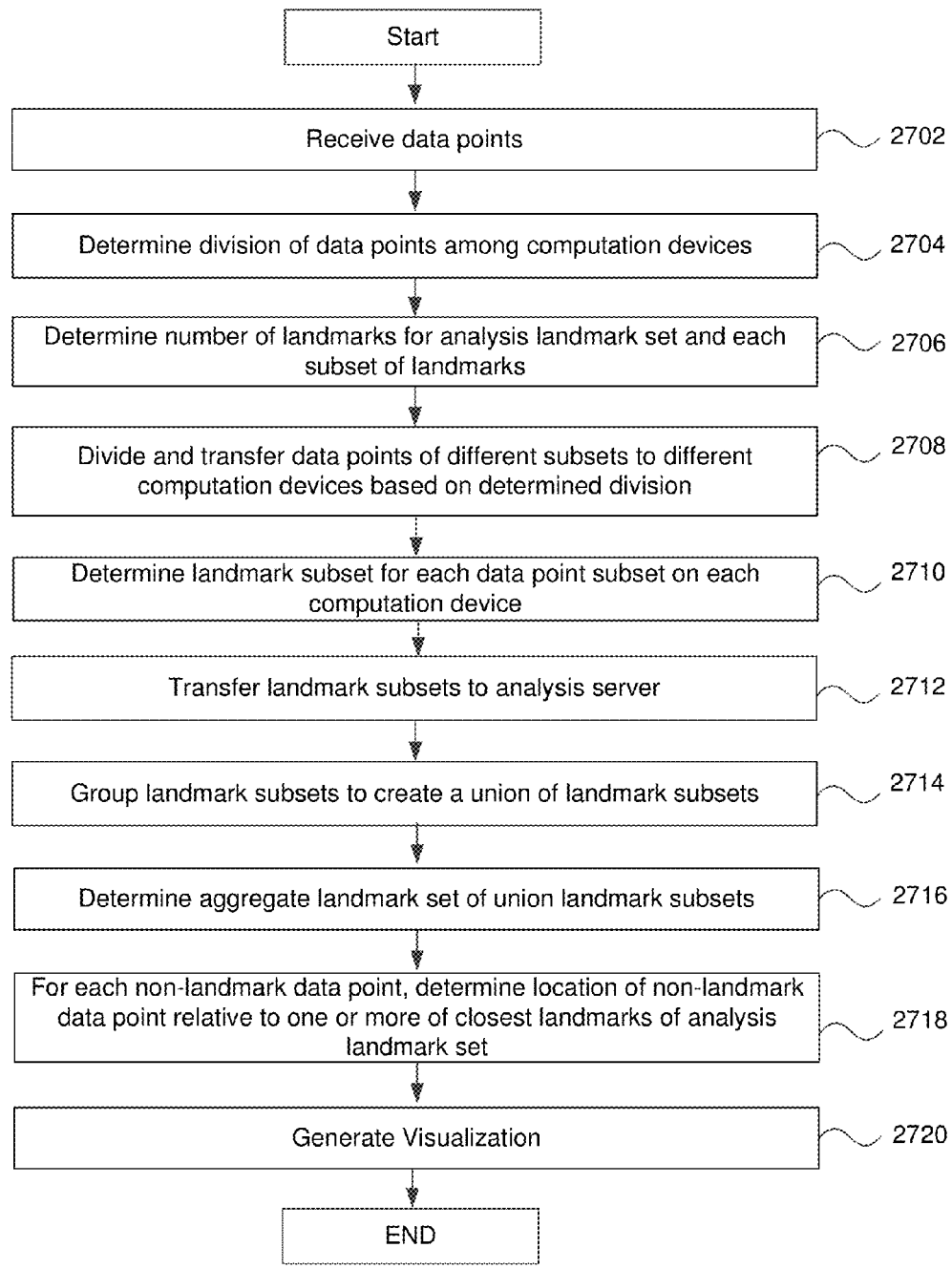
FIG. 27 is a flowchart for determining landmark points using any number of computation devices in some embodiments.

FIG. 27 is a flowchart for determining landmark points using any number of computation devices in some embodiments, As previously discussed, identification of landmark points may be viewed at a high level as follows:

From the set of points X, the analysis system 2606 constructs a subset of 'representative' points called the landmark set, L. The landmark set of points has the following properties:

a. For most points x in X, which is not in L, there exists a particular assigned landmark point in L, called L_x. For example, one simple way the analysis system 2606 may arrive at this assignment is by finding the landmark point which is closest (using a similarity or dissimilarity measure such as a proper distance metric) to x.

b. For some points x in X, there may be no assigned landmark point. In some embodiments, the analysis system 2606 may compare a distance between x and its closest landmark point to an anomaly threshold. If the distance is greater or equal to the anomaly threshold, then x may not be assigned a landmark point. Points x in X that have no assigned landmark may be categorized as "anomalies." Indeed, it is possible to envisage designing a separate workflow for detecting anomalies; if a user is interested in anomaly detection, the analysis system 2606 can be readily determined by returning to the user those points that are not assigned a closest landmark point.

In order to overcome slowness or constraints in computation, determining landmark points may be performed by any number of computation devices (e.g., computation devices 2604a-d). For example, it may be assumed that, in some implementations, a single digital device may readily compute the distance between any 2 points in the dataset—the entire dataset possibility being memory resident on a single device (e.g., data source system 2602). However, the size of the dataset may be thousands of times larger than the memory resources on any single digital device.

Accordingly, in this example approach, a digital device such as the analysis system 2606 or the data source system 2602 may divide the original data set X into a number of subsets. The subsets may be of fixed size or variable size. The data set may be sub-divided in any number of ways including, but not limited to random or pseudo-random (without replacement). Is the data set may be sub-divided based on any characteristic (e.g., field or column of the data set) or combination of characteristics).

These subsets, which may be as small as 100 MB each for example, may be each landmarked in isolation on a different computation device 2604 without consideration to the larger dataset. In some embodiments, this phase of the computation is eminently scalable, as any number of landmark subset computations may be executed in parallel if there are sufficient computational resources.

In some embodiments, once these "subset" landmarking operations are complete, if the total number of landmarks is still not tractable, the analysis system 2606 may optionally iteratively landmark the chosen landmark subsets until a manageable set of final landmarks are chosen.

In step 2702, the data source system 2602 may receive a set of data points (e.g., a data set). As discussed herein, the data source system 2602 may include or communicate with any number of devices that store all or part of the data set. The data set may be contained in any number of data structures. In one example, the data set (e.g., the original data set) is shown in FIG. 21A.

In step 2704, the analysis system 2606 or the data source system 2602 determines a division of data points among computation devices. In the following discussion, the analysis system 2606 is discussed as performing steps 2704-2708, however, it will be appreciated that the data source system 2602 may perform any number or all of these steps.

In various embodiments, the analysis system 2606 may determine division of data points among computation devices based on hardware characteristics of the computation device. For example, a computation device with greater capacity (e.g., network connectivity, memory, processing power, storage, and/or the like) may receive larger data points than other computation devices. In another example, the analysis system 2606 may determine division of data points among computation devices based on limitations of the computation devices, limitations of the network that allows communication between computation devices, limitations of the data source system 2602 to transfer the data, and/or the analysis system 2606 capability to analyze data (e.g., landmark points).

In various embodiments, the analysis system 2606 determines division of data points based on system resource constraints, network limitations, service constraints, and/or algorithmic limitations (within a larger analytical framework) as discussed herein. For example, a system resource is any physical or virtual component of limited availability within any number of computation devices 2604a-d).

Network limitations include limitations of the communication network 2608 including limitations on bandwidth, capacity, performance, and/or the like in transferring data from one digital device to another.

Service constraints may include limitations on usage of services provided by others that are used for data analysis. For example, cloud servers (e.g., servers available over the Internet) may be utilized as computation devices. As a result, not only computation device performance limitations be considered when selecting one or more service providers (e.g., and selecting one or more computation devices of a service provider based on performance), computation devices limitations may be considered for potentially impacting analysis. Further, the costs of using servers may be considered in performing big data analysis. Costs associated with computation device performance limitations may include, but are not limited to, cloud constraints, server running hours, storage costs, snapshot costs, read and write request costs, archiving costs, database running costs, database transaction costs (TO), and/or data transfer costs (including within a deployment and outside of a deployment).

The analysis system 2606 may also consider algorithmic limitations in determining division of the data set among the computation devices 2604a-d. The analysis system 2606 may take into account limitations, constraints, and performance of multiple systems (e.g., local digital devices and/or digital devices over a network) that may be used on different parts of a large data set in determining division of the data set In various embodiments, the analysis system 2606 reviews any number of these constraints and limitations. In one example, the analysis system 2606 identifies those constraints and limitations of the computation devices 2604a-d and/or the analysis system 2606 that will either stop analysis and/or slow analysis below a desired threshold (e.g., four hours). The analysis system 2606 may determine division of the data set to enable analysis and/or determine divisions of the data set in view of speed and efficiency considerations over the constraints and/or limitations.

In step 2706, the analysis system 2606 determines a number of landmark points for an analysis landmark set and a number of landmark points for each subset of landmark points. The analysis landmark set may include each subset of landmark points. In some embodiments, the analysis landmark set includes landmark points selected from a union of the subsets of landmark points.

As discussed herein, each computation device 2604a-d may determine landmark points for a subset of the data set thereby creating an expanded landmark subset of landmark points. In one example implementation, each computation device 2604a-d may select an initial subset of landmark points and then may add landmark points until an expanded landmark subset of landmark points is obtained. The analysis system 2606 may determine the size (e.g., number) of initial subset of landmark points of each computation device 2604a-d and/or the number of landmark points for each expanded landmark subset of landmark points of each computation device 2604a-d. The size of the initial subset of landmark points may be the same or different for any number of computation devices 2604a-d. Similarly, the size of the expanded landmark subset of landmark points may be the same or different for any number of computation devices 2604a-d.

In various embodiments, the analysis system 2606 may determine the number of the initial set of landmark points and/or the expanded landmark set of landmark points based on hardware characteristics of the computation device. For example, a computation device with greater capacity (e.g., network connectivity, memory, processing power, storage, and/or the like) may determine a larger number of initial landmark points in the initial set and/or a larger number of landmark points in the expanded landmark set of landmark points of a larger number data points of a larger data subset than other computation devices. In another example, the analysis system 2606 may determine the number of landmark points in the initial set of landmark points and/or the expanded landmark set of landmark points based on system resource constraints, network limitations, service constraints, and/or algorithmic limitations. For example, the analysis system 2606 may determine a number of landmark points for the initial set or expanded landmark set based on limitations of the computation devices, limitations of the network that allows communication between computation devices, limitations of the data source system 2602 to transfer the data, and/or the analysis system 2606 capability to analyze data (e.g., landmark points).

In another example, the analysis system 2606 may also consider algorithmic limitations in determining the number of landmark points in the initial set of landmark points and/or the expanded landmark set of landmark points among the computation devices 2604a-d. The analysis system 2606 may take into account limitations, constraints, and performance of multiple systems (e.g., local digital devices and/or digital devices over a network) that may be used on different parts of a large data set in determining division of the data set It will be appreciated that that analysis system 2606 may determine the number of landmark points in the initial set of landmark points and/or the expanded landmark set of landmark points based on both performance strengths of different computation devices as well as limitations.

In various embodiments, the analysis system 2606 may determine a maximum number of data points the analysis system 2606 may analyze (e.g., a maximum number of an analysis landmark set and/or a maximum number of data points that can be added to nodes using the analysis landmark set as discussed herein). This determination may be based on system resource constraints of the analysis system 2606 (e.g., one or more digital devices of the analysis system 2606), network limitations (e.g., limitations communicating information from the data source system 2602 and/or the computation devices 2604a-d between each other and/or the analysis system 2606, or limitations of communicating information between different digital devices of the analysis system 2606), service constraints (e.g., one or more digital devices of the analysis system 2606), and/or algorithmic limitations (within a larger analytical framework of one or more digital devices of the analysis system 2606)).

In some embodiments, once a maximum number of data points of the analysis system 2606 is determined, a size of subsets of landmark points (e.g., expanded landmark point subsets and/or initial subsets of landmarks) may be determined for one or more computation devices 2604a-d. In one example, once the analysis system 2606 determines a maximum number of data points and/or landmark points that may be analyzed (e.g., based on performance characteristics and/or constraints of the analysis system 2606), then the analysis system 2606 may determine a size of the expanded landmark subset of landmark points based on the maximum number of data points and/or landmark points that may be analyzed (and/or based performance characteristics and/or based on limitations of the computation devices 2604a-d). Further, in some embodiments, once the analysis system 2606 determines size(s) of expanded landmark subset(s) of landmark points, then the analysis system 2606 may determine a subset size based on the expanded landmark subset of landmark points size (and/or based performance characteristics and/or based on limitations of the computation devices 2604a-d). In some embodiments, once a maximum number of data points of the analysis system 2606 is determined, size of subsets of data points may be determined for one or more computation devices 2604a-d.

In step 2708, the analysis system 2606 divides and transfers data points of different subsets to different computation devices based on determined division of data points. In some embodiments, the analysis system 2606 may divide and transfer data points to different computation devices based on size of subsets of landmark points (e.g., expanded landmark subset of landmark point and/or initial subsets of landmarks).

It will be appreciated that the analysis system 2606 may divide and transfer the data points in any number of ways. For example, the analysis system 2606 may provide commands to any number of data source devices of data source system 2602 to provide any number of data points as subsets to any number of computation devices. In various embodiments, the analysis system 2606 may provide commands to one or more computation devices 2604a-d to start identifying landmark points for the initial landmark set or the expanded landmark subset of landmark points if all or part of the subset is present on the computation device(s) 2604a-d.

In various embodiments, the analysis system 2606 may provide instructions and/or commands to any number of computation device(s) 2604a-d with instructions to set the size of the initial landmark set and/or the size of the expanded landmark subset of landmark points.

At step 2710, each computation device 2604a-d determines landmark points and generates expanded landmark subset of landmark points. For example, each computation device 2604a-d may receive a size of an initial landmark point subset and/or a size of an expanded landmark subset of landmark points. Each computation device 2604a-d may select (e.g., randomly) a number of landmark points from their respective data subset equal to the size of the initial landmark point subset. Each computation device 2604a-d may then add landmark points, respectively, to their particular initial landmark point subset to create respective expanded landmark subset of landmark points. This process is further discussed with regard to FIG. 28.

At step 2712, each computation device 2604a-d transfers their respective expanded landmark subset of landmark points to the analysis system 2606. In some embodiments, each computation device 2604a-d may provide all or some of the distances between each non-landmark point of its particular data subset and each landmark point of the particular expanded landmark subset of landmark points to the analysis system 2606.

In step 2714, the analysis system 2606 groups the f expanded landmark subset of landmark points from the computation devices 2604a-d to create a union of landmark subsets. Optionally, in step 2716, the analysis system 2606 may determine an analysis landmark set of union of landmark subsets by landmarking (e.g., finding landmark points of) the union of landmark subsets. For example, the analysis system 2606 may perform landmarking in a manner similar that performed by the computation devices in step 2710. In this example, the analysis system 2606 treats the union of landmark subsets as a subset of data points without any landmark points. The analysis system 2606 may select an initial subset of landmark points from the data points of the union of landmark subsets and then adds landmark points from the unselected points of the union of landmark subsets to create an analysis landmark set.

For example, the analysis system 2606 may determine an initial subset of landmark points. The analysis system 2606 may randomly selected landmark points (e.g., 5,000 points) from the union of landmark subsets. The initial landmark points may be selected in any number of ways. Selection may be random, may be "intelligently random" as discussed herein, be based on any number of data characteristics of data in the data subset or data set, and/or the like.

Subsequently, the analysis system 2606 may add additional landmarks in an intelligent fashion to reach a size for the analysis landmark set. For example, the analysis system 2606 may calculate data point distances between a respective non-landmark data point and each landmark point of the initial subset of landmark points.

The analysis system 2606 may identify the shortest data point distance from among the data point distances. In various embodiments, for each non-landmark point, the closest landmark point is identified. The analysis system 2606 may determine a longest landmark distance from among each of the shortest data point distances (or a longest landmark distance) from among each of the landmark distances. The analysis system 2606 may add the data point based on the longest landmark distance among each of the shortest data point distances to the analysis landmark set. The analysis system 2606 may add other data points in a similar fashion until a maximum size of the analysis landmark set is reached.

Alternately, in some embodiments, the analysis landmark set is the union of landmark subsets.

In step 2718, the analysis system 2606, for each non-landmark point of the original data set (e.g., from the data source system 2602), the analysis system 2606 may determine a location of a non-landmark data point relative to one or more of the closest landmarks of the expanded subset of landmark points.

In various embodiments, the analysis system 2606 may determine which node (e.g., graphical node or vertex) associated with one or more landmark points of the analysis landmark set of landmark points is to be associated with a non-landmark point of the original data set. In some embodiments, the analysis system 2606 may perform all or part of topological data analysis to identify nodes (e.g., graphical nodes or vertices) that include one or more landmark points of the analysis landmark set of landmark points. This process if further described with regard to FIG. 29.

The analysis system 2606 may then analyze each non-landmark point to determine which node the non-landmark point should be a member. In some embodiments, the analysis system 2606 may determine one or more of the closest landmark points from the analysis landmark set of landmark points to a non-landmark point. The analysis system 2606 may determine which nodes are associated with the closest one or more landmark points and assign the non-landmark point to the one or more nodes based on the determination. Embodiments of the process are described with regard to FIGS. 30-32.

Although the analysis system 2606 is discussed as determining which node associated with one or more landmark points of the analysis landmark set of landmark points is to be associated with a non-landmark point of the original data set, it will be appreciated that the analysis system 2606 may determine which node associated with one or more landmark points of the analysis landmark set of landmark points is to be associated with a non-landmark point of the union of landmark subsets (rather than the original data set).

In step 2720, the analysis system 2606 may generate a visualization of the nodes (e.g., graphical nodes or vertices) and edges between the nodes. The generation of the visualization may be done in any number of ways. The process is further described herein. In one example, the visualization may be generated in a manner similar to that discussed with regard to FIGS. 3, 4, and 8.

Figure 28:
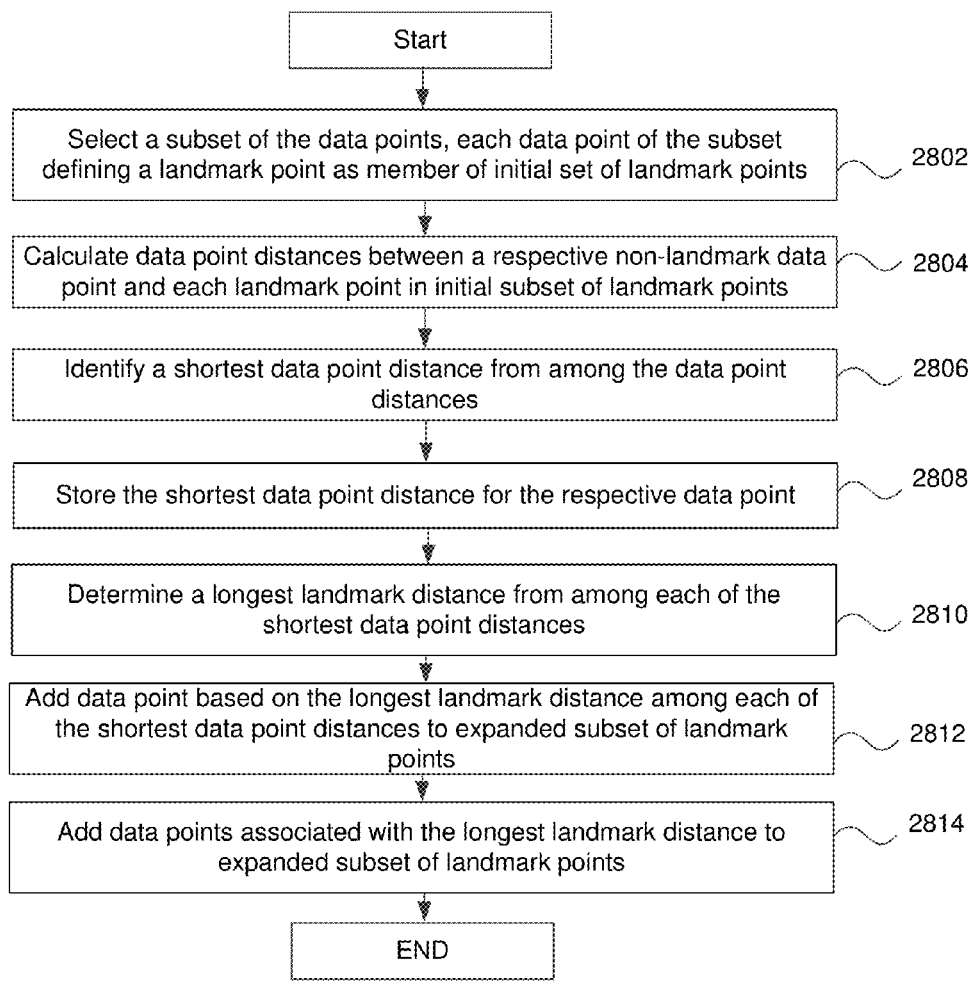
FIG. 28 is a flowchart for a computation device to create an expanded landmark subset of landmark points in some embodiments.

FIG. 28 is a flowchart for a computation device 2604*a* to create an expanded landmark subset of landmark points in some embodiments. In various embodiments, there may be any number of computation devices 2604*a-d* creating any number of expanded landmark subsets of landmark points. The flowchart of FIG. 29 describes a process for one computation device 2604*a*, however, it will be appreciated that any number of computation devices may each create a different expanded landmark subset of landmark points based on a different subset of data points.

In step 2802, the computation device 2604*a* selects a subset (e.g., a group) of data points, each data point of the subset defining a landmark point. The selected subset is a first sub-subset of landmarks. In some embodiments, the computation device 2604*a* may determine an initial subset of landmark points. The number of landmark points selected for the initial subset of landmark points (e.g., the size of the initial subset of landmark points) may be provided by the analysis system 2606.

For example, each computation device 2604*a-d* may select a random subset of individual data points as a first set (e.g., an initial set) of landmark points. As discussed herein, to illustrate this step, FIG. 21C shows example random landmarks $R_1$, $R_2$, $R_3$, and $R_4$ that have been randomly selected as initial landmarks. Since even a subset of data points may be large (e.g., million+ data points), points selected at random tend to be located in high density areas, which is a benefit when attempting to choose a subset of points that represent the characteristics of the larger space.

One or more computation devices 2604*a-d* may randomly selected landmark points equal to the size provided by the analysis system 2606. The initial landmark points may be selected in any number of ways. Selection may be random, may be "intelligently random" as discussed herein, be based on any number of data characteristics of data in the data subset or data set, and/or the like.

Subsequently, each computation device may add additional landmarks in an intelligent fashion to reach an expanded landmark subset of landmark points. In step 2804, the computation device 2604*a* calculates data point distances between a respective non-landmark data point and each landmark point of the initial subset of landmark points. For example, for each non-landmark point, a computation device 2604*a* may calculate distances between that particular non-landmark point and each landmark point of that computation device's particular initial landmark point subset. As used herein, the distances between landmark points and individual data points 2104 are referred to as data point distances. As discussed herein, FIG. 21D shows lines corresponding to data point distances to each landmark for three points ($P_1$, $P_2$, and $P_3$). It should be appreciated that, in various embodiments, the data point distances for all other points other than $P_1$, $P_2$, and $P_3$ and the landmarks are also calculated, but of clarity and illustrative purposes, the lines shown in FIG. 21D have only been drawn for $P_1$, $P_2$, and $P_3$.

Accordingly, in this example, each distance between $P_1$ and $R_1$, $R_2$, $R_3$, and $R_4$ is calculated, each distance between $P_2$ and $R_1$, $R_2$, $R_3$, and $R_4$ is calculated, etc. until the distances between each non-landmark point and all the landmarks are calculated. FIGS. 22A and 22B show this process in more detail.

FIG. 22A shows example data point distances between point $P_1$ and random landmarks $R_1$, $R_2$, $R_3$, and $R_4$. In this example, distance $d_1$ between $P_1$ and $R_1$ is 3, distance $d_2$ between $P_1$ and $R_2$ is 5, distance $d_3$ between $P_1$ and $R_3$ is 7, and distance $d_4$ between $P_1$ and $R_4$ is 6. In various embodiments, the landmark distance for a respective non-landmark point is defined as the shortest distance to its nearest landmark or the shortest data point distance. In this example, distances $d_1$, $d_2$, $d_3$, and $d_4$ are compared to each other to determine which is the shortest distance to a landmark from $P_1$. In this example, distance $d_1$, between $P_1$ and $R_1$, is the shortest distance and, thus, defined as landmark distance 2202 for $P_1$. Accordingly, $R_1$ is the closest landmark to $P_1$ with corresponding landmark distance 2202 (i.e., $d_1=3$).

Similarly, FIG. 22B shows example distances between point $P_2$ and random landmarks $R_1$, $R_2$, $R_3$, and $R_4$. In this example, distance $d_5$ between $P_2$ and $R_1$ is 5, distance $d_6$ between $P_2$ and $R_2$ is 5, distance $d_7$ between $P_2$ and $R_3$ is 9, and distance $d_8$ between $P_2$ and $R_4$ is 8. As above, distances $d_5$, $d_6$, $d_7$, and $d_8$ are compared to each other to determine which is the shortest distance to $P_2$'s nearest landmark, which is distance $d_5$. Accordingly, distance $d_5$ between $P_2$ and $R_1$ is landmark distance 2204. Thus, $R_1$ is also the closest landmark to $P_2$ at landmark distance 2204 (i.e., $d_5=5$), in this example.

Accordingly, the distance calculations described in FIGS. 22A and 22B are, thus, calculated for $P_3$ and every other non-landmark point in metric space 2100 and the distance calculations may be stored. For example, FIG. 22C shows an example table 2250 wherein distances for each point are stored. Although FIG. 22C depicts a table, it will be appreciated that any data structure(s) or combination of data structure(s) may be utilized. Further, although table 2250 includes all distances from P1 to each landmark, it will be appreciated that, in some embodiments, a subset of the distances may be stored. In one example, only the shortest distance between P1 and the closest landmark may be stored.

Further, in this example, only the distances for points $P_1$ and $P_2$ are shown, but it should be appreciated that such a table or array would include distances for each non-landmark point. Thus, in one embodiment, table 2250 stores the distances for each point to each landmark in metric space 2100. From these distances, a landmark distance (e.g., shortest distance to a nearest landmark) for each point may be identified and compared to generate a second set of landmark points. This process is discussed further with respect to FIGS. 23A-23D.

In step 2806, the particular computation device 2604*a* may identify the shortest data point distance from among the data point distances. FIG. 23A shows example landmark distances for points $P_1$, $P_2$, and $P_3$ to landmark $R_1$ which can be used to demonstrate the selection of additional landmark points. For example, landmark distance identification module 1906 determines for each point which landmark point is the closest landmark point for that respective point. This may include, for example, comparing the distance values $d_n$ from table 2250 for each point to determine which distance $d_n$ is the shortest. Accordingly, in this example, the shortest between a landmark and $P_1$ is 3 (i.e., between $P_1$ and landmark point $R_1$) and the shortest distance to a landmark point from $P_2$ is 5 which is also to landmark point $R_1$.

Such an operation may use an indexable state for X (i.e., points such as $P_1$, $P_2$, and $P_3$ in metric space 2100), an indexable array for L (e.g., L[1] is the index in X of the l'th landmark) where each random landmark point $R_n$ and subsequently determined landmark point is in L, and dClosest [x] which records the shortest distance between X[x] (i.e., $P_1$, $P_2$, $P_3$, etc.) and a respective closest landmark point, and in L[ ] with is true if x is in L.

In step 2808, the particular computation device 2604a stores the shortest distance from each non-landmark point to a landmark point (or the distance to the nearest landmark) in an array. FIG. 23B shows example shortest distances from each non-landmark point to each landmark point. In FIG. 23B, table 2350 contains the shortest distances between each data point $P_1$, $P_2$, and $P_3$ and its closest landmark, respectively.

In various embodiments, for each non-landmark point, the closest landmark point is identified. As a result, a list of non-landmark points that identify the same landmark point as the closest landmark point may be identified. For example, for each such landmark point, a table such as table 2350 may be generated that identifies the non-landmark points that identify the same particular landmark point as being closest. The table 2350 may further identify distances between those non-landmark points and the same particular landmark point. In this example, table 2350 may contain the shortest distances between data points $P_1$, $P_2$, and $P_3$ and landmark point $R_1$. data point and only one landmark $R_1$ In step 2810, the particular computation device 2604a may determine a longest landmark distance from among each of the shortest data point distances (or a longest landmark distance) from among each of the landmark distances. For example, returning to FIG. 23A, random landmark point $R_1$ is the landmark nearest to points $P_1$, $P_2$, and $P_3$ and, thus, the landmark distance $l_n$ (i.e., the distance to a nearest landmark) for each of these points is its respective distance to $R_1$, which may be stored in table 2350. Thus, in this example, the landmark distance for $P_1$ is $l_1=3$, the landmark distance for $P_2$ is $l_2=5$, and the landmark distance for $P_3$ is $l_3=4$. Accordingly, landmark distance comparison module 1910 compares these distances to identify the longest distance which, in this example, is $l_2=5$ shown circled in FIG. 23B, belonging to point $P_2$.

Thus, with the longest landmark distance, $P_2$ is maximally far away from the random landmarks relative to the other non-landmark points and, at step 2812, the particular computation device 2604a adds $P_2$ to the set of random landmark points (or seed landmarks) to generate a new set of landmark points the data point is added to the first sub-subset of landmarks to expand the first sub-subset of landmarks to generate an expanded set of landmarks). Thus, there is an initial set of randomly selected landmark points (R) and max-min landmark points (MM) calculated along the way are subsequently added to R to generate a set of landmarks (L) (e.g., the expanded landmark subset of landmark points). Accordingly, FIG. 23C shows point $P_2$ as new MM landmark point $L_1$. The addition of the new data point to the initial subset of landmark points creates an expanded landmark subset of landmark points.

In step 2814, the computation device 2604a may add other data points to the expanded landmark subset of landmark points (e.g., the first sub-subset of landmarks) in a similar fashion until a maximum size (e.g., a predetermined number of members) of the expanded landmark subset of landmark points is reached. For example, in various embodiments, this process may start over to identify and add a second most maximally far away point to the set of landmark points after $L_1$ has been added to the initial set of randomly selected landmark points (R). Thus, these steps can be repeated with $L_1$ included into the set of landmark points (L) when determining the landmark distances for each point. Accordingly, FIG. 23D shows subset 2102 with $L_1$ as a new landmark where the distances between various points have been calculated. In this example, $R_1$ is no longer the closest landmark to points $P_1$ and $P_3$ with the inclusion of $L_1$ and $L_2$. For example, $P_1$ is now a distance $d_1 = 2$ from its nearest landmark $L_1$ and $P_3$, whose nearest landmark is also $L_1$, is now a distance $d_3 = 2$ from $L_1$. Further, as shown in FIG. 23D, the distance $d_4 = 3$ between point $P_4$ and $R_1$ and the distance $d_5 = 4$ between point $P_4$ and newly added MM landmark point $L_2$ since $d_{5'}$ is larger than $d_{4'}$, $d_{3'}$, and $d_{1'}$.

It will be appreciated that the expanded landmark subset of landmark points may approximate the behavior of the larger data subset thereby allowing analysis of and/or using the expanded landmark subset of landmark points to overcome limitations, for computational efficiency, and/or speed.

Figure 29:
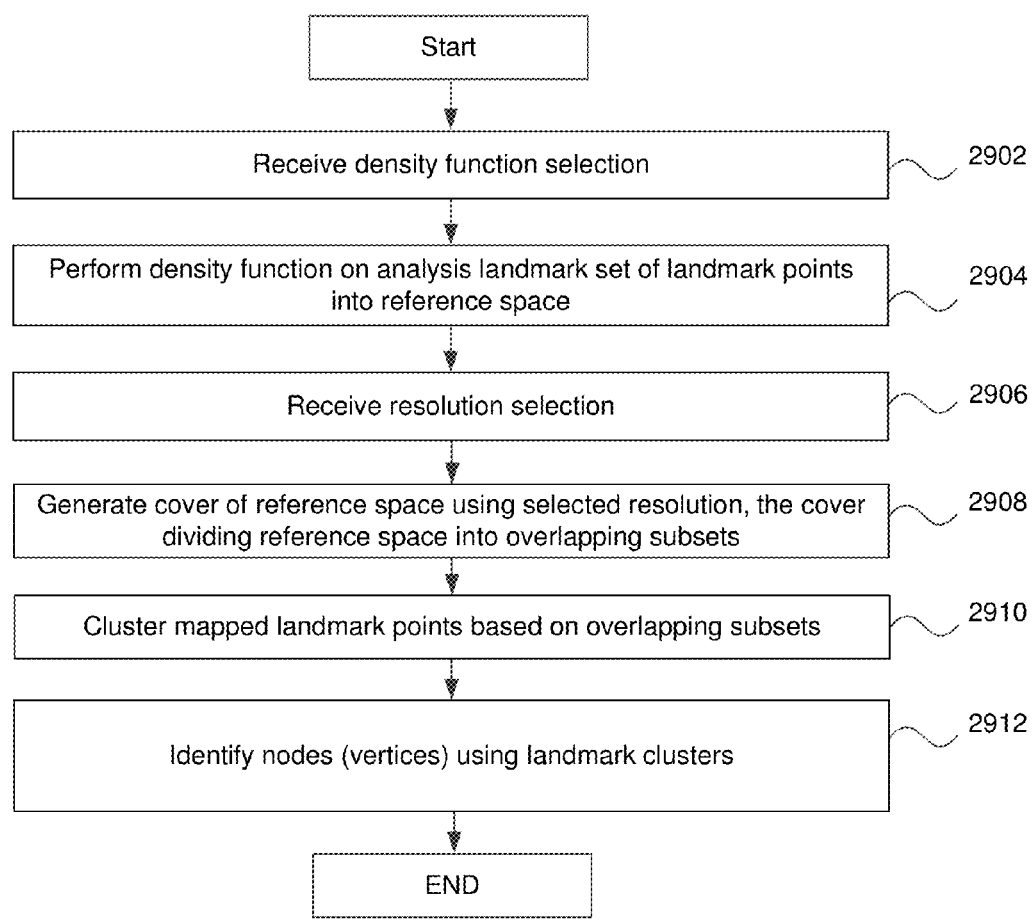
FIG. 29 is a flowchart for a method of the analysis system to identify nodes (e.g., graphical nodes or vertices) associated with one or more of the landmark points of the analysis landmark set of landmark points.

FIG. 29 is a flowchart for a method of the analysis system 2606 to identify nodes (e.g., graphical nodes or vertices) associated with one or more of the landmark points of the analysis landmark set of landmark points. FIG. 29 is an example of the analysis system 2606 applying TDA to identify nodes graphical nodes which may be vertices). The identification of nodes does not necessarily require generation of a visualization (e.g., a visual representation of a graph of nodes and edges).

Computation efficiency is gained by applying TDA to identify nodes associated with landmark points of the analysis landmark set of landmark points rather than the entire large data set. Non-landmark points may be subsequently added to one or more nodes without applying TDA analysis (e.g., shown in FIG. 29) to each non-landmark point. This process of adding non-landmark points to nodes (e.g., graphical nodes or vertices) is further discussed with regard to FIGS. 30-32.

This process of determining nodes is further described herein (e.g., with regard to FIGS. 4, 8, and 12). In step 2902, the analysis system 2606 receives a similarity function. The similarity function may be provided by a user and/or a digital device. In some embodiments, the similarity function is predetermined. The similarity function is a function that may provide a similarity measure to identify similarity between data points. In this example, the analysis system 2606 may receive a density function selection (e.g., a density estimation function selection). It will be appreciated that this process may be characterized as a filter function. Examples include, but are not limited to a Gaussian distribution.

In step 2904, the analysis system 2606 executes the selected filter(s) on the analysis landmark set of landmark points to map those landmark points into a reference space. In one example, a density estimation function, which is well known in the art, may be performed on the analysis landmark set of landmark points.

In step 2906, the analysis system 2606 may receive a resolution selection. The analysis system 2606 may apply the resolution selection to identify overlapping portions of the reference space (e.g., a cover of the reference space. R) in step 2908. The application of the resolution selection generates a cover of the reference space. As discussed herein, the cover of R may be a finite collection of open sets (in the metric of R) such that every point in R lies in at least one of these sets. In various examples, R is k-dimensional Euclidean space, where k is the number of filter functions. It will be appreciated that the cover of the reference space R may be controlled by the number of intervals and the overlap identified in the resolution (e.g., see FIG. 7). For example, the more intervals, the finer the resolution in S (e.g., the similarity space of the received biological data)—that is, the fewer landscape points in each S(d), but the more similar (with respect to the filters) these points may be. The greater the overlap, the more times that clusters in S(d) may intersect clusters in S(e)—this means that more "relationships" between landscape points may appear, but, in some embodiments, the greater the overlap, the more likely that accidental relationships may appear.

In step 2910, the analysis system 2606 receives a metric to cluster the information of the cover in the reference space to partition S(d). In one example, the metric may be a Pearson Correlation. The clusters may form the groupings (e.g., nodes or balls). Various cluster means may be used including, but not limited to, a single linkage, average linkage, complete linkage, or k-means method.

As discussed herein, in some embodiments, the analysis system 2606 may not cluster two points unless filter values are sufficiently "related" (recall that while normally related may mean "close," the cover may impose a much more general relationship on the filter values, such as relating two points s and t if ref(s) and ref(t) are sufficiently close to the same circle in the plane where ref( ) represents one or more filter functions). The output may be a simplicial complex, from which one can extract its 1-skeleton. The nodes of the complex may be partial clusters, (i.e., clusters constructed from subsets of S specified as the preimages of sets in the given covering of the reference space R).

In step 2912, the analysis system 2606 may identify nodes (e.g., graphical nodes or vertices) using the clusters and/or "related" clusters. It will be appreciated that every landscape point of the analysis landscape set of landscape points will be a member of at least one node.

Figure 30:
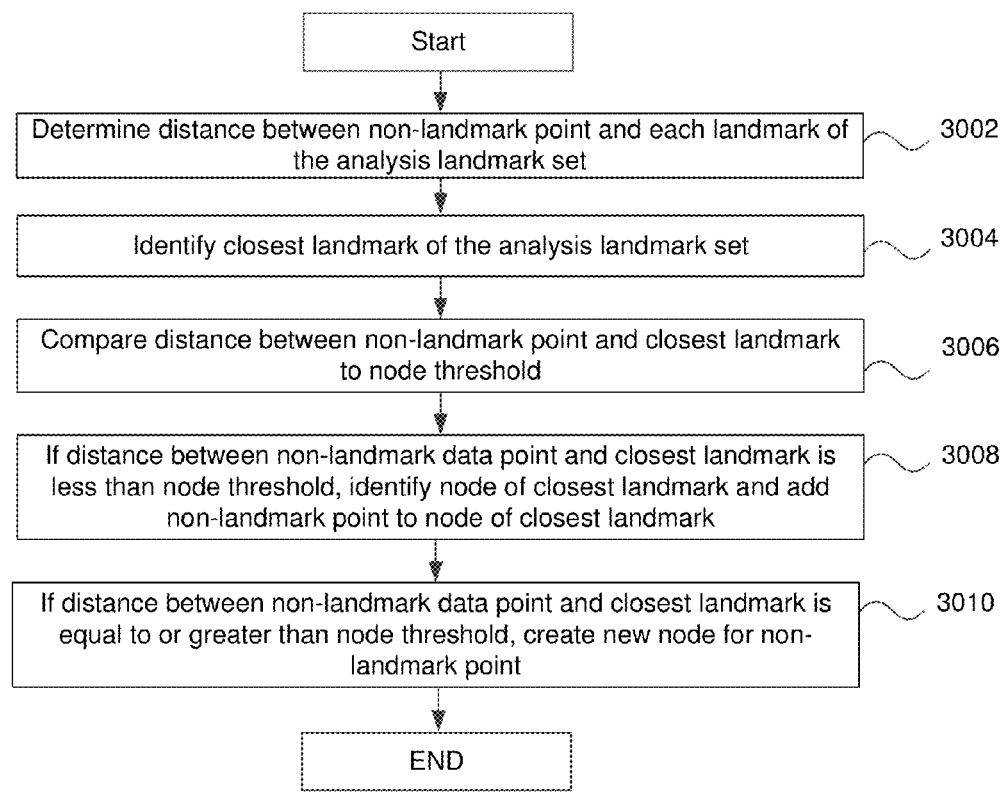
FIG. 30 is a flowchart for adding non-landmark points as members of nodes in some embodiments.

FIG. 30 is a flowchart for adding non-landmark points as members of nodes in some embodiments. This process may be termed as "node fattening" whereby each non-landmark point of the original data set or non-landmark point of the union of landmark subsets is identified as a member of one or more nodes (e.g., graphical nodes or vertices). Adding non-landmark points to nodes as members may be computationally inexpensive when compared to performing analysis (e.g., TDA analysis or most other analytical functions) on a large data set. As a result, limitations may be overcome and the analysis speed increased to generate a graph and/or a visualization of a graph of nodes and edges. Further, analysis of the underlying data using node membership may be quicker to initiate and/or perform.

The following process with regard to FIG. 30 will be discussed using non-landmark points of the original large data set. It will be appreciated that the following process may utilize any data points including, for example, the non-landmark points of the union of landmark subsets. In this example, the analysis system 2606 may generate the analysis landmark set of landmark points by performing further landmarking on the union of landmark subsets. Non-landmark points from the union of landmark subsets may then be added to one or more nodes as members in the process herein.

In step 3002, the analysis system 2606 determines distances between each non-landmark point and each landmark of the analysis landmark set of landmark points. In some embodiments, the analysis system 2606 may utilize distances received from any number of the computation devices 2604*a-d* and/or calculate new distances. For example, the analysis system 2606 may determine distances between each non-landmark point of the original large data set and each of the landmark points of the analysis landmark set of landmark points.

In step 3004, the analysis system 2606 identifies the closest landmark of the analysis landmark set of landmark points using the distances determined in step 3002. In various embodiments, for each non-landmark point, the analysis system 2606 identifies the node (e.g., identified in FIG. 29) associated with the closest identified landmark to that particular non-landmark point and then adds that particular non-landmark point as a member to that node. For example, for a first non-landmark point, the analysis system 2606 identifies the closest landmark of the analysis landmark set to that first non-landmark point. The analysis system 2606 then identifies the node of which the closest landmark is a member and then adds the first non-landmark point as a member of that node. This process may continue for each non-landmark point until all non-landmark points are members of nodes.

It will be appreciated that if the distance between the non-landmark point and the closest landmark is sufficiently long, then the non-landmark point may be added as a member of a new node (i.e., a node with a membership of that particular non-landmark point) rather than a member of a previously existing node (i.e., a node with the closest landmark point as being at least one member).

For example, in some embodiments, for each non-landmark point, the analysis system 2606 may compare the distance between that particular non-landmark point and its closest landmark point to a node threshold in step 3006. A node threshold is a predetermined distance. In step 3008, if the distance between a particular non-landmark point and its closest landmark point is less than (or equal to in some embodiments) the node threshold, the analysis system 2606 may add the particular non-landmark point as a member of the node of that closest landmark. Alternately, in step 3010, if the distance between that particular non-landmark point and its closest landmark point is greater than (or equal to in some embodiments) the node threshold, the analysis system 2606 may create a new node for the non-landmark point and make the non-landmark point a member of the new node.

In some embodiments, the new node may be placed on the graph relative to other nodes based on the distance between the particular non-landmark point and the closest landmark point.

Figure 31:
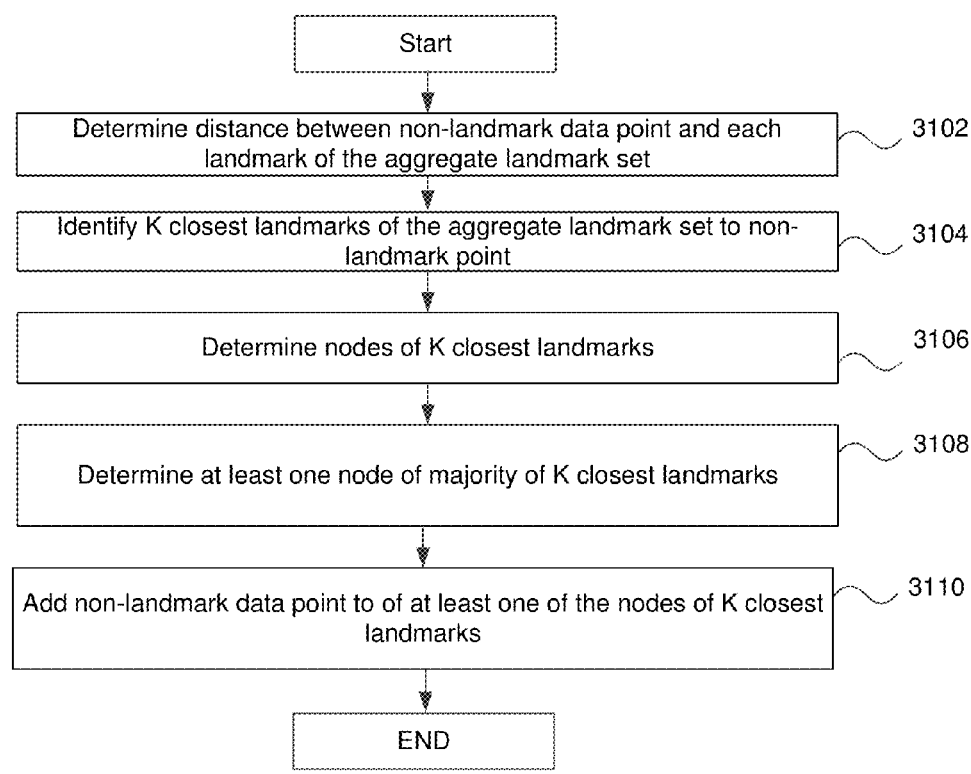
FIG. 31 is another flowchart for adding non-landmark points as members of nodes in some embodiments.

FIG. 31 is another flowchart for adding non-landmark points as members of nodes in some embodiments. This process is similar to that discussed with regard to FIG. 30, however, membership of the non-landmark node may be based on a group of closest landmark points rather than only one landmark point. As discussed with regard to FIG. 30, the following process will be discussed using non-landmark points of the original large data set. It will be appreciated that the following process may utilize any data points including, for example, the non-landmark points of the union of landmark subsets. In this example, the analysis system 2606 may generate the analysis landmark set of landmark points by performing further landmarking on the union of landmark subsets. Non-landmark points from the union of landmark subsets may then be added to one or more nodes as members in the process herein.

In step 3102, the analysis system 2606 determines distances between each non-landmark point and each landmark of the analysis landmark set of landmark points. In some embodiments, the analysis system 2606 may utilize distances received from any number of the computation devices 2604*a-d* and/or calculate new distances. For example, the analysis system 2606 may determine distances between each non-landmark point of the original large data set and each of the landmark points of the analysis landmark set of landmark points.

In step 3104, the analysis system 2606 identifies k closest landmarks of the analysis landmark set of landmark points using the distances determined. K is a predetermined integer greater than 1. In some embodiments, a user or a digital device may provide the value of k. K can be any integer.

In various embodiments, for each non-landmark point, the analysis system 2606 identifies the nodes (e.g., identified in FIG. 29) associated with the k closest identified landmark points to that particular non-landmark point in step 3106. In step 3108, for each non-landmark point, the analysis system 2606 may determine which node includes the majority of the k closest identified landmark points and then, in step 3110, the analysis system 2606 may assign that particular non-landmark point to the node. If no node has a majority of the closest identified landmark points as members, the analysis system 2606 may assign the non-landmark point as a member of the node with the closest non-landmark point.

It will be appreciated that the analysis system 2606 may assign membership of any particular non-landmark point in any number of ways. For example, the analysis system 2606 may order the k closest identified landmark points based on distance to the particular non-landmark point. If no node has a majority of the closest identified landmark points as members, the analysis system 2606 may assign membership of the non-landmark point to the node containing the closest two landmark points of the k closest identified landmark points.

In various embodiments, the analysis system 2606 may assign membership of the non-landmark point to the node containing the closest m landmark points of the k closest identified landmark points (m being a predetermined integer less than k). The value of m may be provided by a digital device and/or a user. In some embodiments, if there are no nodes containing the closest m landmark points of the k closest identified landmark points, the analysis system 2606 may assign membership of the non-landmark point to the node containing the closest m−1 landmark points of the k closest identified landmark points. This process may continue if there are no nodes closest to m−1 landmark points. For example, if there are no nodes containing the closest m−1 landmark points of the k closest identified landmark points, the analysis system 2606 may assign membership of the non-landmark point to the node containing the closest m−2 landmark points of the k closest identified landmark points and so on.

Figure 32:
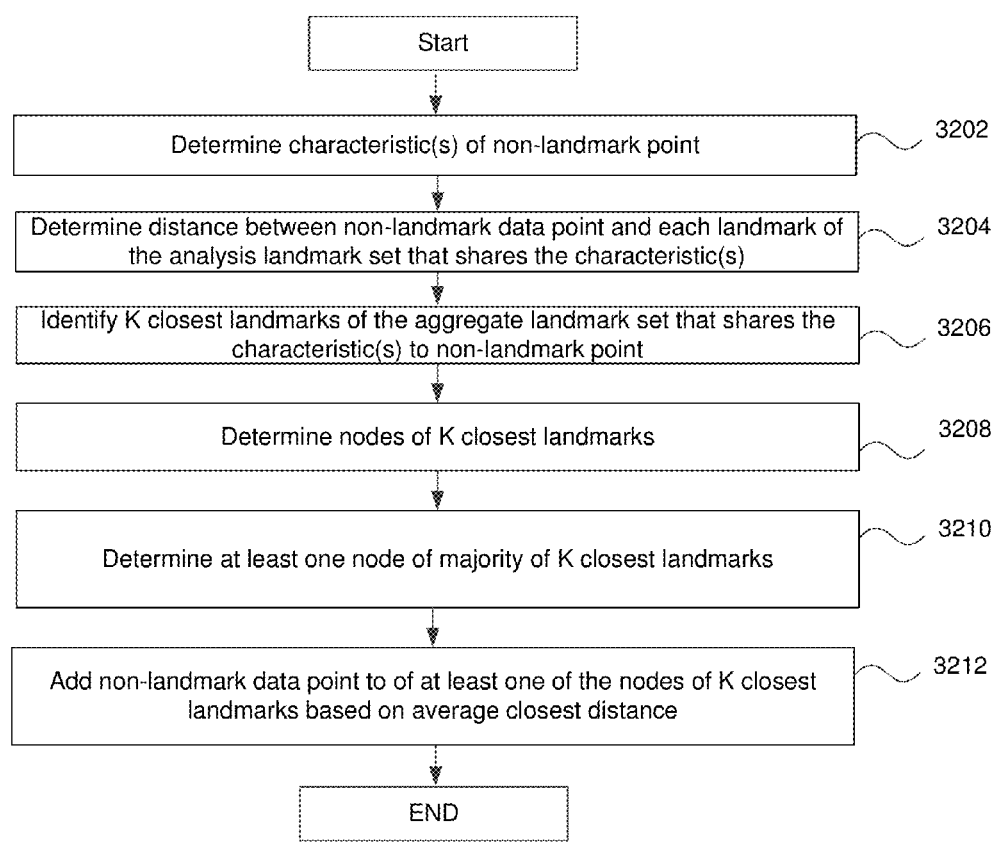
FIG. 32 is a flowchart for adding non-landmark points as members of nodes that share one or more characteristic(s) in some embodiments.

FIG. 32 is a flowchart for adding non-landmark points as members of nodes that share one or more characteristic(s) in some embodiments. This process is similar to that discussed with regard to FIG. 31, however, membership of the non-landmark node may be based on a group of closest landmark points that share characteristic(s). The following process will be discussed using non-landmark points of the original large data set. It will be appreciated that the following process may utilize any data points including, for example, the non-landmark points of the union of landmark subsets. In this example, the analysis system 2606 may generate the analysis landmark set of landmark points by performing further landmarking on the union of landmark subsets. Non-landmark points from the union of landmark subsets may then be added to one or more nodes as members in the process herein.

In step 3102, for each non-landmark data point, the analysis system 2606 may identify one or more characteristics. The characteristics may information regarding the data point from the original data set. For example, the characteristic(s) may include values associated with one or more columns of the data set. The analysis system 2606 may then determine distances between each non-landmark point and each landmark of the analysis landmark set that shares the characteristic(s) with the non-landmark point. This approach may be called "neighborhood lensing."

It will be appreciated that the analysis system 2606 may determine if a non-landmark point shares characteristic(s) with one or more landmark points in any number of ways. In some embodiments, the analysis system 2606 may apply a function to one or more characteristic(s) of a particular non-landmark point and the landmark points. For example, the analysis system 2606 may determine if a non-landmark point indicates that a particular test was conducted at or before a certain date (e.g., the data points of the data sets may represent patients and at least some of the characteristics of the patients may indicate if a test was performed and when). The analysis system 2606 may determine the landmark points that also indicate that the same test was conducted at or before a certain date (e.g., which landmark points share the characteristic(s) of the non-landmark point). The analysis system 2606 may then determine membership of the non-landmark point as discussed herein using only the landmark points that share characteristics.

This process may be performed in any way. For example, the analysis system 2606 may determine membership of a landmark point using only the landmark points that do not share the characteristics with the non-landmark point, share a degree of similarity between any number of characteristics, or share a degree of dissimilarity between any number of characteristics.

In step 3204, the analysis system 2606 determines distances between each non-landmark point and each landmark of the analysis landmark set of landmark points that share the characteristic(s) with the respective non-landmark point. In some embodiments, the analysis system 2606 may utilize distances received from any number of the computation devices 2604*a-d* and/or calculate new distances. For example, the analysis system 2606 may determine distances between each non-landmark point of the original large data set and each of the landmark points of the analysis landmark set of landmark points share characteristic(s) with the respective non-landmark point.

In step 3206, the analysis system 2606 identifies k closest landmarks of the analysis landmark set of landmark points that share characteristic(s) with the respective non-landmark point using the distances determined. K is a predetermined integer greater than 1. In some embodiments, a user or a digital device may provide the value of k. K can be any integer.

In various embodiments, for each non-landmark point, the analysis system 2606 identifies the nodes (e.g., identified in FIG. 29) associated with the k closest identified landmark points share characteristic(s) with the particular non-landmark point in step 3208. In step 3210, for each non-landmark point, the analysis system 2606 may determine which node includes the majority of the k closest identified landmark points and then, in step 3212, the analysis system 2606 may assign that particular non-landmark point to the node. As discussed herein, if no node has a majority of the closest identified landmark points as members, the analysis system 2606 may assign the non-landmark point as a member of the node with the closest non-landmark point that share the characteristic(s).

It will be appreciated that the analysis system 2606 may assign membership of any particular non-landmark point in any number of ways. For example, the analysis system 2606 may order the k closest identified landmark points based on distance to the particular non-landmark point. If no node has a majority of the closest identified landmark points as members, the analysis system 2606 may assign membership of the non-landmark point to the node containing the closest two landmark points of the k closest identified landmark points.

In various embodiments, the analysis system 2606 may assign membership of the non-landmark point to the node containing the closest m landmark points of the k closest identified landmark points (m being a predetermined integer less than k). The value of m may be provided by a digital device and/or a user. In some embodiments, if there are no nodes containing the closest m landmark points of the k closest identified landmark points, the analysis system 2606 may assign membership of the non-landmark point to the node containing the closest m−1 landmark points of the k closest identified landmark points. This process may continue. For example, if there are no nodes containing the closest m−1 landmark points of the k closest identified landmark points, the analysis system 2606 may assign membership of the non-landmark point to the node containing the closest m−2 landmark points of the k closest identified landmark points and so on.

The above-described functions and components can be comprised of instructions that are stored on a storage medium (e.g., a computer readable storage medium). The instructions can be retrieved and executed by a processor. Some examples of instructions are software, program code, and firmware. Some examples of storage medium are memory devices, tape, disks, integrated circuits, and servers. The instructions are operational when executed by the processor (e.g., a data processing device) to direct the processor to operate in accord with embodiments of the present invention. Those skilled in the art are familiar with instructions, processor(s), and storage medium.

The present invention has been described above with reference to exemplary embodiments. It will be apparent to those skilled in the art that various modifications may be made and other embodiments can be used without departing from the broader scope of the invention. Therefore, these and other variations upon the exemplary embodiments are intended to be covered by the present invention.

What is claimed is:

1. A method comprising:
receiving a large number of data points;
determining at least one size of a plurality of subsets of the large number of data points based on constraints of at least one of a plurality of computation devices or an analysis server, each data point of the large number of data points being a member of at least one of the plurality of subsets of the large number of data points;
transferring each of the plurality of subsets of the large number of data points to a respective one of the plurality of computation devices;
for each of the plurality of subsets of data points by an associated computation device of the plurality of computation devices:
    selecting, by the associated computation device, a group of data points from the subset of data points to generate a first sub-subset of landmarks;
    adding, by the associated computation device, a non-landmark data point of the subset of data points to the first sub-subset of landmarks to create an expanded sub-subset of landmarks, adding the non-landmark data points comprising:
        calculating first data point distances between each non-landmark data point and each landmark;
        identifying a shortest data point distance from among the first data point distances for each non-landmark data point;
        identifying a particular non-landmark data point with a longest first landmark distance of all the shortest data path distances; and
        adding the particular non-landmark data point to the first sub-subset of landmarks to expand the first sub-subset of landmarks to generate an expanded set of landmarks;
    repeating the adding the non-landmark data points until the expanded sub-subset of the expanded landmarks reaches a predetermined number of members;
creating an analysis landmark set based on a combination of the expanded sub-subsets of expanded landmarks;
performing a similarity function on the analysis landmark set to map landmark points of the analysis landmark set to a mathematical reference space;
generating a cover of the mathematical reference space to divide the mathematical reference space into overlapping subsets;
clustering the mapped landmark points of the analysis landmark set based on the overlapping subsets of the cover in the mathematical reference space;
creating a plurality of nodes, each of the plurality of nodes being based on the clustering of the mapped landmark points of the analysis landmark set, each landmark point of the analysis landmark set being a member of at least one node;
connecting at least two of the plurality of nodes with an edge if the at least two of the plurality of nodes share at least one landmark point of the analysis landmark set as a member; and
generating a visualization of at least a subset of the plurality of nodes, the visualization including the edge connecting the at least two of the plurality of nodes.

2. The method of claim 1 further comprising:
for each data point that is a member of the large number of data points but is not a member of the analysis landmark set:
    determining a distance between that data point and all landmark points of the analysis landmark set;
    identifying a closest landmark of the analysis landmark set to that data point;
    identifying a node that includes the closest landmark of the analysis landmark set; and
    adding that data point as a member of the node that includes the closest landmark of the analysis landmark set.

3. The method of claim 1 further comprising:
for each data point that is a member of the large number of data points but is not a member of the analysis landmark set:
    determining a distance between that data point and all landmark points of the analysis landmark set;
    identifying a closest landmark of the analysis landmark set to that data point;
    comparing a distance between the closest landmark of the analysis landmark set and that data point to a node threshold; and
    if the distance between the closest landmark of the analysis landmark set and that data point is greater than the node threshold, generating a new node including that data point as a member of the new node;

if the distance the distance between the closest landmark of the analysis landmark set and that data point is less than the node threshold, adding that data point as a member of the node that includes the closest landmark of the analysis landmark set.

4. The method of claim 1 further comprising:

for each data point that is a member of the large number of data points but is not a member of the analysis landmark set:

determining a distance between that data point and all landmark points of the analysis landmark set;

identifying a predetermined number of closest landmarks of the analysis landmark set to that data point;

identifying a node which includes a majority of the predetermined number of closest landmarks of the analysis landmark set as members; and adding that data point as a member of the node that includes a majority of the predetermined number of closest landmarks of the analysis landmark set as members.

5. The method of claim 1, further comprising determining the predetermined number of members of the expanded sub-subset of the expanded landmarks based on the constraints of the at least one of a plurality of computation devices or an analysis server.

6. The method of claim 5, wherein the determination of the predetermined number of members of the expanded sub-subset of the expanded landmarks is based, at least in part, on a determination of a predetermined number of members of the analysis landmark set.

7. The method of claim 1, wherein selecting, by the associated computation device, the group of data points from the subset of data points to generate the first sub-subset of landmarks is performed randomly.

8. A non-transitory computer readable medium comprising instructions executable by a processor to perform a method, the method comprising:

receiving a large number of data points;

transferring each of a plurality of subsets of the large number of data points to a respective one of a plurality of computation devices;

for each of the plurality of subsets of the large number of data points by an associated computation device of the plurality of computation devices:

selecting, by the associated computation device, a group of data points from the subset of data points to generate a first sub-subset of landmarks;

adding, by the associated computation device, a non-landmark data point of the subset of data points to the first sub-subset of landmarks to create an expanded sub-subset of landmarks, adding the non-landmark data points comprising:

calculating first data point distances between each non-landmark data point and each landmark;

identifying a shortest data point distance from among the first data point distances for each non-landmark data point;

identifying a particular non-landmark data point with a longest first landmark distance of all the shortest data path distances; and adding the particular non-landmark data point to the first sub-subset of landmarks to expand the first sub-subset of landmarks to generate an expanded set of landmarks;

repeating the adding the non-landmark data points until the expanded sub-subset of the expanded landmarks reaches a predetermined number of members;

creating an analysis landmark set based on a combination of the expanded sub-subsets of expanded landmarks;

performing a similarity function on the analysis landmark set to map landmark points of the analysis landmark set to a mathematical reference space;

generating a cover of the mathematical reference space to divide the mathematical reference space into overlapping subsets;

clustering the mapped landmark points of the analysis landmark set based on the overlapping subsets of the cover in the mathematical reference space;

creating a plurality of nodes, each of the plurality of nodes being based on the clustering of the mapped landmark points of the analysis landmark set, each landmark point of the analysis landmark set being a member of at least one node;

connecting at least two of the plurality of nodes with an edge if the at least two of the plurality of nodes share at least one landmark point of the analysis landmark set as a member; and generating a visualization of at least a subset of the plurality of nodes, the visualization including the edge connecting the at least two of the plurality of nodes.

9. The non-transitory computer readable medium of claim 8 wherein the method further comprises:

for each data point that is a member of the large number of data points but is not a member of the analysis landmark set:

determining a distance between that data point and all landmark points of the analysis landmark set;

identifying a closest landmark of the analysis landmark set to that data point;

identifying a node that includes the closest landmark of the analysis landmark set; and adding that data point as a member of the node that includes the closest landmark of the analysis landmark set.

10. The non-transitory computer readable medium of claim 8 wherein the method further comprises:

for each data point that is a member of the large number of data points but is not a member of the analysis landmark set:

determining a distance between that data point and all landmark points of the analysis landmark set;

identifying a closest landmark of the analysis landmark set to that data point;

comparing a distance between the closest landmark of the analysis landmark set and that data point to a node threshold; and if the distance between the closest landmark of the analysis landmark set and that data point is greater than the node threshold, generating a new node including that data point as a member of the new node;

if the distance the distance between the closest landmark of the analysis landmark set and that data point is less than the node threshold, adding that data point as a member of the node that includes the closest landmark of the analysis landmark set.

11. The non-transitory computer readable medium of claim 8 wherein the method further comprises:

for each data point that is a member of the large number of data points but is not a member of the analysis landmark set:

determining a distance between that data point and all landmark points of the analysis landmark set;

identifying a predetermined number of closest landmarks of the analysis landmark set to that data point;

identifying a node which includes a majority of the predetermined number of closest landmarks of the analysis landmark set as members; and adding that data point as a member of the node that includes a majority of the predetermined number of closest landmarks of the analysis landmark set as members.

12. The non-transitory computer readable medium of claim 8 wherein the method further comprises determining the predetermined number of members of the expanded sub-subset of the expanded landmarks based on the constraints of the at least one of a plurality of computation devices or an analysis server.

13. The non-transitory computer readable medium of claim 12, wherein the determination of the predetermined number of members of the expanded sub-subset of the expanded landmarks is based, at least in part, on a determination of a predetermined number of members of the analysis landmark set.

14. The non-transitory computer readable medium of claim 8, wherein selecting, by the associated computation device, the group of data points from the subset of data points to generate the first sub-subset of landmarks is performed randomly.

15. A system comprising:

at least one processor; and memory configured to contain instructions to control the processor to:

receive a large number of data points;

determine at least one size of a plurality of subsets of the large number of data points based on constraints of at least one of a plurality of computation devices or an analysis server, each data point of the large number of data points being a member of at least one of the plurality of subsets of the large number of data points;

transfer each of the plurality of subsets of the large number of data points to a respective one of the plurality of computation devices to enable for each of the plurality of subsets of data points by an associated computation device of the plurality of computation devices to:

select, by the associated computation device, a group of data points from the subset of data points to generate a first sub-subset of landmarks;

add, by the associated computation device, a non-landmark data point of the subset of data points to the first sub-subset of landmarks to create an expanded sub-subset of landmarks, adding the non-landmark data points comprising:

calculating first data point distances between each non-landmark data point and each landmark;

identifying a shortest data point distance from among the first data point distances for each non-landmark data point;

identifying a particular non-landmark data point with a longest first landmark distance of all the shortest data path distances; and adding the particular non-landmark data point to the first sub-subset of landmarks to expand the first sub-subset of landmarks to generate an expanded set of landmarks;

repeat the adding the non-landmark data points until the expanded sub-subset of the expanded landmarks reaches a predetermined number of members;

create an analysis landmark set based on a combination of the expanded sub-subsets of expanded landmarks;

perform a similarity function on the analysis landmark set to map landmark points of the analysis landmark set to a mathematical reference space;

generate a cover of the mathematical reference space to divide the mathematical reference space into overlapping subsets;

cluster the mapped landmark points of the analysis landmark set based on the overlapping subsets of the cover in the mathematical reference space;

create a plurality of nodes, each of the plurality of nodes being based on the clustering of the mapped landmark points of the analysis landmark set, each landmark point of the analysis landmark set being a member of at least one node;

connect at least two of the plurality of nodes with an edge if the at least two of the plurality of nodes share at least one landmark point of the analysis landmark set as a member; and generate a visualization of at least a subset of the plurality of nodes, the visualization including the edge connecting the at least two of the plurality of nodes.

* * * * *